United States Patent
Koch et al.

(10) Patent No.: US 11,384,369 B2
(45) Date of Patent: Jul. 12, 2022

(54) MICROORGANISMS AND METHODS FOR THE PRODUCTION OF GLYCOLIC ACID AND GLYCINE VIA REVERSE GLYOXYLATE SHUNT

(71) Applicant: Braskem S.A., Sao Paulo (BR)

(72) Inventors: Daniel Johannes Koch, Campinas (BR); Felipe Galzerani, Campinas (BR); Paulo Moises Raduan Alexandrino, Campinas (BR)

(73) Assignee: BRASKEM S.A., Camacari (BR)

( * ) Notice: Subject to any disclaimer, the term of this patent is extended or adjusted under 35 U.S.C. 154(b) by 0 days.

(21) Appl. No.: 16/791,556

(22) Filed: Feb. 14, 2020

(65) Prior Publication Data

US 2020/0263210 A1   Aug. 20, 2020

Related U.S. Application Data

(60) Provisional application No. 62/806,195, filed on Feb. 15, 2019.

(51) Int. Cl.
| | |
|---|---|
| *C12N 9/88* | (2006.01) |
| *C12N 9/90* | (2006.01) |
| *C12N 1/20* | (2006.01) |
| *C12P 7/42* | (2006.01) |
| *C12P 13/00* | (2006.01) |
| *C12N 9/00* | (2006.01) |
| *C12P 13/04* | (2006.01) |

(52) U.S. Cl.
CPC .............. *C12P 7/42* (2013.01); *C12N 9/88* (2013.01); *C12N 9/93* (2013.01); *C12P 13/04* (2013.01); *C12Y 401/03001* (2013.01); *C12Y 401/03024* (2013.01); *C12Y 604/01001* (2013.01)

(58) Field of Classification Search
CPC ........ C12N 15/902; C12N 15/63; C12N 9/88; C12N 9/16; C12N 9/0008; C12N 9/1205; C12P 7/42; C12P 13/04; C12P 7/625; C12Y 207/02003; C12Y 401/03024; C12Y 604/01001; C12Y 101/01037; C12Y 101/01038; C12Y 101/05004
USPC ... 435/69.1, 252.31, 253.1, 252.3, 136, 146, 435/189, 194, 195, 320.1
See application file for complete search history.

(56) References Cited

U.S. PATENT DOCUMENTS

| | | | |
|---|---|---|---|
| 8,911,978 B2 | 12/2014 | Soucaille et al. | |
| 8,945,888 B2 | 2/2015 | Dischert et al. | |
| 9,034,615 B2 | 5/2015 | Soucaille | |
| 9,410,131 B2 | 8/2016 | Milo et al. | |
| 2009/0325245 A1 | 12/2009 | Soucaille et al. | |
| 2011/0294178 A1 | 12/2011 | Soucaille et al. | |
| 2011/0312049 A1 | 12/2011 | Osterhout et al. | |
| 2012/0178136 A1 | 7/2012 | Dischert et al. | |
| 2013/0210097 A1 | 8/2013 | Dischert et al. | |
| 2013/0316416 A1 | 11/2013 | Stephanopoulos et al. | |
| 2014/0295510 A1 | 10/2014 | Koivistoinen et al. | |
| 2015/0111261 A1 | 4/2015 | Jurgen-Lohmann et al. | |
| 2015/0147794 A1 | 5/2015 | Chung et al. | |
| 2016/0076061 A1 | 3/2016 | Stephanopoulos et al. | |
| 2016/0369292 A1 | 12/2016 | Liao et al. | |
| 2017/0121717 A1 | 5/2017 | Stephanopoulos et al. | |

FOREIGN PATENT DOCUMENTS

| | | |
|---|---|---|
| CN | 105647844 | 6/2016 |
| CN | 106011185 | 10/2016 |
| EP | 2738247 A1 | 6/2014 |
| EP | 2738247 B1 | 6/2014 |
| FR | 3028529 A1 | 5/2016 |
| WO | WO-2012177983 A2 | 12/2012 |
| WO | WO-2014004625 A1 | 1/2014 |
| WO | WO-2014049382 A2 | 4/2014 |

(Continued)

OTHER PUBLICATIONS

Bar-Even, A. et al., "Design and analysis of synthetic carbon fixation pathways", Proceedings of the National Academy of Sciences, National Academy of Sciences, vol. 107, No. 19, May 11, 2010 (May 11, 2010), pp. 8889-8894, XP002638327, ISSN:0027-8424, DOI: 10.1073/PNAS.0907176107 [retrieved on Apr. 21, 2010] the whole document.

(Continued)

*Primary Examiner* — Robert B Mondesi
*Assistant Examiner* — Mohammad Y Meah
(74) *Attorney, Agent, or Firm* — Morgan, Lewis & Bockius LLP

(57) ABSTRACT

The present invention provides biochemical pathways, glyoxylate producing recombinant microorganisms, and methods for the production and yield improvement of glycolic acid and/or glycine via a reverse glyoxylate shunt. The reverse glyoxylate shunt comprises an enzyme that catalyzes the carboxylation of phosphoenol pyruvate (PEP) to oxaloacetate (OAA), or an enzyme that catalyzes the carboxylation of pyruvate to oxaloacetate (OAA) or an enzyme that catalyzes the carboxylation of pyruvate to malate or a combination of any of the previous reactions; an enzyme that catalyzes the conversion of malate to malyl-CoA; an enzyme that catalyzes the conversion of malyl-CoA to glyoxylate and acetyl-CoA; and optionally an enzyme that catalyzes the conversion of oxaloacetate (OAA) to malate. Glyoxylate is reduced to produce glycolate. Alternatively, glyoxylate is converted to glycine. The reverse glyoxylate shunt pathway of the present invention can be utilized synergistically with other glycolic acid and/or glycine producing pathways to increase product yield.

18 Claims, 4 Drawing Sheets

Specification includes a Sequence Listing.

(56) References Cited

FOREIGN PATENT DOCUMENTS

| WO | WO-2014162063 A1 | 10/2014 |
| WO | WO-2014210587 A1 | 12/2014 |
| WO | WO-2015181074 A1 | 12/2015 |
| WO | WO-2016079440 A1 | 5/2016 |
| WO | WO-2016193540 A1 | 12/2016 |
| WO | WO-2017059236 A1 | 4/2017 |

OTHER PUBLICATIONS

International Search Report for Application No. PCT/BR2020/050041, dated Jun. 6, 2020, 15 pages.

Mainguet, S. E et al., "A reverse glyoxylate shunt to build a non-native route from $C_4$ to $C_2$ in *Escherichia coli*", Metabolic Engineering, vol. 19, Aug. 16, 2013 (Aug. 16, 2013), pp. 116-127, XP055311350, US ISSN:1096-7176, DOI: 10.1016/j.ymben.2013.06.004 abstract; figure 1 p. 118, right-hand column, last paragraph—p. 125, right-hand column, last paragraph; figures 2, 3, 5; table 1.

Yu, H. et al., "A modified serine cycle in Escherichia coli coverts methanol and CO2 to two-carbon compounds", Nature Communications, vol. 9, No. 1, Sep. 28, 2018 (Sep. 28, 2018), pp. 1-10, XP055694422, DOI: 10.1038/S41467-018-06496-4 p. 3, line 2, last paragraph; figure 1 p. 5, left-hand column paragraph 2—p. 7, left-hand column paragraph 1; figures 2,3; table 1.

SEQUENCE LISTING

<160> NUMBER OF SEQ ID NOS: 38

<210> SEQ ID NO 1
<211> LENGTH: 60
<212> TYPE: DNA
<213> ORGANISM: Artificial Sequence
<220> FEATURE:
<223> OTHER INFORMATION: Primer Pgi_N20_FW

<400> SEQUENCE: 1
gtcctaggta taatactagt ccgattatct ggggtgaacc gttttagagc tagaaatagc    60

<210> SEQ ID NO 2
<211> LENGTH: 24
<212> TYPE: DNA
<213> ORGANISM: Artificial Sequence
<220> FEATURE:
<223> OTHER INFORMATION: Primer Pgi_N20_RV

<400> SEQUENCE: 2
actagtatta tacctaggac tgag                                           24

<210> SEQ ID NO 3
<211> LENGTH: 22
<212> TYPE: DNA
<213> ORGANISM: Artificial Sequence
<220> FEATURE:
<223> OTHER INFORMATION: Primer Pgi_H1_FW

<400> SEQUENCE: 3
atgaaaaaca tcaatccaac gc                                             22

<210> SEQ ID NO 4
<211> LENGTH: 29
<212> TYPE: DNA
<213> ORGANISM: Artificial Sequence
<220> FEATURE:
<223> OTHER INFORMATION: Primer Pgi_H1_RV

<400> SEQUENCE: 4
ggtggatcag tcggtcacca tgtatgggc                                      29

<210> SEQ ID NO 5
<211> LENGTH: 29
<212> TYPE: DNA
<213> ORGANISM: Artificial Sequence
<220> FEATURE:
<223> OTHER INFORMATION: Primer Pgi_H2_FW

<400> SEQUENCE: 5
tggtgaccga ctgatccacc agggaacca                                      29

<210> SEQ ID NO 6
<211> LENGTH: 22
<212> TYPE: DNA
<213> ORGANISM: Artificial Sequence
<220> FEATURE:
<223> OTHER INFORMATION: Primer Pgi_H2_RV

<400> SEQUENCE: 6
catatcgacg atgattaacc gc                                             22

<210> SEQ ID NO 7
<211> LENGTH: 46
<212> TYPE: DNA
<213> ORGANISM: Artificial Sequence

```
<220> FEATURE:
<223> OTHER INFORMATION: Primer pvc_FW

<400> SEQUENCE: 7
ttgtttaact ttaaggaggt ttggaggtac catgcccata tccaag            46

<210> SEQ ID NO 8
<211> LENGTH: 42
<212> TYPE: DNA
<213> ORGANISM: Artificial Sequence
<220> FEATURE:
<223> OTHER INFORMATION: Primer pvc_RV

<400> SEQUENCE: 8
ttttcatacg gttcctcctt ctagatcatc cgccgtaaac cg                42

<210> SEQ ID NO 9
<211> LENGTH: 48
<212> TYPE: DNA
<213> ORGANISM: Artificial Sequence
<220> FEATURE:
<223> OTHER INFORMATION: Primer aceA_FW

<400> SEQUENCE: 9
cggatgatct agaaggagga accgtatgaa aacccgtaca caacaaat          48

<210> SEQ ID NO 10
<211> LENGTH: 47
<212> TYPE: DNA
<213> ORGANISM: Artificial Sequence
<220> FEATURE:
<223> OTHER INFORMATION: Primer aceA_RV

<400> SEQUENCE: 10
ttgtatcagc catcgtgtgc ctcctttaga actgcgattc ttcagtg           47

<210> SEQ ID NO 11
<211> LENGTH: 49
<212> TYPE: DNA
<213> ORGANISM: Artificial Sequence
<220> FEATURE:
<223> OTHER INFORMATION: Primer gltA_FW

<400> SEQUENCE: 11
atcgcagttc taaggaggc acacgatggc tgatacaaaa gcaaaactc          49

<210> SEQ ID NO 12
<211> LENGTH: 52
<212> TYPE: DNA
<213> ORGANISM: Artificial Sequence
<220> FEATURE:
<223> OTHER INFORMATION: Primer gltA_RV

<400> SEQUENCE: 12
agatgatatc catcgtgtgc ctcctttaac gcttgatatc gcttttaaag tc     52

<210> SEQ ID NO 13
<211> LENGTH: 51
<212> TYPE: DNA
<213> ORGANISM: Artificial Sequence
<220> FEATURE:
<223> OTHER INFORMATION: Primer ghrA_FW

<400> SEQUENCE: 13
tatcaagcgt taaggaggc acacgatgga tatcatcttt tatcacccaa c       51
```

<210> SEQ ID NO 14
<211> LENGTH: 43
<212> TYPE: DNA
<213> ORGANISM: Artificial Sequence
<220> FEATURE:
<223> OTHER INFORMATION: Primer ghrA_RV

<400> SEQUENCE: 14
ggctgcagga attcgatatc atagattagt agccgcgtgc gcg          43

<210> SEQ ID NO 15
<211> LENGTH: 49
<212> TYPE: DNA
<213> ORGANISM: Artificial Sequence
<220> FEATURE:
<223> OTHER INFORMATION: Primer sucCD_FW

<400> SEQUENCE: 15
acaatttcac acaggaaaca gaattcctat aattttgttt aactttaag          49

<210> SEQ ID NO 16
<211> LENGTH: 29
<212> TYPE: DNA
<213> ORGANISM: Artificial Sequence
<220> FEATURE:
<223> OTHER INFORMATION: Primer sucCD_RV

<400> SEQUENCE: 16
tatagtctag atcagaatct gattccgtg          29

<210> SEQ ID NO 17
<211> LENGTH: 49
<212> TYPE: DNA
<213> ORGANISM: Artificial Sequence
<220> FEATURE:
<223> OTHER INFORMATION: Primer mcl_FW

<400> SEQUENCE: 17
gaatcagatt ctgatctaga ctataatttt gtttaacttt aaggaggtt          49

<210> SEQ ID NO 18
<211> LENGTH: 29
<212> TYPE: DNA
<213> ORGANISM: Artificial Sequence
<220> FEATURE:
<223> OTHER INFORMATION: Primer mcl_RV

<400> SEQUENCE: 18
tagcacgcgt ttactttccg cccatcgcg          29

<210> SEQ ID NO 19
<211> LENGTH: 148
<212> TYPE: DNA
<213> ORGANISM: Artificial Sequence
<220> FEATURE:
<223> OTHER INFORMATION: J23119 Promoter

<400> SEQUENCE: 19
gacgtccaca gctaacacca cgtcgtccct atctgctgcc ctaggtctat gagtggttgc          60
tggataactt gacagctagc tcagtcctag gtataatgct agctaataga aataattttg          120
tttaacttta aggaggtttg gaggtacc          148

<210> SEQ ID NO 20
<211> LENGTH: 3465

<212> TYPE: DNA
<213> ORGANISM: Rhizobium etli pyc

<400> SEQUENCE: 20

```
atgcccatat ccaagatact cgttgccaat cgctctgaaa tagccatccg cgtgttccgc      60
gcggccaacg agcttggaat aaaaacggtg gcgatctggg cggaagagga caagctggcg     120
ctgcaccgct tcaaggcgga cgagagttat caggtcggcc gcggaccgca tcttgcccgc     180
gacctcgggc cgatcgaaag ctatctgtcg atcgacgagg tgatccgcgt cgccaagctt     240
tccggtgccg acgccatcca tccgggctac ggcctcttgt cggaaagccc cgaattcgtc     300
gatgcctgca acaaggccgg catcatcttc atcggcccga aggccgatac gatgcgccag     360
cttggcaaca aggtcgcagc gcgcaacctg gcgatctcgg tcggcgtacc ggtcgtgccg     420
gcgaccgagc cactgccgga cgatatggcc gaagtggcga agatggcggc ggcgatcggc     480
tatcccgtca tgctgaaggc atcctggggc ggcggcggtc gcggcatgcg cgtcattcgt     540
tccgaggccg acctcgccaa ggaagtgacg gaagccaagc gcgaggcgat ggcggccttc     600
ggcaaggacg aggtctatct cgaaaaactg gtcgagcgcg cccgccacgt cgaaagccag     660
atcctcggcg acacccacgg caatgtcgtg catctcttcg agcgcgactg ttccgttcag     720
cgccgcaatc agaaggtcgt cgagcgcgcg cccgcaccct atctttcgga agcgcagcgc     780
caggaactcg ccgcctattc gctgaagatc gcaggggcga ccaactatat cggcgccggc     840
accgtcgaat atctgatgga tgccgatacc ggcaaatttt acttcatcga agtcaatccg     900
cgcatccagg tcgagcacac ggtgaccgaa gtcgtcaccg gcatcgatat cgtcaaggcg     960
cagatccaca tcctggacgg cgccgcgatc ggcacgccgc aatccggcgt gccgaaccag    1020
gaagacatcc gtctcaacgg tcacgccctg cagtgccgcg tgacgacgga agatccggag    1080
cacaacttca ttccggatta cggccgcatc accgccatc gctcggcttc cggcttcggc    1140
atccggcttg acggcggcac ctcttattcc ggcgccatca tcacccgcta ttacgatccg    1200
ctgctcgtca aggtcacggc ctgggcgccg aacccgctgg aagccatttc ccgcatggac    1260
cgggcgctgc gcgaattccg catccgtggc gtcgccacca acctgacctt cctcgaagcg    1320
atcatcggcc atccgaaatt ccgcgacaac agctacacca cccgcttcat cgacacgacg    1380
ccggagctct ccagcaggt caagcgccag gaccgcgcga cgaagcttct gacctatctc    1440
gccgacgtca ccgtcaatgg ccatcccgag gccaaggaca ggccgaagcc cctcgagaat    1500
gccgccaggc cggtggtgcc ctatgccaat ggcaacgggg tgaaggacgg caccaagcag    1560
ctgctcgata cgctcggccc gaaaaaattc ggcaatgatg tgcgcaatga aagcgcgtg    1620
cttctgaccg acaccacgat gcgcgacggc caccagtcgc tgctcgcaac ccgcatgcgt    1680
acctatgaca tcgccaggat cgccggcacc tattcgcatg cgctgccgaa cctcttgtcg    1740
ctcgaatgct ggggcggcgc caccttcgac gtctcgatgc gcttcctcac cgaagatccg    1800
tgggagcggc tggcgctgat ccgagagggg gcgccgaacc tgctcctgca gatgctgctg    1860
cgcggcgcca atggcgtcgg ttacaccaac tatcccgaca tgtcgtcaa atacttcgtc    1920
cgccaggcgg ccaaaggcgg catcgatctc ttccgcgtct tcgactgcct gaactgggtc    1980
gagaatatgc gggtgtcgat ggatgcgatt gccgaggaga caagctctg cgaggcggcg    2040
atctgctaca ccggcgatat cctcaattcc gcccgcccga atacgacttt gaaatattac    2100
accaaccttg ccgtcgagct tgagaaggcc ggcgcccata tcattgcggt caaggatatg    2160
gcgggccttc tgaagccggc tgctgccaag gttctgttca aggcgctgcg tgaagcaacc    2220
```

| | |
|---|---:|
| ggcctgccga tccatttcca cacgcatgac acctcgggca ttgcggcggc aacggttctt | 2280 |
| gccgccgtcg aagccggtgt cgatgccgtc gatgcggcga tggatgcgct ctccggcaac | 2340 |
| acctcgcaac cctgtctcgg ctcgatcgtc gaggcgctct ccggctccga gcgcgatccc | 2400 |
| ggcctcgatc cggcatggat ccgccgcatc tccttctatt gggaagcggt gcgcaaccag | 2460 |
| tatgccgcct tcgaaagcga cctcaaggga ccggcatcgg aagtctatct gcatgaaatg | 2520 |
| ccgggcggcc agttcaccaa cctcaaggag caggcccgct cgctgggggct ggaaacccgc | 2580 |
| tggcaccagg tggcgcaggc ctatgccgac gccaaccaga tgttcggcga tatcgtcaag | 2640 |
| gtgacgccat cctccaaggt cgtcggcgac atggcgctga tgatggtctc ccaggacctg | 2700 |
| accgtcgccg atgtcgtcag ccccgaccgc gaagtctcct tcccggaatc ggtcgtctcg | 2760 |
| atgctgaagg gcgatctcgg ccagcctccg tctggatggc cggaagcgct gcagaagaaa | 2820 |
| gcattgaagg gcgaaaagcc ctatacggtg cgccccggct cgctgctcaa ggaagccgat | 2880 |
| ctcgatgcgg aacgcaaagt catcgagaag aagcttgagc gcgaggtcag cgacttcgaa | 2940 |
| ttcgcttcct atctgatgta tccgaaggtc ttcaccgact ttgcgcttgc ctccgatacc | 3000 |
| tacggtccgg tttcggtgct gccgacgccc gcctattttt acgggttggc ggacggcgag | 3060 |
| gagctgttcg ccgacatcga aagggcaag acgctcgtca tcgtcaatca ggcggtgagc | 3120 |
| gccaccgaca gccagggcat ggtcactgtc ttcttcgagc tcaacggcca gccgcgccgt | 3180 |
| atcaaggtgc ccgatcgggc ccacggggcg acggagccgc ccgtgcgccg caaggccgaa | 3240 |
| cccggcaatg ccgcccatgt cggtgcgccg atgccgggcg tcatcagccg tgtctttgtc | 3300 |
| tcttcaggcc aggccgtcaa tgccggcgac gtgctcgtct ccatcgaggc catgaagatg | 3360 |
| gaaaccgcga tccatgcgga aaaggacggc accattgccg aagtgctggt caaggccggc | 3420 |
| gatcagatcg atgccaagga cctgctggcg gtttacggcg gatga | 3465 |

<210> SEQ ID NO 21
<211> LENGTH: 1305
<212> TYPE: DNA
<213> ORGANISM: Escherichia coli aceA

<400> SEQUENCE: 21

| | |
|---|---:|
| atgaaaaccc gtacacaaca aattgaagaa ttacagaaag agtggactca accgcgttgg | 60 |
| gaaggcatta ctcgcccata cagtgcggaa gatgtggtga attacgcgg ttcagtcaat | 120 |
| cctgaatgca cgctggcgca actgggcgca gcgaaaatgt ggcgtctgct gcacggtgag | 180 |
| tcgaaaaaag gctacatcaa cagcctcggc gcactgactg cggtcaggc gctgcaacag | 240 |
| gcgaaagcgg gtattgaagc agtctatctg tcgggatggc aggtagcggc ggacgctaac | 300 |
| ctggcggcca gcatgtatcc ggatcagtcg ctctatccgg caaactcggt gccagctgtg | 360 |
| gtggagcgga tcaacaacac cttccgtcgt gccgatcaga tccaatggtc cgcgggcatt | 420 |
| gagccgggcg atccgcgcta tgtcgattac ttcctgccga tcgttgccga tgcggaagcc | 480 |
| ggttttggcg gtgtcctgaa tgcctttgaa ctgatgaaag cgatgattga agccggtgca | 540 |
| gcggcagttc acttcgaaga tcagctggcg tcagtgaaga aatgcggtca catgggcggc | 600 |
| aaagttttag tgccaactca ggaagctatt cagaaactgg tcgcggcgcg tctgcagcgt | 660 |
| gacgtgacgg gcgttccaac cctgctggtt gcccgtaccg atgctgatgc ggcggatctg | 720 |
| atcacctccg attgcgaccc gtatgacagc gaatttatta ccggcgagcg taccagtgaa | 780 |
| ggcttcttcc gtactcatgc gggcattgag caagcgatca gccgtggcct ggcgtatgcg | 840 |
| ccatatgctg acctggtctg gtgtgaaacc tccacgccgg atctggaact ggcgcgtcgc | 900 |

-continued

```
tttgcacaag ctatccacgc gaaatatccg ggcaaactgc tggcttataa ctgctcgccg      960
tcgttcaact ggcagaaaaa cctcgacgac aaaactattg ccagcttcca gcagcagctg     1020
tcggatatgg gctacaagtt ccagttcatc accctggcag gtatccacag catgtggttc     1080
aacatgtttg acctggcaaa cgcctatgcc cagggcgagg gtatgaagca ctacgttgag     1140
aaagtgcagc agccggaatt tgccgccgcg aaagatggct ataccttcgt atctcaccag     1200
caggaagtgg gtacaggtta cttcgataaa gtgacgacta ttattcaggg cggcacgtct     1260
tcagtcaccg cgctgaccgg ctccactgaa gaatcgcagt tctaa                     1305
```

<210> SEQ ID NO 22
<211> LENGTH: 1284
<212> TYPE: DNA
<213> ORGANISM: Escherichia coli gltAR163L

<400> SEQUENCE: 22

```
atggctgata caaaagcaaa actcaccctc aacggggata cagctgttga actggatgtg      60
ctgaaaggca cgctgggtca agatgttatt gatatccgta ctctcggttc aaaaggtgtg     120
ttcacctttg acccaggctt cacttcaacc gcatcctgcg aatctaaaat tacttttatt     180
gatggtgatg aaggtatttt gctgcaccgc ggtttcccga tcgatcagct ggcgaccgat     240
tctaactacc tggaagtttg ttacatcctg ctgaatggtg aaaaaccgac tcaggaacag     300
tatgacgaat ttaaaactac ggtgacccgt cataccatga tccacgagca gattacccgt     360
ctgttccatg ctttccgtcg cgactcgcat ccaatggcag tcatgtgtgg tattaccggc     420
gcgctggcgg cgttctatca cgactcgctg gatgttaaca atcctcgtca ccgtgaaatt     480
gccgcgttcc tcctgctgtc gaaaatgccg actatggccg cgatgtgtta caagtattcc     540
attggtcagc catttgttta cccgcgcaac gatctctcct acgccggtaa cttcctgaat     600
atgatgttct ccacgccgtg cgaaccgtat gaagttaatc cgattctgga acgtgctatg     660
gaccgtattc tgatcctgca cgctgaccat gaacagaacg cctctacctc caccgtgcgt     720
accgctggct cttcgggtgc gaacccgttt gcctgtatcg cagcaggtat tgcttcactg     780
tggggacctg cgcacggcgg tgctaacgaa gcggcgctga aatgctgga agaaatcagc     840 tccgttaaac acattccgga atttgttcgt cgtgcgaaag acaaaaatga ttctttccgc     900
ctgatgggct tcggtcaccg cgtgtacaaa aattacgacc cgcgcgccac cgtaatgcgt     960
gaaacctgcc atgaagtgct gaaagagctg ggcacgaagg atgacctgct ggaagtggct    1020
atggagctgg aaaacatcgc gctgaacgac ccgtacttta tcgagaagaa actgtacccg    1080
aacgtcgatt tctactctgg tatcatcctg aaagcgatgg gtattccgtc ttccatgttc    1140
accgtcattt tcgcaatggc acgtaccgtt ggctggatcg cccactggag cgaaatgcac    1200
agtgacggta tgaagattgc ccgtccgcgt cagctgtata caggatatga aaacgcgac    1260 tttaaaagcg atatcaagcg ttaa                                           1284
```

<210> SEQ ID NO 23
<211> LENGTH: 939
<212> TYPE: DNA
<213> ORGANISM: Escherichia coli ghrA

<400> SEQUENCE: 23

```
atggatatca tcttttatca cccaacgttc gatacccaat ggtggattga ggcactgcgc      60
aaagctattc ctcaggcaag agtcagagca tggaaaagcg gagataatga ctctgctgat     120
```

```
tatgctttag tctggcatcc tcctgttgaa atgctggcag ggcgcgatct taaagcggtg      180
ttcgcactcg gggccggtgt tgattctatt ttgagcaagc tacaggcaca ccctgaaatg      240
ctgaacccct ctgttccact ttttcgcctg aagataccg gtatgggcga gcaaatgcag       300
gaatatgctg tcagtcaggt gctgcattgg tttcgacgtt ttgacgatta tcgcatccag      360
caaaatagtt cgcattggca accgctgcct gaatatcatc gggaagattt taccatcggc      420
attttgggcg caggcgtact gggcagtaaa gttgctcaga gtctgcaaac ctggcgcttt      480
ccgctgcgtt gctggagtcg aacccgtaaa tcgtggcctg gcgtgcaaag ctttgccgga      540
cgggaagaac tgtctgcatt tctgagccaa tgtcgggtat tgattaattt gttaccgaat      600
acccctgaaa ccgtcggcat tattaatcaa caattactcg aaaaattacc ggatggcgcg      660
tatctcctca acctggcgcg tggtgttcat gttgtggaag atgacctgct cgcggcgctg      720
gatagcggca agttaaagg cgcaatgttg gatgttttta atcgtgaacc cttaccgcct       780
gaaagtccgc tctggcaaca tccacgcgtg acgataacac cacatgtcgc cgcgattacc      840
cgtcccgctg aagctgtgga gtacatttct cgcaccattg cccagctcga aaagggggag      900 aggggtctgcg ggcaagtcga ccgcgcacgc ggctactaa                             939

<210> SEQ ID NO 24
<211> LENGTH: 7260
<212> TYPE: DNA
<213> ORGANISM: Artificial Sequence
<220> FEATURE:
<223> OTHER INFORMATION: J23119-pyc-aceA-gltAR163L-ghrA_synthetic_operon

<400> SEQUENCE: 24
ttgacagcta gctcagtcct aggtataatg ctagctaata gaaataattt tgtttaactt      60
taaggaggtt tggaggtacc atgcccatat ccaagatact cgttgccaat cgctctgaaa      120
tagccatccg cgtgttccgc gcggccaacg agcttggaat aaaaacggtg gcgatctggg      180
cggaagagga caagctggcg ctgcaccgct tcaaggcgga cgagagttat caggtcggcc      240
gcggaccgca tcttgcccgc gacctcgggc cgatcgaaag ctatctgtcg atcgacgagg      300
tgatccgcgt cgccaagctt tccggtgccg acgccatcca tccgggctac ggcctcttgt      360
cggaaagccc cgaattcgtc gatgcctgca caaggccgg catcatcttc atcggcccga      420
aggccgatac gatgcgccag cttggcaaca aggtcgcagc gcgcaacctg gcgatctcgg      480
tcggcgtacc ggtcgtgccg gcgaccgagc cactgccgga cgatatggcc gaagtggcga      540
agatggcggc ggcgatcggc tatcccgtca tgctgaaggc atcctgggc ggcggcggtc       600 gcggcatgcg cgtcattcgt tccgaggccg acctcgccaa ggaagtgacg gaagccaagc     660
gcgaggcgat ggcggccttc ggcaaggacg aggtctatct cgaaaaactg gtcgagcgcg      720
cccgccacgt cgaaagccag atcctcggcg acacccacgg caatgtcgtg catctcttcg      780
agcgcgactt ttccgttcag cgccgcaatc agaaggtcgt cgagcgcgcg cccgcaccct      840 atcttcgga agcgcagcgc caggaactcg ccgcctattc gctgaagatc gcaggggcga     900
ccaactatat cggcgccggc accgtcgaat atctgatgga tgccgatacc ggcaaatttt      960
acttcatcga agtcaatccg cgcatccagg tcgagcacac ggtgaccgaa gtcgtcaccg      1020
gcatcgatat cgtcaaggcg cagatccaca tcctggacgg cgccgcgatc ggcacgccgc      1080
aatccggcgt gccgaaccag gaagacatcg tctcaacgg tcacgccctg cagtgccgcg      1140
tgacgacgga agatccggag cacaacttca ttccggatta cggccgcatc accgccatc       1200 gctcggcttc cggcttcggc atccggcttg acggcggcac ctcttattcc ggcgccatca     1260
```

```
tcacccgcta ttacgatccg ctgctcgtca aggtcacggc ctgggcgccg aacccgctgg    1320
aagccatttc ccgcatggac cgggcgctgc gcgaattccg catccgtggc gtcgccacca    1380
acctgacctt cctcgaagcg atcatcggcc atccgaaatt ccgcgacaac agctacacca    1440
cccgcttcat cgacacgacg ccggagctct tccagcaggt caagcgccag accgcgcga    1500 cgaagcttct gacctatctc gccgacgtca ccgtcaatgg ccatcccgag gccaaggaca    1560
ggccgaagcc cctcgagaat gccgccaggc cggtggtgcc ctatgccaat ggcaacgggg    1620
tgaaggacgg caccaagcag ctgctcgata cgctcggccc gaaaaaattc ggcgaatgga    1680
tgcgcaatga agcgcgtg cttctgaccg acaccacgat gcgcgacggc caccagtcgc     1740
tgctcgcaac ccgcatgcgt acctatgaca tcgccaggat cgccggcacc tattcgcatg    1800
cgctgccgaa cctcttgtcg ctcgaatgct ggggcggcgc caccttcgac gtctcgatgc    1860
gcttcctcac cgaagatccg tgggagcggc tggcgctgat ccgagagggg gcgccgaacc    1920
tgctcctgca gatgctgctg cgcggcgcca atggcgtcgg ttacaccaac tatcccgaca    1980
atgtcgtcaa atacttcgtc cgccaggcgg ccaaaggcgg catcgatctc ttccgcgtct    2040
tcgactgcct gaactgggtc gagaatatgc gggtgtcgat ggatgcgatt gccgaggaga    2100
acaagctctg cgaggcggcg atctgctaca ccggcgatat cctcaattcc gcccgcccga    2160
aatacgactt gaaatattac accaaccttg ccgtcgagct tgagaaggcc ggcgcccata    2220
tcattgcggt caaggatatg gcgggccttc tgaagccggc tgctgccaag gttctgttca    2280
aggcgctgcg tgaagcaacc ggcctgccga tccatttcca cacgcatgac acctcgggca    2340
ttgcggcggc aacggttctt gccgccgtcg aagccggtgt cgatgccgtc gatgcggcga    2400
tggatgcgct ctccggcaac acctcgcaac cctgtctcgg ctcgatcgtc gaggcgctct    2460
ccggctccga gcgcgatccc ggcctcgatc cggcatggat ccgccgcatc tccttctatt    2520
gggaagcggt gcgcaaccag tatgccgcct tcgaaagcga cctcaaggga ccggcatcgg    2580
aagtctatct gcatgaaatg ccgggcggcc agttcaccaa cctcaaggag caggcccgct    2640
cgctggggct ggaaacccgc tggcaccagg tggcgcaggc ctatgccgac gccaaccaga    2700
tgttcggcga tatcgtcaag gtgacgccat cctccaaggt cgtcggcgac atggcgctga    2760
tgatggtctc ccaggacctg accgtcgccg atgtcgtcag ccccgaccgc gaagtctcct    2820
tcccggaatc ggtcgtctcg atgctgaagg gcgatctcgg ccagcctccg tctggatggc    2880
cggaagcgct gcagaagaaa gcattgaagg gcgaaaagcc ctatacggtg cgccccggct    2940
cgctgctcaa ggaagccgat ctcgatgcgg aacgcaaagt catcgagaag aagcttgagc    3000
gcgaggtcag cgacttcgaa ttcgcttcct atctgatgta ccgaaggtc ttcaccgact    3060 ttgcgcttgc ctccgatacc tacggtccgg tttcggtgct gccgacgccc gcctatttt    3120 acgggttggc ggacggcgag gagctgttcg ccgacatcga aagggcaag acgctcgtca    3180 tcgtcaatca ggcggtgagc gccaccgaca gccagggcat ggtcactgtc ttcttcgagc    3240
tcaacggcca gccgcgccgt atcaaggtgc ccgatcgggc ccacggggcg acgggagccg    3300
ccgtgcgccg caaggccgaa cccggcaatg ccgcccatgt cggtgcgccg atgccgggcg    3360
tcatcagccg tgtctttgtc tcttcaggcc aggccgtcaa tgccgcgac gtgctcgtct    3420 ccatcgaggc catgaagatg gaaaccgcga tccatgcgga aaaggacggc accattgccg    3480
aagtgctggt caaggccggc gatcagatcg atgccaagga cctgctggcg gtttacggcg    3540
gatgatctag aaggaggaac cgtatgaaaa cccgtacaca acaaattgaa gaattacaga    3600
```

```
aagagtggac tcaaccgcgt tgggaaggca ttactcgccc atacagtgcg aagatgtgg      3660 tgaaattacg cggttcagtc aatcctgaat gcacgctggc gcaactgggc gcagcgaaaa      3720
tgtggcgtct gctgcacggt gagtcgaaaa aaggctacat caacagcctc ggcgcactga      3780
ctggcggtca ggcgctgcaa caggcgaaag cgggtattga agcagtctat ctgtcgggat      3840
ggcaggtagc ggcggacgct aacctggcgg ccagcatgta tccggatcag tcgctctatc      3900
cggcaaactc ggtgccagct gtggtggagc ggatcaacaa caccttccgt cgtgccgatc      3960
agatccaatg gtccgcgggc attgagccgg gcgatccgcg ctatgtcgat tacttcctgc      4020
cgatcgttgc cgatgcggaa gccggttttg gcggtgtcct gaatgccttt gaactgatga      4080
aagcgatgat tgaagccggt gcagcggcag ttcacttcga agatcagctg gcgtcagtga      4140
agaaatgcgg tcacatgggc ggcaaagttt tagtgccaac tcaggaagct attcagaaac      4200
tggtcgcggc gcgtctggca gctgacgtga cgggcgttcc aaccctgctg gttgcccgta      4260
ccgatgctga tgcggcggat ctgatcacct ccgattgcga cccgtatgac agcgaattta      4320
ttaccggcga gcgtaccagt gaaggcttct tccgtactca tgcgggcatt gagcaagcga      4380
tcagccgtgg cctggcgtat gcgccatatg ctgacctggt ctggtgtgaa acctccacgc      4440
cggatctgga actggcgcgt cgcttttgcac aagctatcca cgcgaaatat ccgggcaaac      4500
tgctggctta taactgctcg ccgtcgttca actggcagaa aaacctcgac gacaaaacta      4560
ttgccagctt ccagcagcag ctgtcggata tgggctacaa gttccagttc atcaccctgg      4620
caggtatcca cagcatgtgg ttcaacatgt ttgacctggc aaacgcctat gcccagggcg      4680
agggtatgaa gcactacgtt gagaaagtgc agcagccgga atttgccgcc gcgaaagatg      4740
gctataccgt cgtatctcac cagcaggaag tgggtacagg ttacttcgat aaagtgacga      4800
ctattattca gggcggcacg tcttcagtca ccgcgctgac cggctccact gaagaatcgc      4860
agttctaaag gaggcacacg atggctgata caaaagcaaa actcacccct aacggggata      4920
cagctgttga actggatgtg ctgaaaggca cgctgggtca agatgttatt gatatccgta      4980
ctctcggttc aaaaggtgtg ttcacctttg acccaggctt cacttcaacc gcatcctgcg      5040
aatctaaaat tacttttatt gatggtgatg aaggtatttt gctgcaccgc ggtttcccga      5100
tcgatcagct ggcgaccgat tctaactacc tggaagtttg ttacatcctg ctgaatggtg      5160
aaaaaccgac tcaggaacag tatgacgaat ttaaaactac ggtgacccgt cataccatga      5220
tccacgagca gattacccgt ctgttccatg cttttcgtcg cgactcgcat ccaatggcag      5280
tcatgtgtgg tattaccggc gcgctggcgg cgttctatca cgactcgctg atgttaaca      5340 atcctcgtca ccgtgaaatt gccgcgttcc tcctgctgtc gaaaatgccg actatggccg      5400
cgatgtgtta caagtattcc attggtcagc catttgttta cccgcgcaac gatctctcct      5460
acgccggtaa cttcctgaat atgatgttct ccacgccgtg cgaaccgtat gaagttaatc      5520
cgattctgga acgtgctatg gaccgtattc tgatcctgca cgctgaccat gaacagaacg      5580
cctctacctc caccgtgcgt accgctggct cttcgggtgc gaacccgttt gcctgtatcg      5640
cagcaggtat tgcttcactg tggggacctg cgcacggcgg tgctaacgaa gcggcgctga      5700
aaatgctgga agaaatcagc tccgttaaac acattccgga atttgttcgt cgtgcgaaag      5760
acaaaaatga ttctttccgc ctgatgggct tcggtcaccg cgtgtacaaa aattacgacc      5820
cgcgcgccac cgtaatgcgt gaaacctgcc atgaagtgct gaagagctg gcacgaagg      5880 atgacctgct ggaagtggct atggagctgg aaaacatcgc gctgaacgac ccgtactta      5940 tcgagaagaa actgtacccg aacgtcgatt ctactctgg tatcatcctg aaagcgatgg      6000
```

```
gtattccgtc ttccatgttc accgtcattt tcgcaatggc acgtaccgtt ggctggatcg    6060
cccactggag cgaaatgcac agtgacggta tgaagattgc ccgtccgcgt cagctgtata    6120
caggatatga aaacgcgac tttaaaagcg atatcaagcg ttaaaggagg cacacgatgg     6180
atatcatctt ttatcaccca acgttcgata cccaatggtg gattgaggca ctgcgcaaag    6240
ctattcctca ggcaagagtc agagcatgga aaagcggaga taatgactct gctgattatg    6300
ctttagtctg gcatcctcct gttgaaatgc tggcagggcg cgatcttaaa gcggtgttcg    6360
cactcggggc cggtgttgat tctattttga gcaagctaca ggcacaccct gaaatgctga    6420
acccttctgt tccacttttt cgcctggaag ataccggtat gggcgagcaa atgcaggaat    6480
atgctgtcag tcaggtgctg cattggtttc gacgttttga cgattatcgc atccagcaaa    6540
atagttcgca ttggcaaccg ctgcctgaat atcatcggga agattttacc atcggcattt    6600
tgggcgcagg cgtactgggc agtaaagttg ctcagagtct gcaaacctgg cgctttccgc    6660
tgcgttgctg gagtcgaacc cgtaaatcgt ggcctggcgt gcaaagcttt gccggacggg    6720
aagaactgtc tgcatttctg agccaatgtc gggtattgat taatttgtta ccgaataccc    6780
ctgaaaccgt cggcattatt aatcaacaat tactcgaaaa attaccggat ggcgcgtatc    6840
tcctcaacct ggcgcgtggt gttcatgttg tggaagatga cctgctcgcg cgctggata    6900 gcggcaaagt taaaggcgca atgttggatg ttttaatcg tgaaccctta ccgcctgaaa    6960
gtccgctctg caacatcca cgcgtgacga taacaccaca tgtcgccgcg attcccgtc     7020 ccgctgaagc tgtggagtac atttctcgca ccattgccca gctcgaaaaa ggggagaggg    7080
tctgcgggca agtcgaccgc gcacgcggct actaatctat gatatcgaat tcctgcagcc    7140
cgggggatcc catggtacgc gtgctagagg catcaaataa aacgaaaggc tcagtcgaaa    7200
gactgggcct ttcgttttat ctgttgtttg tcggtgaacg ctctcctgag taggacaaat    7260
```

<210> SEQ ID NO 25
<211> LENGTH: 260
<212> TYPE: DNA
<213> ORGANISM: Artificial Sequence
<220> FEATURE:
<223> OTHER INFORMATION: Ptac_promoter_from_pACT3

<400> SEQUENCE: 25

```
cggagcttat cgactgcacg gtgcaccaat gcttctggcg tcaggcagcc atcggaagct     60
gtggtatggc tgtgcaggtc gtaaatcact gcataattcg tgtcgctcaa ggcgcactcc    120
cgttctggat aatgtttttt cgccgacat cataacggtt ctggcaaata ttctgaaatg     180
agctgttgac aattaatcat cggctcgtat aatgtgtgga attgtgagcg ataacaatt     240 tcacacagga aacagaattc                                                260
```

<210> SEQ ID NO 26
<211> LENGTH: 2123
<212> TYPE: DNA
<213> ORGANISM: Artificial Sequence
<220> FEATURE:
<223> OTHER INFORMATION: sucCD_Methylococcus_capsulatus_str_Bath

<400> SEQUENCE: 26

```
gaattcctat aatttttgttt aactttaagg aggggtacca tgaatatcca tgagtaccag     60
gccaaggagc tgctcaagac ctatggcgtg cccgtgcccg acggcgccgt tgcctattcc    120
gacgcgcagg ccgccagcgt cgccgaggag atcggcggca gccgctgggt ggtcaaggcg    180
```

```
cagatccatg ccggcggtcg cggcaaggcc gggggcgtaa aggtcgccca ctccatcgag      240
gaagtccgcc aatacgccga cgccatgctc ggcagccacc tcgtcaccca tcagaccggc      300
ccgggaggct cgctggttca gcgtctgtgg gtggaacagg ccagccatat caaaaaggaa      360
tactacctgg gcttcgtgat cgatcgcggc aatcaacgca tcaccctgat cgcctccagc      420
gagggcggca tggaaatcga ggaagtcgca aaggaaaccc cggagaaaat cgtcaaggaa      480
gtcgtcgatc cggccatagg cctgctggac ttccagtgcc gcaaggtcgc cacgcgcgatc     540
ggcctgaaag gcaaactgat gccccaggcc gtcaggctga tgaaggccat ctaccgctgc      600
atgcgcgaca agatgcccct gcaggccgaa atcaatcctc tggccatcgt gggcgaaagc      660
gacgaatcgc tcatggtcct ggatgccaag ttcaacttcg acgacaacgc cctgtaccgg      720
cagcgcacca tcaccgagat gcgcgacctg gccgaggaag acccgaaaga ggtcgaagcc      780
tccggccacg gtctcaatta catcgccctc gacggcaaca tcggctgcat cgtcaatggc      840
gccggcctcg ccatggcttc gctcgacgcc atcaccctgc atggcggccg tccggccaac      900
ttcctcgacg tgggcggcgg cgcctccccc gagaaggtca ccaatgcctg ccgcatcgta      960
ctggaagatc ccaacgtccg ctgcatcctg tcaacatct tgccggcat caaccgctgt       1020
gactggatcg ccaagggcct gatccaggcc tgcgacagcc tgcagatcaa ggtgccgctg     1080
atcgtgcgcc tggccgggac gaacgtcgac gagggccgca agatcctggc cgaatccggc     1140
ctctccttca tcaccgcgga aaatctggac gacgcggccg ccaaggccgt cgccatcgtc     1200
aagggataac agtcatgagc gtattcgtta acaagcactc caaggtcatc ttccagggct     1260
tcaccggcga gcacgccacc ttccacgcca aggacgccat gcggatgggc acccgggtgg     1320
tcggcggtgt caccctggc aaaggcggca cccgccatcc cgatcccgaa ctcgctcatc      1380
tgccggtgtt cgacaccgtg gctgaagccg tggccgccac cggcgccgac gtctccgccg     1440
tgttcgtgcc gccgcccttc aatgcggacg cgttgatgga agccatagac gccggcatcc     1500
gggtcgccgt gaccatcgcc gacggcatcc cggtacacga catgatccga ctgcagcgct     1560
accgggtggg taaggattcc atcgtgatcg accgaacac ccccggcatc atcacgccgg      1620
gcgagtgcaa ggtgggcatc atgccttcgc acatttacaa gaagggcaac gtcggcatcg     1680
tgtcgcgctc cggcacccte aattacgagg cgacggaaca gatggccgcg cttgggctgg     1740
gcatcaccac ctcggtcggt atcggcggtg accccatcaa cggaaccgat ttcgtcactg     1800
tcctgcgcgc cttcgaagcc gacccggaaa ccgagatcgt ggtgatgatc ggcgaaatcg     1860
gcggcccccca ggaagtcgcc gccgcccgct gggccaagga aaacatgaca aagccggtca     1920
tcggcttcgt cgcaggcctt gccgcaccga ccggccgacg catgggccat gccggcgcca     1980
tcatctccag cgaggccgac accgccgag ccaagatgga cgccatgaa gccttggggc       2040
tgtatgtcgc ccgcaacccg gcacagatcg gccagaccgt gctacgcgcc gcgcaggaac     2100
acggaatcag attctgatct aga                                             2123
```

<210> SEQ ID NO 27
<211> LENGTH: 975
<212> TYPE: DNA
<213> ORGANISM: Artificial Sequence
<220> FEATURE:
<223> OTHER INFORMATION: mcl_ Methylobacterium_extorquens_AM1

<400> SEQUENCE: 27

```
atgagcttca ccctgatcca gcaggccacc ccgcgcctgc accgctcgga actcgcggtt       60
cccggctcca acccgacctt catggagaag tcggccgcct cgaaggccga cgtgatcttc      120
```

-continued

```
ctcgacctcg aggacgcggt tgcgcccgac gacaaggagc aggcccgcaa gaacatcatc    180
caggccctca acgacctgga ttggggcaac aagaccatga tgatccgcat caacggtctc    240 gacaccccact acatgtaccg cgacgtggtg gacatcgtgg aggcctgccc gcgcctcgac   300
atgatcctga tccccaaggt cggcgtgccg gccgacgtct acgccatcga cgtgctgacg    360
acgcagatcg agcaggccaa gaagcgcgag aagaagatcg gcttcgaggt gctgatcgag    420
accgcgctcg gcatggccaa tgtcgaggcg atcgcgacct cgtctaagcg ccttgaggcg    480
atgtccttcg gtgtcgccga ctacgccgct ccacccgcg cccgctccac cgtgatcggc     540
ggcgtcaacg ccgattacag cgtgctcacc gacaaggacg aggccggcaa ccgccagacc    600
cactggcagg atccgtggct gttcgcccag aaccgcatgc tggtcgcctg ccgcgcctac    660
ggcctgcgcc cgatcgacgg tcccttcggc gacttctccg atccggacgg ctacacctcg    720
gccgctcgcc gctgcgccgc gctcggcttc gagggcaagt gggcgatcca cccctcgcag    780
atcgatctcg ccaacgaggt cttcaccccc tccgaggccg aggtcaccaa ggcccgccgc    840
atcctggaag ccatggaaga ggccgccaag gccggccgcg cgccgtctc gctcgacggc      900 cgtctcatcg acatcgcctc gatccgcatg gccgaggcgc tgatccagaa ggccgacgcg    960
atgggcggaa agtaa                                                     975
```

<210> SEQ ID NO 28  
<211> LENGTH: 3489  
<212> TYPE: DNA  
<213> ORGANISM: Artificial Sequence  
<220> FEATURE:  
<223> OTHER INFORMATION: Ptac_sucC_sucD_mcl_synthetic_operon

<400> SEQUENCE: 28

```
cggagcttat cgactgcacg gtgcaccaat gcttctggcg tcaggcagcc atcggaagct     60
gtggtatggc tgtgcaggtc gtaaatcact gcataattcg tgtcgctcaa ggcgcactcc    120
cgttctggat aatgtttttt gcgccgacat cataacggtt ctggcaaata ttctgaaatg    180
agctgttgac aattaatcat cggctcgtat aatgtgtgga attgtgagcg gataacaatt    240
tcacacagga aacagaattc ctataatttt gtttaacttt aaggagggggt accatgaata    300 tccatgagta ccaggccaag gagctgctca agacctatgg cgtgcccgtg ccgacggcg     360 ccgttgccta ttccgacgcg caggccgcca gcgtcgccga ggagatcggc ggcagccgct    420
gggtggtcaa ggcgcagatc catgccggcg gtcgcggcaa ggccggggc gtaaaggtcg     480 cccactccat cgaggaagtc cgccaatacg ccgacgccat gctcggcagc cacctcgtca    540
cccatcagac cggcccggga ggctcgctgg ttcagcgtct gtgggtggaa caggccagcc    600
atatcaaaaa ggaatactac ctgggcttcg tgatcgatcg cggcaatcaa cgcatcaccc    660
tgatcgcctc cagcgagggc ggcatggaaa tcgaggaagt cgcaaaggaa accccggaga    720
aaatcgtcaa ggaagtcgtc gatccggcca taggcctgct ggacttccag tgccgcaagg    780
tcgccacggc gatcggcctg aaaggcaaac tgatgcccca ggccgtcagg ctgatgaagg    840
ccatctaccg ctgcatgcgc gacaaagatg ccctgcaggc cgaaatcaat cctctggcca    900
tcgtgggcga aagcgacgaa tcgctcatgg tcctggatgc caagttcaac ttcgacgaca    960
acgccctgta ccggcagcgc accatcaccg agatgcgcga cctggccgag gaagacccga   1020
aagaggtcga agcctccggc cacgtgctca attacatcgc cctcgacggc aacatcggct   1080
gcatcgtcaa tggcgccggc ctcgccatgg cttcgctcga cgccatcacc ctgcatggcg   1140
```

-continued

```
gccgtccggc caacttcctc gacgtgggcg gcggcgcctc ccccgagaag gtcaccaatg      1200
cctgccgcat cgtactggaa gatcccaacg tccgctgcat cctggtcaac atctttgccg      1260
gcatcaaccg ctgtgactgg atcgccaagg gcctgatcca ggcctgcgac agcctgcaga      1320
tcaaggtgcc gctgatcgtg cgcctggccg ggacgaacgt cgacgagggc cgcaagatcc      1380
tggccgaatc cggcctctcc ttcatcaccg cggaaaatct ggacgacgcg ccgccaagg       1440
ccgtcgccat cgtcaaggga taacagtcat gagcgtattc gttaacaagc actccaaggt      1500
catcttccag ggcttcaccg gcgagcacgc caccttccac gccaaggacg ccatgcggat      1560
gggcacccgg gtggtcggcg gtgtcacccc tggcaaaggc ggcacccgcc atcccgatcc      1620
cgaactcgct catctgccgg tgttcgacac cgtggctgaa gccgtggccg ccaccggcgc      1680
cgacgtctcc gccgtgttcg tgccgccgcc cttcaatgcg gacgcgttga tggaagccat      1740
agacgccggc atccgggtcg ccgtgaccat cgccgacggc atcccggtac acgacatgat      1800
ccgactgcag cgctaccggg tgggtaagga ttccatcgtg atcggaccga acaccccgg       1860
catcatcacg ccgggcgagt gcaaggtggg catcatgcct tcgcacattt acaagaaggg      1920
caacgtcggc atcgtgtcgc gctccggcac cctcaattac gaggcgacgg aacagatggc      1980
cgcgcttggg ctgggcatca ccacctcggt cggtatcggg ggtgacccca tcaacggaac      2040
cgatttcgtc actgtcctgc gcgccttcga agccgacccg gaaaccgaga tcgtggtgat      2100
gatcggcgaa atcggcggcc cccaggaagt cgccgccgcc cgctgggcca aggaaaacat      2160
gacaaagccg gtcatcggct tcgtcgcagg ccttgccgca ccgaccggcc gacgcatggg      2220
ccatgccggc gccatcatct ccagcgaggc cgacaccgcc ggagccaaga tggacgccat      2280
ggaagccttg gggctgtatg tcgcccgcaa cccggcacag atcggccaga ccgtgctacg      2340
cgccgcgcag gaacacggaa tcagattctg atctagacta taattttgtt taactttaag      2400
gaggtttgga atgagcttca ccctgatcca gcaggccacc ccgcgcctgc accgctcgga      2460
actcgcggtt cccggctcca acccgacctt catggagaag tcggccgcct cgaaggccga      2520
cgtgatcttc ctcgacctcg aggacgcggt tgcgcccgac gacaaggagc aggcccgcaa      2580
gaacatcatc caggccctca acgacctgga ttggggcaac aagaccatga tgatccgcat      2640
caacggtctc gacacccact acatgtaccg cgacgtggtg gacatcgtgg aggcctgccc      2700
gcgcctcgac atgatcctga tccccaaggt cggcgtgccg gccgacgtct acgccatcga      2760
cgtgctgacg acgcagatcg agcaggccaa gaagcgcgag aagaagatcg gcttcgaggt      2820
gctgatcgag accgcgctcg gcatggccaa tgtcgaggcg atcgcgacct cgtctaagcg      2880
ccttgaggcg atgtccttcg gtgtcgccga ctacgccgct tccacccgcg cccgctccac      2940
cgtgatcggc ggcgtcaacg ccgattacag cgtgctcacc gacaaggacg aggccggcaa      3000
ccgccagacc cactggcagg atccgtggct gttcgcccag aaccgcatgc tggtcgcctg      3060
ccgcgcctac ggcctgcgcc cgatcgacgg tccttcggc gacttctccg atccggacgg       3120
ctacacctcg gccgctcgcc gctgcgccgc gctcggcttc gagggcaagt gggcgatcca      3180
cccctcgcag atcgatctcg ccaacgaggt cttcacccc tccgaggccg aggtcaccaa       3240
ggcccgccgc atcctggaag ccatggaaga ggccgccaag gccggccgcg gcgccgtctc      3300
gctcgacggc cgtctcatcg acatcgcctc gatccgcatg gccgaggcgc tgatccagaa      3360
ggccgacgcg atgggcggaa agtaaacgcg tgctagaggc atcaaataaa acgaaaggct      3420
cagtcgaaag actgggcctt tcgttttatc tgttgtttgt cggtgaacgc tctcctgagt      3480
aggacaaat                                                              3489
```

<210> SEQ ID NO 29
<211> LENGTH: 2652
<212> TYPE: DNA
<213> ORGANISM: Escherichia coli ppcK620S

<400> SEQUENCE: 29

| | | | | | | |
|---|---|---|---|---|---|---|
| atgaacgaac | aatattccgc | attgcgtagt | aatgtcagta | tgctcggcaa | agtgctggga | 60 |
| gaaaccatca | aggatgcgtt | gggagaacac | attcttgaac | gcgtagaaac | tatccgtaag | 120 |
| ttgtcgaaat | cttcacgcgc | tggcaatgat | gctaaccgcc | aggagttgct | caccacctta | 180 |
| caaaatttgt | cgaacgacga | gctgctgccc | gttgcgcgtg | cgtttagtca | gttcctgaac | 240 |
| ctggccaaca | ccgccgagca | ataccacagc | atttcgccga | aggcgaagc | tgccagcaac | 300 |
| ccggaagtga | tcgcccgcac | cctgcgtaaa | ctgaaaaacc | agccggaact | gagcgaagac | 360 |
| accatcaaaa | aagcagtgga | atcgctgtcg | ctggaactgg | tcctcacggc | tcacccaacc | 420 |
| gaaattaccc | gtcgtacact | gatccacaaa | atggtggaag | tgaacgcctg | tttaaaacag | 480 |
| ctcgataaca | aagatatcgc | tgactacgaa | cacaaccagc | tgatgcgtcg | cctgcgccag | 540 |
| ttgatcgccc | agtcatggca | taccgatgaa | atccgtaagc | tgcgtccaag | cccggtagat | 600 |
| gaagccaaat | ggggctttgc | cgtagtggaa | aacagcctgt | ggcaaggcgt | accaaattac | 660 |
| ctgcgcgaac | tgaacgaaca | actggaagag | aacctcggct | acaaactgcc | cgtcgaattt | 720 |
| gttccggtcc | gttttacttc | gtggatgggc | ggcgaccgcg | acggcaaccc | gaacgtcact | 780 |
| gccgatatca | cccgccacgt | cctgctactc | agccgctgga | agccaccga | tttgttcctg | 840 |
| aaagatattc | aggtgctggt | ttctgaactg | tcgatggttg | aagcgacccc | tgaactgctg | 900 |
| gcgctggttg | gcgaagaagg | tgccgcagaa | ccgtatcgct | atctgatgaa | aaacctgcgt | 960 |
| tctcgcctga | tggcgacaca | ggcatggctg | gaagcgcgcc | tgaaaggcga | agaactgcca | 1020 |
| aaaccagaag | gcctgctgac | acaaaacgaa | gaactgtggg | aaccgctcta | cgcttgctac | 1080 |
| cagtcacttc | aggcgtgtgg | catgggtatt | atcgccaacg | gcgatctgct | cgacaccctg | 1140 |
| cgccgcgtga | atgtttcgg | cgtaccgctg | gtccgtattg | atatccgtca | ggagagcacg | 1200 |
| cgtcataccg | aagcgctggg | cgagctgacc | cgctacctcg | gtatcggcga | ctacgaaagc | 1260 |
| tggtcagagg | ccgacaaaca | ggcgttcctg | atccgcgaac | tgaactccaa | acgtccgctt | 1320 |
| ctgccgcgca | actggcaacc | aagcgccgaa | acgcgcgaag | tgctcgatac | ctgccaggtg | 1380 |
| attgccgaag | caccgcaagg | ctccattgcc | gcctacgtga | tctcgatggc | gaaaacgccg | 1440 |
| tccgacgtac | tggctgtcca | cctgctgctg | aaagaagcgg | gtatcgggtt | tgcgatgccg | 1500 |
| gttgctccgc | tgtttgaaac | cctcgatgat | ctgaacaacg | ccaacgatgt | catgacccag | 1560 |
| ctgctcaata | ttgactggta | tcgtggcctg | attcagggca | aacagatggt | gatgattggc | 1620 |
| tattccgact | cagcaaaaga | tgcgggagtg | atggcagctt | cctgggcgca | atatcaggca | 1680 |
| caggatgcat | taatcaaaac | ctgcgaaaaa | gcgggtattg | agctgacgtt | gttccacggt | 1740 |
| cgcggcggtt | ccattggtcg | cggcggcgca | cctgctcatg | cggcgctgct | gtcacaaccg | 1800 |
| ccaggaagcc | tgaaaggcgg | cctgcgcgta | accgaacagg | gcgagatgat | ccgctttagc | 1860 |
| tatggtctgc | cagaaatcac | cgtcagcagc | ctgtcgcttt | ataccggggc | gattctggaa | 1920 |
| gccaacctgc | tgccaccgcc | ggagccgaaa | gagagctggc | gtcgcattat | ggatgaactg | 1980 |
| tcagtcatct | cctgcgatgt | ctaccgcggc | tacgtacgtg | aaaacaaaga | ttttgtgcct | 2040 |
| tacttccgct | ccgctacgcc | ggaacaagaa | ctgggcaaac | tgccgttggg | ttcacgtccg | 2100 |

```
gcgaaacgtc gcccaaccgg cggcgtcgag tcactacgcg ccattccgtg gatcttcgcc    2160
tggacgcaaa accgtctgat gctccccgcc tggctgggtg caggtacggc gctgcaaaaa    2220
gtggtcgaag acggcaaaca gagcgagctg gaggctatgt gccgcgattg ccattcttc     2280 tcgacgcgtc tcggcatgct ggagatggtc ttcgccaaag cagacctgtg gctggcggaa    2340
tactatgacc aacgcctggt agacaaagca ctgtggccgt taggtaaaga gttacgcaac    2400
ctgcaagaag aagacatcaa agtggtgctg gcgattgcca acgattccca tctgatggcc    2460
gatctgccgt ggattgcaga gtctattcag ctacggaata tttacaccga cccgctgaac    2520
gtattgcagg ccgagttgct gcaccgctcc cgccaggcag aaaagaaggg ccaggaaccg    2580
gatcctcgcg tcgaacaagc gttaatggtc actattgccg ggattgcggc aggtatgcgt    2640
aataccggct aa                                                        2652

<210> SEQ ID NO 30
<211> LENGTH: 6602
<212> TYPE: DNA
<213> ORGANISM: Artificial Sequence
<220> FEATURE:
<223> OTHER INFORMATION: Ptac- ppcK620S-aceA-gltAR163L-ghrA_synthetic_
      operon

<400> SEQUENCE: 30
cggagcttat cgactgcacg gtgcaccaat gcttctggcg tcaggcagcc atcggaagct     60
gtggtatggc tgtgcaggtc gtaaatcact gcataattcg tgtcgctcaa ggcgcactcc    120
cgttctggat aatgtttttt gcgccgacat cataacggtt ctgcaaaata ttctgaaatg    180
agctgttgac aattaatcat cggctcgtat aatgtgtgga attgtgagcg gataacaatt    240
tcacacagga acagaattc gagctcggta cccgggatga cgaacaata ttccgcattg      300 cgtagtaatg tcagtatgct cggcaaagtg ctgggagaaa ccatcaagga tgcgttggga    360
gaacacattc ttgaacgcgt agaaactatc cgtaagttgt cgaaatcttc acgcgctggc    420
aatgatgcta accgccagga gttgctcacc accttacaaa atttgtcgaa cgacgagctg    480
ctgcccgttg cgcgtgcgtt tagtcagttc ctgaacctgg ccaacaccgc cgagcaatac    540
cacagcattt cgccgaaagg cgaagctgcc agcaacccgg aagtgatcgc ccgcaccctg    600
cgtaaactga aaaccagcc ggaactgagc gaagacacca tcaaaaaagc agtggaatcg    660
ctgtcgctgg aactggtcct cacggctcac ccaaccgaaa ttacccgtcg tacactgatc    720
cacaaaatgg tggaagtgaa cgcctgtttta aaacagctcg ataacaaaga tatcgctgac    780
tacgaacaca accagctgat gcgtcgcctg cgccagttga tcgcccagtc atggcatacc    840
gatgaaatcc gtaagctgcg tccaagcccg gtagatgaag ccaaatgggg ctttgccgta    900
gtggaaaaca gcctgtggca aggcgtacca aattacctgc gcgaactgaa cgaacaactg    960
gaagagaacc tcggctacaa actgcccgtc gaatttgttc cggtccgttt tacttcgtgg    1020
atgggcggcg accgcgacgg caacccgaac gtcactgccg atatcacccg ccacgtcctg    1080
ctactcagcc gctggaaagc caccgatttg ttcctgaaag atattcaggt gctggtttct    1140
gaactgtcga tggttgaagc gaccccctgaa ctgctggcgc tggttggcga agaaggtgcc    1200
gcagaaccgt atcgctatct gatgaaaaac ctgcgttctc gcctgatggc gacacaggca    1260
tggctggaag cgcgcctgaa aggcgaagaa ctgccaaaaac cagaaggcct gctgacacaa    1320
aacgaagaac tgtgggaacc gctctacgct tgctaccagt cacttcaggc gtgtggcatg    1380
ggtattatcg ccaacggcga tctgctcgac accctgcgcc gcgtgaaatg tttcggcgta    1440
```

```
ccgctggtcc gtattgatat ccgtcaggag agcacgcgtc ataccgaagc gctgggcgag   1500
ctgacccgct acctcggtat cggcgactac gaaagctggt cagaggccga caaacaggcg   1560
ttcctgatcc gcgaactgaa ctccaaacgt ccgcttctgc cgcgcaactg caaccaagc    1620
gccgaaacgc gcgaagtgct cgatacctgc caggtgattg ccgaagcacc gcaaggctcc   1680
attgccgcct acgtgatctc gatggcgaaa acgccgtccg acgtactggc tgtccacctg   1740
ctgctgaaag aagcgggtat cgggtttgcg atgccggttg ctccgctgtt tgaaaccctc   1800
gatgatctga caacgccaa cgatgtcatg acccagctgc tcaatattga ctggtatcgt    1860
ggcctgattc agggcaaaca gatggtgatg attggctatt ccgactcagc aaaagatgcg   1920
ggagtgatgg cagcttcctg gcgcaatat caggcacagg atgcattaat caaaacctgc    1980
gaaaaagcgg gtattgagct gacgttgttc cacggtcgcg gcggttccat tggtcgcggc   2040
ggcgcacctg ctcatgcggc gctgctgtca caaccgccag gaagcctgaa aggcggcctg   2100
cgcgtaaccg aacagggcga gatgatccgc tttagctatg gtctgccaga aatcaccgtc   2160
agcagcctgt cgctttatac cggggcgatt ctggaagcca acctgctgcc accgccggag   2220
ccgaaagaga gctggcgtcg cattatggat gaactgtcag tcatctcctg cgatgtctac   2280
cgcggctacg tacgtgaaaa caaagatttt gtgccttact ccgctccgc tacgccggaa    2340
caagaactgg gcaaactgcc gttgggttca cgtccggcga acgtcgccc aaccggcggc    2400
gtcgagtcac tacgcgccat tccgtggatc ttcgcctgga cgcaaaaccg tctgatgctc   2460
cccgcctggc tgggtgcagg tacggcgctg caaaaagtgg tcgaagacgg caaacagagc   2520
gagctggagg ctatgtgccg cgattggcca ttcttctcga cgcgtctcgg catgctggag   2580
atggtcttcg ccaaagcaga cctgtggctg gcggaatact atgaccaacg cctggtagac   2640
aaagcactgt ggccgttagg taaagagtta cgcaacctgc aagaagaaga catcaaagtg   2700
gtgctggcga ttgccaacga ttcccatctg atggccgatc tgccgtggat tgcagagtct   2760
attcagctac ggaatattta caccgacccg ctgaacgtat gcaggccga gttgctgcac    2820
cgctcccgcc aggcagaaaa agaaggccag gaaccggatc ctcgcgtcga caagcgtta    2880
atggtcacta ttgccgggat tgcggcaggt atgcgtaata ccggctaatc tagaaggagg   2940
aaccgtatga aaacccgtac acaacaaatt gaagaattac agaaagagtg gactcaaccg   3000
cgttgggaag gcattactcg cccatacagt gcggaagatg tggtgaaatt acgcggttca   3060
gtcaatcctg aatgcacgct ggcgcaactg ggcgcagcga aaatgtggcg tctgctgcac   3120
ggtgagtcga aaaaaggcta catcaacagc ctcggcgcac tgactggcgg tcaggcgctg   3180
caacaggcga agcgggtat tgaagcagtc tatctgtcgg gatggcaggt agcggcggac    3240
gctaacctgg cggccagcat gtatccggat cagtcgctct atccggcaaa ctcggtgcca   3300
gctgtggtgg agcggatcaa caacaccttc cgtcgtgccg atcagatcca atggtccgcg   3360
ggcattgagc cgggcgatcc gcgctatgtc gattacttcc tgccgatcgt tgccgatgcg   3420
gaagccggtt ttggcggtgt cctgaatgcc tttgaactga tgaaagcgat gattgaagcc   3480
ggtgcagcgg cagttcactt cgaagatcag ctggcgtcag tgaagaaatg cggtcacatg   3540
ggcggcaaag ttttagtgcc aactcaggaa gctattcaga actggtcgc ggcgcgtctg    3600
gcagctgacg tgacgggcgt tccaaccctg ctggttgccc gtaccgatgc tgatgcggcg   3660
gatctgatca cctccgattg cgacccgtat gacagcgaat ttattaccgg cgagcgtacc   3720
agtgaaggct tcttccgtac tcatgcgggc attgagcaag cgatcagccg tggcctggcg   3780
tatgcgccat atgctgacct ggtctggtgt gaaacctcca cgccggatct ggaactggcg   3840
```

```
cgtcgctttg cacaagctat ccacgcgaaa atatccgggca aactgctggc ttataactgc   3900
tcgccgtcgt tcaactggca gaaaaacctc gacgacaaaa ctattgccag cttccagcag   3960
cagctgtcgg atatgggcta caagttccag ttcatcaccc tggcaggtat ccacagcatg   4020
tggttcaaca tgtttgacct ggcaaacgcc tatgcccagg gcgagggtat gaagcactac   4080
gttgagaaag tgcagcagcc ggaatttgcc gccgcgaaag atggctatac cttcgtatct   4140
caccagcagg aagtgggtac aggttacttc gataaagtga cgactattat tcagggcggc   4200
acgtcttcag tcaccgcgct gaccggctcc actgaagaat cgcagttcta aggaggcac    4260 acgatggctg atacaaaagc aaaactcacc ctcaacgggg atacagctgt tgaactggat   4320
gtgctgaaag gcacgctggg tcaagatgtt attgatatcc gtactctcgg ttcaaaaggt   4380
gtgttcaccT ttgacccagg cttcacttca accgcatcct gcgaatctaa aattactttt   4440
attgatggtg atgaaggtat tttgctgcac cgcggtttcc cgatcgatca gctggcgacc   4500
gattctaact acctggaagt tgttacatc ctgctgaatg gtgaaaaacc gactcaggaa    4560
cagtatgacg aatttaaaac tacggtgacc cgtcataccA tgatccacga gcagattacc   4620
cgtctgttcc atgctttccg tcgcgactcg catccaatgg cagtcatgtg tggtattacc   4680
ggcgcgctgg cggcgttcta tcacgactcg ctggatgtta acaatcctcg tcaccgtgaa   4740
attgccgcgt tcctcctgct gtcgaaaatg ccgactatgg ccgcgatgtg ttacaagtat   4800
tccattggtc agccatttgt ttacccgcgc aacgatctct cctacgccgg taacttcctg   4860
aatatgatgt tctccacgcc gtgcgaaccg tatgaagtta atccgattct ggaacgtgct   4920
atggaccgta ttctgatcct gcacgctgac catgaacaga acgcctctac ctccaccgtg   4980
cgtaccgctg gctcttcggg tgcgaacccg tttgcctgta tcgcagcagg tattgcttca   5040
ctgtggggac ctgcgcacgg cggtgctaac gaagcggcgc tgaaaatgct ggaagaaatc   5100
agctccgtta aacacattcc ggaatttgtt cgtcgtgcga aagacaaaaa tgattctttc   5160
cgcctgatgg gcttcggtca ccgcgtgtac aaaaattacg acccgcgcgc caccgtaatg   5220
cgtgaaacct gccatgaagt gctgaaagag ctgggcacga aggatgacct gctggaagtg   5280
gctatggagc tggaaaacat cgcgctgaac gacccgtact ttatcgagaa gaaactgtac   5340
ccgaacgtcg atttctactc tggtatcatc ctgaaagcga tgggtattcc gtcttccatg   5400
ttcaccgtca ttttcgcaat ggcacgtacc gttggctgga tcgcccactg gagcgaaatg   5460
cacagtgacg gtatgaagat tgcccgtccg cgtcagctgt atacaggata tgaaaaacgc   5520
gactttaaaa gcgatatcaa gcgttaaagg aggcacacga tggatatcat cttttatcac   5580
ccaacgttcg ataccaaatg gtggattgag gcactgcgca aagctattcc tcaggcaaga   5640
gtcagagcat ggaaaagcgg agataatgac tctgctgatt atgctttagt ctggcatcct   5700
cctgttgaaa tgctggcagg gcgcgatctt aaagcggtgt tcgcactcgg ggccggtgtt   5760 gattctatt tgagcaagct acaggcacac cctgaaatgc tgaaccctte tgttccactt   5820 tttcgcctgg aagataccgg tatgggcgag caaatgcagg aatatgctgt cagtcaggtg   5880
ctgcattggt ttcgacgttt tgacgattat cgcatccagc aaaatagttc gcattggcaa   5940
ccgctgcctg aatatcatcg ggaagatttt accatcggca ttttgggcgc aggcgtactg   6000
ggcagtaaag ttgctcagag tctgcaaacc tggcgctttc cgctgcgttg ctggagtcga   6060
acccgtaaat cgtggcctgg cgtgcaaagc tttgccggac gggaagaact gtctgcattt   6120
ctgagccaat gtcgggtatt gattaatttg ttaccgaata cccctgaaac cgtcggcatt   6180
```

```
attaatcaac aattactcga aaaattaccg gatggcgcgt atctcctcaa cctggcgcgt    6240
ggtgttcatg ttgtggaaga tgacctgctc gcggcgctgg atagcggcaa agttaaaggc    6300
gcaatgttgg atgtttttaa tcgtgaaccc ttaccgcctg aaagtccgct ctggcaacat    6360
ccacgcgtga cgataacacc acatgtcgcc gcgattaccc gtcccgctga agctgtggag    6420
tacatttctc gcaccattgc ccagctcgaa aaagggggaga gggtctgcgg gcaagtcgac    6480
cgcgcacgcg gctactaatc tagaaagctt ctgttttggc ggatgagaga agaaaattcgt    6540 cgcccgccat aaactgccag gcatcaaatt aagcagaagg ccatcctgac ggatggcctt    6600
tt                                                                   6602
```

<210> SEQ ID NO 31
<211> LENGTH: 22
<212> TYPE: DNA
<213> ORGANISM: Artificial Sequence
<220> FEATURE:
<223> OTHER INFORMATION: Primer pACT_FW

<400> SEQUENCE: 31
tctagaaagc ttctgttttg gc                                             22

<210> SEQ ID NO 32
<211> LENGTH: 22
<212> TYPE: DNA
<213> ORGANISM: Artificial Sequence
<220> FEATURE:
<223> OTHER INFORMATION: ppc_RV

<400> SEQUENCE: 32
gttcctcctt ctagattagc cg                                             22

<210> SEQ ID NO 33
<211> LENGTH: 48
<212> TYPE: DNA
<213> ORGANISM: Artificial Sequence
<220> FEATURE:
<223> OTHER INFORMATION: Primer aceA_FW

<400> SEQUENCE: 33
cggctaatct agaaggagga accgtatgaa aacccgtaca caacaaat                 48

<210> SEQ ID NO 34
<211> LENGTH: 47
<212> TYPE: DNA
<213> ORGANISM: Artificial Sequence
<220> FEATURE:
<223> OTHER INFORMATION: Primer aceA_RV

<400> SEQUENCE: 34
ttgtatcagc catcgtgtgc ctcctttaga actgcgattc ttcagtg                  47

<210> SEQ ID NO 35
<211> LENGTH: 49
<212> TYPE: DNA
<213> ORGANISM: Artificial Sequence
<220> FEATURE:
<223> OTHER INFORMATION: Primer gltA_FW

<400> SEQUENCE: 35
atcgcagttc taaaggaggc acacgatggc tgatacaaaa gcaaaactc                49

<210> SEQ ID NO 36
<211> LENGTH: 52

```
<212> TYPE: DNA
<213> ORGANISM: Artificial Sequence
<220> FEATURE:
<223> OTHER INFORMATION: Primer gltA_RV

<400> SEQUENCE: 36
agatgatatc catcgtgtgc ctcctttaac gcttgatatc gcttttaaag tc          52

<210> SEQ ID NO 37
<211> LENGTH: 51
<212> TYPE: DNA
<213> ORGANISM: Artificial Sequence
<220> FEATURE:
<223> OTHER INFORMATION: Primer ghrA_FW

<400> SEQUENCE: 37
tatcaagcgt taaaggaggc acacgatgga tatcatcttt tatcacccaa c           51

<210> SEQ ID NO 38
<211> LENGTH: 43
<212> TYPE: DNA
<213> ORGANISM: Artificial Sequence
<220> FEATURE:
<223> OTHER INFORMATION: Primer ghrA_RV

<400> SEQUENCE: 38
tccgccaaaa cagaagcttt ctagattagt agccgcgtgc gcg                    43
```

MICROORGANISMS AND METHODS FOR THE PRODUCTION OF GLYCOLIC ACID AND GLYCINE VIA REVERSE GLYOXYLATE SHUNT

CROSS-REFERENCE TO RELATED APPLICATIONS

This application claims priority to U.S. Provisional Application No. 62/806,195 filed Feb. 15, 2019, entitled "MICROORGANISMS AND METHODS FOR THE PRODUCTION OF GLYCOLIC ACID AND GLYCINE VIA REVERSE GLYOXYLATE SHUNT", the disclosure of which is incorporated by reference herein.

FIELD OF THE INVENTION

This application relates to recombinant microorganisms for the biosynthesis and yield improvement of glycolic acid and/or glycine from glyoxylate using a reverse glyoxylate shunt and methods of producing the recombinant microorganisms. The application further relates to methods of producing glycolic acid and/or glycine from a carbon source such as a hexose or a pentose feedstock via a reverse glyoxylate shunt using the recombinant microorganisms. The application further relates to compositions comprising one or more of these compounds and/or the recombinant microorganisms.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BRSK-010_02US_ST25.txt. The text file is about 45.5 KB, was created on Feb. 14, 2020, and is being submitted electronically via EFS-Web.

BACKGROUND

Glycolic acid and glycine are valuable raw materials in the production of a number of compounds. For example, glycolic acid is an important raw material in the production of products like polyglycolic acid and other biocompatible copolymers. Similarly, glycine has a number of uses in the pharmaceutical and cosmetic industry, pesticide production (pyrethroid insecticides), and as food and feed additive.

To develop environmentally friendly processes for the production of glycolic acid (GA) and glycine, researchers have engineered microorganisms with biosynthetic pathways to produce GA and/or glycine. For example, U.S. Pat. Nos. 9,034,615 and 8,945,888 disclose production of glycolic acid via a glyoxylate shunt (GS) pathway. U.S. Pre-grant Publication No. 2014/0295510 discloses a GS pathway in eukaryotes for production of glycolic acid while patent documents such as WO 2017/059236, WO 2016/079440, US 2016/0076061 and US 2015/0147794 disclose production of glycolic acid using pentose-based sugars. Although the biochemical pathways described in these and other patent documents are developed with an aim to provide high GA and glycine yields, the yields of GA and glycine provided by these routes are still not optimal because these pathways generate excess NADH and excess $CO_2$, which result in loss of product yield.

The present invention provides biosynthetic pathways to produce glycolic acid and glycine at higher theoretical yield potential compared to existing metabolic pathways, solving or, in part, reducing the problem of lost product yield potential. The present invention provides biosynthetic pathways, wherein carbon fixation enzymes and reverse glyoxylate shunt enzymes are coupled to produce and increase yield of glycolic acid and glycine. The present invention also provides further improvements to prevent carbon loss from previously described pathways, and to favor carbon fixation coupling to the reverse glyoxylate shunt.

The present invention also aims to further increase theoretical yield of glycolic acid and glycine of previously described pathways, in part by utilizing $CO_2$ and/or NAD(P)H released by these pathways or by capturing carbon sources ($CO_2$, $HCO_{3-}$, or other carbonates) exogenously provided. The present invention additionally provides biosynthetic pathways to produce and improve GA and glycine yield potential of previously described pathways, rerouting carbon flow via carbon fixation in the pyruvate and/or phosphoenolpyruvate node towards oxaloacetate, in part diminishing or even abolishing carbon loss in metabolic and enzymatic reactions native to the microorganism.

Thus, the present invention allows higher production of GA and glycine using the same amount of starting carbon source (e.g. sugars) and provides ways to increase the economic success of current methods.

SUMMARY OF THE DISCLOSURE

The present disclosure provides recombinant microorganisms and uses thereof. Also provided are methods of making the recombinant microorganism. In various embodiments, the recombinant microorganism of the present disclosure produce glycolic acid (GA) and/or glycine via glyoxylate as the intermediate.

In some embodiments, provided herein is a glyoxylate producing recombinant microorganism for the synthesis of glycolic acid (GA) and/or glycine, wherein the microorganism comprises: (a) a gene encoding malate dehydrogenase that catalyzes the conversion of pyruvate to malate; (b) a gene encoding malate thiokinase that catalyzes the conversion of malate to malyl coenzyme A; and (c) a gene encoding malyl coenzyme A lyase that catalyzes the conversion of malyl coenzyme A to glyoxylate and acetyl-CoA.

In some embodiments, provided herein is a glyoxylate producing recombinant microorganism for the synthesis of glycolic acid (GA) and/or glycine, wherein the microorganism comprises: (a) a gene encoding pyruvate carboxylase that catalyzes the conversion of pyruvate to oxaloacetate (OAA), and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; (b) a gene encoding malate thiokinase that catalyzes the conversion of malate to malyl coenzyme A; and (c) a gene encoding malyl coenzyme A lyase that catalyzes the conversion of malyl coenzyme A to glyoxylate and acetyl-CoA, wherein the acetyl-CoA produced by the malyl coenzyme A lyase combines with the OAA to increase the biosynthesis of GA and/or glycine.

In some embodiments, provided herein is a glyoxylate producing recombinant microorganism for the synthesis of glycolic acid (GA) and/or glycine, wherein the microorganism comprises: (a) a gene encoding pyruvate carboxylase that catalyzes the conversion of pyruvate to oxaloacetate (OAA), and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; (b) a gene encoding malate dehydrogenase that catalyzes the conversion of OAA to malate; (c) a gene encoding malate thiokinase that catalyzes the conversion of malate to malyl coenzyme A; and (d) a gene encoding malyl coenzyme A lyase that catalyzes the conversion of malyl coenzyme A to glyoxylate and acetyl-CoA, wherein the acetyl-CoA produced by the malyl coenzyme A lyase combines with the OAA to increase the biosynthesis of GA and/or glycine. In some of these embodiments, the recombinant microorganism may comprise a gene encoding malate dehydrogenase that catalyzes the conversion of pyruvate to malate.

In some embodiments, provided herein is a glyoxylate producing recombinant microorganism for the synthesis of glycolic acid (GA) and/or glycine, wherein the microorganism comprises: (a) a gene encoding pyruvate carboxylase that catalyzes the conversion of pyruvate to oxaloacetate (OAA), and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; (b) a gene encoding malate thiokinase that catalyzes the conversion of malate to malyl coenzyme A; and (c) a gene encoding malyl coenzyme A lyase that catalyzes the conversion of malyl coenzyme A to glyoxylate and acetyl-CoA, wherein the recombinant microorganism does not catalyze the conversion of oxaloacetate to malate.

In some embodiments, provided herein is a glyoxylate producing recombinant microorganism for the synthesis of glycolic acid (GA) and/or glycine, wherein the microorganism comprises: (a) a gene encoding pyruvate carboxylase that catalyzes the conversion of pyruvate to oxaloacetate (OAA), and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; (b) a gene encoding malate thiokinase that catalyzes the conversion of malate to malyl coenzyme A; (c) a gene encoding malyl coenzyme A lyase that catalyzes the conversion of malyl coenzyme A to glyoxylate and acetyl-CoA, wherein the acetyl-CoA produced by the malyl coenzyme A lyase combines with the OAA to increase the biosynthesis of GA and/or glycine. In these embodiments, this recombinant microorganism has a reduced phosphoglucose isomerase activity or, more preferably, does not catalyze the conversion of glucose-6-phosphate to fructose-6-phosphate by the enzyme phosphoglucose isomerase. Additionally, this recombinant microorganism may or may not comprise endogenous or exogenous enzymes citrate synthase, isocitrate lyase and/or glyoxylate reductase overexpressed. By reducing the activity of the phosphoglucose isomerase, or more preferably by deleting the gene which encodes the phosphoglucose isomerase (gene pgi in *E. coli*, for example) that catalyzes the conversion of glucose-6-phosphate into fructose-6-phosphate, the carbon source can be at least partially diverted towards the pentose-phosphate pathway (PPP) in order to provide additional NADPH potentially required for optimal conversion of glyoxylate into glycolate. In some embodiments, the $CO_2$ generated through the PPP route can potentially be re-incorporated by the use of the carboxylase and carboxykinase enzymes herein proposed.

The recombinant microorganisms of any one of the embodiments described herein may not produce isopropyl alcohol, ethanol, acetone, citric acid, itaconic acid, acetic acid, butyric acid, (poly-)3-hydroxybutyric acid, 3-hydroxyisobutyric acid, 3-aminoisobutyric acid, 2-hydroxyisobutyric acid, methacrylic acid, (poly)glutamic acid, glutamic acid, arginine, ornithine, citrulline, leucine, isoleucine, or proline via the acetyl-CoA produced by the malyl coenzyme A lyase.

In the recombinant microorganisms of the present disclosure, the acetyl-CoA produced by the malyl coenzyme A lyase is expected to combine with the OAA to increase the biosynthesis of GA and/or glycine.

In some embodiments, any one of the recombinant microorganisms described herein may comprise a deletion or loss of function mutation in the gene encoding malate dehydrogenase, wherein the mutation results in a partial or complete inhibition of the malate dehydrogenase activity that catalyzes the conversion of oxaloacetate to malate, malate to pyruvate and/or malate to oxaloacetate.

In the embodiments, where the recombinant microorganisms produce glycolic acid, the recombinant microorganism comprises a gene encoding NADH-dependent glyoxylate reductase that catalyzes the conversion of glyoxylate to glycolate and/or a gene encoding NADPH-dependent glyoxylate reductase that catalyzes the conversion of glyoxylate to glycolate.

In the embodiments, where the recombinant microorganisms produce glycine, the recombinant microorganism comprises a gene encoding alanine-glyoxylate aminotransferase, a gene encoding glycine dehydrogenase, a gene encoding glycine transaminase, a gene encoding serine-glyoxylate transaminase, and/or a gene encoding glycine oxidase to catalyze the conversion of glyoxylate to glycine.

In some embodiments, the recombinant microorganisms of the present disclosure may produce both glycolic acid and glycine and would comprise one or more of the genes described above that convert glyoxylate to GA and/or glycine.

In some embodiments, the gene encoding glyoxylate reductase activity is selected from the group consisting of: ycdW and/or yiaE from *E. coli*, GOR1 from *S. cerevisiae*, gyaR from *Thermococcus litoralis*, and/or GLYR1 from *A. thaliana*. The present disclosure also contemplates the use of homologs of these genes to catalyze the conversion of glyoxylate to glycolate.

In some embodiments, the malate dehydrogenase that catalyzes the carboxylation of pyruvate to malate in the recombinant microorganisms of the present disclosure is from the Enzyme Classification (E.C.) 1.1.1.38, E.C. 1.1.1.39, or E.C. 1.1.1.40.

In some embodiments, the malate dehydrogenase that catalyzes the conversion of oxaloacetate to malate in the recombinant microorganisms of the present disclosure is from the Enzyme Classification (E.C.) 1.1.1.37.

In some embodiments, the gene encoding the malate dehydrogenase that catalyzes the carboxylation of pyruvate to malate in the recombinant microorganisms of the present disclosure is selected from the group consisting of: maeA, maeB, dme, mez, mae1, nad-me1, nad-me2, and homologs thereof. In these embodiments, the gene maeA can be from *E. coli*, *Pseudomonas*, or *Bacillus*; the gene maeB can be from *E. coli* or *Salmonella*; the gene dme can be from *Rhizobium*; the gene mez can be from *Mycobacterium*; the gene mae1 can be from *S. cerevisiae*; and the gene nad-me1 or nad-me2 can be from *Arabidopsis thaliana*. For example, the gene maeA can be from *B. subtilis*; the gene dme can be from *R. melilote*; or the gene mez can be from *Mycobacte-*

*rium tuberculosis*. The present disclosure also contemplates the use of homologs of these genes to catalyze the carboxylation of pyruvate to malate.

In some embodiments, the gene encoding the malate dehydrogenase that catalyzes the conversion of oxaloacetate to malate in the recombinant microorganisms of the present disclosure is selected from the group consisting of: gene mdh from *E. coli, Corynebacterium, Streptomyces, Saccharomyces* and *Arabidopsis*. For example, the gene mdh can be from *S. coelicolor* or gene mdh1/2/3 from *S. cerevisiae*. The present disclosure also contemplates the use of homologs of these genes to catalyze the conversion of oxaloacetate to malate.

In some embodiments, the malate thiokinase that converts malate to malyl coenzyme A can be from the Enzyme Classification System No. E.C. 6.2.1.4, E.C. 6.2.1.5, E.C. 6.2.1.9, or E.C. 6.2.1.-.

In some embodiments, the gene encoding malate thiokinase in the recombinant microorganisms of the present disclosure can be sucCD and/or SucCD-2 and/or mtkAB from *Methylobacterium* sp., *Methylobacterium extorquens, Escherichia coli, Thermus thermophiles, Hyphomicrobium* sp., *Methanocaldococcus jannaschii, Methanothermobacter thermautotrophicus, Rhizobium, Methylococcus capsulatus* or *Pseudomonas*; or homologs thereof.

In some embodiments, the malyl coenzyme A lyase that converts malyl coenzyme A to glyoxylate and acetyl-CoA is from the E.C. 4.3.1.24 or E.C. 4.3.1.25.

In some embodiments, the gene encoding malyl coenzyme A lyase in the recombinant microorganisms of the present disclosure can be mcl and/or Mcl1 and/or mclA from *Methylobacterium extorquens, Rhodobacter sphaeroides, Streptomyces, Chloroflexus aurantiacus, Nitrosomonas europaea, Methylococcus capsulans, Nereida ignava, Hyphomicrobium methylovorum, Thalassobius activus, Roseobacter litoralis, Hyphomicrobium denitrficans, R sphaeroides, Mycobacterium smegmatis* or *Rhodococcus fascians*; or homologs thereof.

In some embodiments, the pyruvate carboxylase that converts pyruvate to OAA can be from the Enzyme Classification System No. E.C. 6.4.1.1; the phosphoenolpyruvate carboxylase that converts phosphoenolpyruvate to OAA can be from the E.C. 4.1.1.31; the phosphoenolpyruvate carboxykinase that converts phosphoenolpyruvate to OAA can be from the E.C. 4.1.1.32 and E.C. 4.1.1.49.

In some embodiments, the gene encoding pyruvate carboxylase in the recombinant microorganisms of the present disclosure can be pyc from *Rhizobium etli*, PYC1 or PYC2 from yeast or pyc from *B. subtilis*; or homologs thereof.

In some embodiments, the gene encoding phosphoenolpyruvate carboxylase in the recombinant microorganisms of the present disclosure can be ppc from *E. coli*, ppc or pepC from *R. marinus*, ppcA from *M. thermautotrophicus*, pep1 from *Z. mays*, ppc1/2/3 from *A. thaliana*, ppc from *G. max* or is from *Rhodothermus, Corynebacterium, Salmonella, Hyphomicrobium, Streptococcus, Streptomyces, Pantoea, Bacillus, Clostridium, Pseudomonas, Rhodopseudomonas, Nicotiana tabacum, Amaranthus hypochondriacus, Triticum aestivum* or *Medicago sativa*; or homologs thereof.

In some embodiments, the gene encoding phosphoenolpyruvate carboxykinase in the recombinant microorganisms of the present disclosure can be pck or pckA from *Escherichia coli*, pckA from *Selenomonas ruminantium*, pckA from *Salmonella typhimurium*, pckA from *Klebsiella* sp., pckA from *Thermus* sp, pck or pckA from *Ruminococcus albus* or *Ruminococcus flavefaciens*, pckA from *Actinobacillus succinogenes*, pck or pckA from *Streptococcus bovis*, or from *Bacillus, Ruminiclostridium thermocellum, Klebsiella, Mycobacterium*; or homologs thereof.

In some embodiments, the recombinant microorganisms of the present disclosure comprise: (a) a gene encoding citrate synthase to convert OAA and acetyl-coA produced by the malyl-coA lyase to citrate; (b) a gene encoding citrate hydro-lyase to convert citrate to cis-aconitate; (c) a gene encoding D-threo-isocitrate hydro-lyase or aconitase to convert cis-aconitate to isocitrate; (d) a gene encoding isocitrate lyase to convert isocitrate to succinate and glyoxylate; (e) a gene encoding succinate dehydrogenase to convert succinate to fumarate; and (f) a gene encoding fumarase to convert fumarate to malate. In the same embodiment, the recombinant microorganisms may have the malate dehydrogenase that catalyzes the conversion of malate to oxaloacetate at least partially preserved. Alternatively, the malate dehydrogenase that catalyzes the conversion of malate to oxaloacetate may be down-regulated or even inactivated to favor the activity of the malate thiokinase enzyme.

In some embodiments, the recombinant microorganisms of the present disclosure may comprise a loss of function mutation or deletion of the gene encoding malate synthase. Exemplary genes encoding the malate synthase include aceB and/or glcB from *E. coli* or DAL7 and/or MLS1 from yeast, e.g., *S. cerevisiae*.

The recombinant microorganisms of any one of the embodiments disclosed herein may comprise a deletion or modification that decreases the activity of one or more endogenous genes selected from the group consisting of: (a) a gene encoding isocitrate dehydrogenase; (b) a gene encoding pyruvate dehydrogenase, pyruvate oxidase and/or pyruvate formate-lyase; (c) a gene encoding pyruvate kinase; and (d) a gene encoding glycolate oxidase. Exemplary genes encoding isocitrate dehydrogenase include icd from *E. coli* or IDP2 and/or IDH1/2 from yeast. Exemplary genes encoding pyruvate dehydrogenase include aceE and/or aceF from *E. coli*. Exemplary genes encoding pyruvate kinase include pykA and/or pykF from *E. coli*. Exemplary genes encoding glycolate oxidase include glcD, glcE, glcF, and/or glcG from *E. coli*. Exemplary genes.

The recombinant microorganism of any one of the embodiments disclosed herein may comprise a deletion or modification that decreases the activity of the pyruvate dehydrogenase, preventing or at least diminishing a major carbon loss from pyruvate conversion to acetyl-CoA, and favoring the carbon rerouting from pyruvate or phosphoenolpyruvate into oxaloacetate via carboxylation activity of enzyme candidates proposed herein.

The recombinant microorganism of any one of the embodiments disclosed herein may comprise a deletion or modification that decreases the activity of the pyruvate kinase, favoring the carbon fixation of phosphoenolpyruvate into oxaloacetate via carboxylation activity of enzyme candidates proposed herein.

The recombinant microorganisms of any one of the embodiments disclosed herein may comprise a deletion or modification that decreases the activity of one or more endogenous genes selected from the group consisting of: (a) a gene encoding glyoxylate carboligase; (b) a gene encoding 2-oxo-4-hydroxyglutarate aldolase; (c) a gene encoding glycoaldehyde reductase; and (d) a gene encoding a repressor of isocitrate lyase. An exemplary gene encoding glyoxylate carboligase is gcl. An exemplary gene encoding 2-oxo-4-hydroxyglutarate aldolase is edA. Exemplary genes encoding glycoaldehyde reductase include fucO and gldA. An exemplary gene encoding the repressor of isocitrate lyase is iclR.

In some embodiments, in the recombinant microorganisms of the present disclosure, the level of expression of a gene encoding alanine-glyoxylate aminotransferase, a gene encoding glycine dehydrogenase, a gene encoding glycine transaminase, a gene encoding serine-glyoxylate transaminase, and/or a gene encoding glycine oxidase is increased.

In some embodiments, in the recombinant microorganisms of the present disclosure, the level of expression of a gene encoding alanine transaminase and/or a gene encoding NADPH-dependent glutamate synthase is increased.

In some embodiments, in the recombinant microorganisms of the present disclosure, the synthesis of glycolic acid and/or glycine is increased by increasing the level of expression or the activity or the specificity of at least one enzyme selected from the group consisting of: pyruvate carboxylase, phosphoenolpyruvate carboxylase, phosphoenolpyruvate carboxykinase, malate dehydrogenase, malate thiokinase, malyl coenzyme A lyase, alanine-glyoxylate aminotransferase, glycine dehydrogenase, glycine transaminase, serine-glyoxylate transaminase, glycine oxidase, NADH-dependent glyoxylate reductase, and NADPH-dependent glyoxylate reductase.

In some embodiments, in the recombinant microorganisms of the present disclosure, the synthesis of glycolic acid and/or glycine is increased by decreasing the level of expression or the activity or the specificity of at least one enzyme selected from the group consisting of: malate synthase, isocitrate dehydrogenase, pyruvate dehydrogenase, pyruvate oxidase and/or pyruvate formate-lyase, pyruvate kinase, glyoxylate carboligase, 2-oxo-4-hydroxyglutarate aldolase, glucose-6-phosphate isomerase, glycoaldehyde reductase, and glycolate oxidase.

In some embodiments, in the recombinant microorganisms of the present disclosure, the synthesis of glycolic acid and/or glycine is increased by decreasing the level of expression of a gene encoding a repressor of isocitrate lyase.

In some embodiments, the recombinant microorganisms of the present disclosure may utilize NADH and $CO_2$ generated by other glycolic acid and/or glycine producing pathways in the reactions catalyzed by malate dehydrogenase, pyruvate carboxylase, phosphoenolpyruvate carboxylase, phosphoenolpyruvate carboxykinase, malate thiokinase, and malyl coenzyme A lyase. For example, in some embodiments, the recombinant microorganisms of the present disclosure may utilize NADH and/or $CO_2$ generated by a serine/hydroxypyruvate-based pathways in the reactions catalyzed by malate dehydrogenase, pyruvate carboxylase, phosphoenolpyruvate carboxylase, phosphoenolpyruvate carboxykinase, malate thiokinase, and malyl coenzyme A lyase. In some embodiments, the recombinant microorganisms of the present disclosure may utilize NADH and/or $CO_2$ generated by a glyoxylate shunt pathway in the reactions catalyzed by malate dehydrogenase, pyruvate carboxylase, phosphoenolpyruvate carboxylase, phosphoenolpyruvate carboxykinase, malate thiokinase, and malyl coenzyme A lyase. In some embodiments, the recombinant microorganisms of the present disclosure may utilize NADH and/or $CO_2$ generated by a D-erythrose to glycoaldehyde based pathways in the reactions catalyzed by malate dehydrogenase, pyruvate carboxylase, phosphoenolpyruvate carboxylase, phosphoenolpyruvate carboxykinase, malate thiokinase, and malyl coenzyme A lyase. In some embodiments, the recombinant microorganisms of the present disclosure may utilize NADH and/or $CO_2$ generated by a pentose derivative to glycoaldehyde based pathways in the reactions catalyzed by malate dehydrogenase, pyruvate carboxylase, phosphoenolpyruvate carboxylase, phosphoenolpyruvate carboxykinase, malate thiokinase, and malyl coenzyme A lyase.

In some embodiments, the recombinant microorganisms of the present disclosure may utilize exogenously added $CO_2$, a carbonate, and/or a reducing agent in the reactions catalyzed by malate dehydrogenase, pyruvate carboxylase, phosphoenolpyruvate carboxylase, phosphoenolpyruvate carboxykinase, malate thiokinase, and malyl coenzyme A lyase. The reducing agent can be hydrogen, electrons, and/or NAD(P)H.

The recombinant microorganisms provided by the present disclosure include bacterium, yeast, and fungus. In some embodiments, the recombinant microorganism of the present disclosure can be a bacterium selected from the group consisting of Enterobacteriaceae, Clostridiaceae, Bacillaceae, Streptomycetaceae, and Corynebacteriaceae. In an exemplary embodiment, the recombinant microorganism of the present disclosure can be a species of *Escherichia, Clostridium, Bacillus, Klebsiella, Pantoea, Salmonella, Lactobacillus*, or *Corynebacterium*. For example, the recombinant microorganism of the present disclosure can be *Escherichia coli, Corynebacterium glutamicum, Clostridium acetobutylicum*, or *Bacillus subtilis*.

In some embodiments, the recombinant microorganism of the present disclosure can be a yeast selected from the family Saccharomycetaceae. In an exemplary embodiment, the recombinant microorganism of the present disclosure can be a species of *Saccharomyces*. For example, the recombinant microorganism of the present disclosure can be *Saccharomyces cerevisiae*.

In the recombinant microorganisms of the present disclosure, any one of the genes described herein are expressed heterologously.

The present disclosure also provides methods of producing GA and/or glycine using the recombinant microorganisms described herein. In some embodiments, methods for producing glycolic acid and/or glycine using the recombinant microorganisms described herein comprise cultivating the recombinant microorganism in a culture medium containing a feedstock providing a carbon source until the glycolic acid and/or glycine are produced.

In some embodiments, the carbon source used in the methods of producing GA and/or glycine can be selected from the group consisting of: sugars, glycerol, alcohols, organic acids, alkanes, fatty acids, hemicellulose, lignocellulose, proteins, carbon dioxide, and carbon monoxide. In exemplary embodiments, the carbon source is a hexose and/or pentose sugar. In an exemplary embodiment, the carbon source is glucose. In another exemplary embodiment, the carbon source is sucrose. In another exemplary embodiment, the carbon source comprises a biomass hydrolysate comprising hemicellulose. In another exemplary embodiment, the carbon source is $CO_2$ or carbonate such as $HCO_3^-$.

Also provided herein are methods of producing recombinant microorganisms that produce glycolic acid and/or glycine from glyoxylate.

In some embodiments, a method of producing a recombinant microorganism that produces glycolic acid and/or glycine comprises introducing into the microorganism: (a) a gene encoding malate dehydrogenase that catalyzes the conversion of pyruvate to malate; (b) a gene encoding malate thiokinase that catalyzes the conversion of malate to malyl coenzyme A; and (c) a gene encoding malyl coenzyme A lyase that catalyzes the conversion of malyl coenzyme A to glyoxylate and acetyl-CoA.

In some embodiments, a method of producing a recombinant microorganism that produces glycolic acid and/or glycine comprises introducing into the microorganism: (a) a gene encoding pyruvate carboxylase that catalyzes the conversion of pyruvate to OAA, and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; (b) a gene encoding malate dehydrogenase that catalyzes the conversion of OAA to malate; (c) a gene encoding malate thiokinase that catalyzes the conversion of malate to malyl coenzyme A; and (d) a gene encoding malyl coenzyme A lyase that catalyzes the conversion of malyl coenzyme A to glyoxylate and acetyl-CoA, wherein the acetyl-CoA produced by the malyl coenzyme A lyase combines with the OAA to increase the biosynthesis of GA and/or glycine. In some of these embodiments, the method may comprise introducing into the microorganism a gene encoding malate dehydrogenase that catalyzes the conversion of pyruvate to malate.

In some embodiments, a method of producing a recombinant microorganism that produces glycolic acid and/or glycine comprises introducing into the microorganism: (a) a gene encoding pyruvate carboxylase that catalyzes the conversion of pyruvate to oxaloacetate (OAA), and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; (b) a gene encoding malate thiokinase that catalyzes the conversion of malate to malyl coenzyme A; and (c) a gene encoding malyl coenzyme A lyase that catalyzes the conversion of malyl coenzyme A to glyoxylate and acetyl-CoA, wherein the recombinant microorganism does not catalyze the conversion of oxaloacetate to malate.

In an exemplary embodiment, the gene encoding malate dehydrogenase introduced into the microorganism heterogeneously comprises a mutation that results in a partial or complete inhibition of the malate dehydrogenase activity that catalyzes the conversion of oxaloacetate to malate, malate to pyruvate or malate to oxaloacetate. In another exemplary embodiment, if the gene encoding malate dehydrogenase that catalyzes the conversion of pyruvate to malate and/or oxaloacetate to malate is present endogenously in the recombinant microorganism, then the method for producing the recombinant microorganism that produces glycolic acid and/or glycine comprises introducing a mutation into the endogenous gene encoding malate dehydrogenase, wherein the mutation results in a partial or complete inhibition of the malate dehydrogenase activity that catalyzes the conversion of oxaloacetate to malate, malate to pyruvate or malate to oxaloacetate.

In some embodiments, the methods for producing a recombinant microorganism that produces glycolic acid and/or glycine may further comprise introducing into the microorganism; (a) a gene encoding NADH-dependent glyoxylate reductase that catalyzes the conversion of glyoxylate to glycolate; (b) a gene encoding NADPH-dependent glyoxylate reductase that catalyzes the conversion of glyoxylate to glycolate; and/or c) a gene encoding alanine-glyoxylate aminotransferase, a gene encoding glycine dehydrogenase, a gene encoding glycine transaminase, a gene encoding serine-glyoxylate transaminase, and/or a gene encoding glycine oxidase that catalyzes the conversion of glyoxylate to glycine.

In some embodiments, the methods for producing a recombinant microorganism that produces glycolic acid and/or glycine may further comprise introducing into the microorganism a loss of function mutation or deletion of the gene encoding malate synthase.

In some embodiments, the method for producing a recombinant microorganism that produces glycolic acid and/or glycine may further comprise introducing into the microorganism a deletion or modification that reduces the activity of one or more enzymes encoded by the genes selected from the group consisting of: (a) a gene encoding isocitrate dehydrogenase; (b) a gene encoding pyruvate dehydrogenase, pyruvate oxidase and/or pyruvate formate-lyase; (c) a gene encoding pyruvate kinase; and (d) a gene encoding glycolate oxidase.

In some embodiments, the method for producing a recombinant microorganism that produces glycolic acid and/or glycine may further comprise introducing into the microorganism a deletion or modification that reduces the activity of one or more enzymes encoded by the genes selected from the group consisting of: (a) a gene encoding glyoxylate carboligase; (b) a gene encoding 2-oxo-4-hydroxyglutarate aldolase; (c) a gene encoding glycoaldehyde reductase; and (d) a gene encoding a repressor of isocitrate lyase.

In some embodiments, the method for producing a recombinant microorganism that produces glycolic acid and/or glycine may further comprise introducing a gain of function mutation into the gene encoding alanine-glyoxylate aminotransferase, the gene encoding alanine-glyoxylate aminotransferase glyoxylate to glycine, the gene encoding glycine dehydrogenase, the gene encoding glycine transaminase, the gene encoding serine-glyoxylate transaminase, and/or the gene encoding glycine oxidase that catalyze the conversion of glyoxylate to glycine.

In some embodiments, the method for producing a recombinant microorganism that produces glycolic acid and/or glycine may further comprise introducing a gain of function mutation into a gene encoding alanine transaminase and/or a gene encoding NADPH-dependent glutamate synthase.

In the embodiments where a gain of function mutation is introduced into a gene, the gain of function mutation may be introduced into the gene that is endogenous to the microorganism or a gain of function mutation may be introduced into a heterogeneous gene and introducing the heterogeneous gene comprising the gain of function mutation into the microorganism.

The microorganisms that may be used to produce the recombinant microorganisms of the present disclosure include bacterium, yeast, and fungus. Exemplary bacteria that may be used in the present disclosure include bacteria selected from the group consisting of Enterobacteriaceae, Clostridiaceae, Bacillaceae, Streptomycetaceae, and Corynebacteriaceae. For example, the recombinant microorganism can be a species of *Escherichia*, e.g. *Escherichia coli*, *Clostridium*, e.g., *Clostridium acetobutylicum*, *Bacillus*, e.g. *Bacillus subtilis*, *Klebsiella*, *Pantoea*, *Salmonella*, *Lactobacillus*, or *Corynebacterium*, e.g. *Corynebacterium glutamicum*.

Exemplary yeast that may be used to produce the recombinant microorganisms of the present disclosure can be from the family Saccharomycetaceae. For example, the recombinant microorganism can be a species of *Saccharomyces*, e.g. *Saccharomyces cerevisiae*.

The symbol ✗ means enzymes to be potentially down regulated or inactivated/abolished, ie. respective gene potentially attenuated or deleted.

Figure 1:
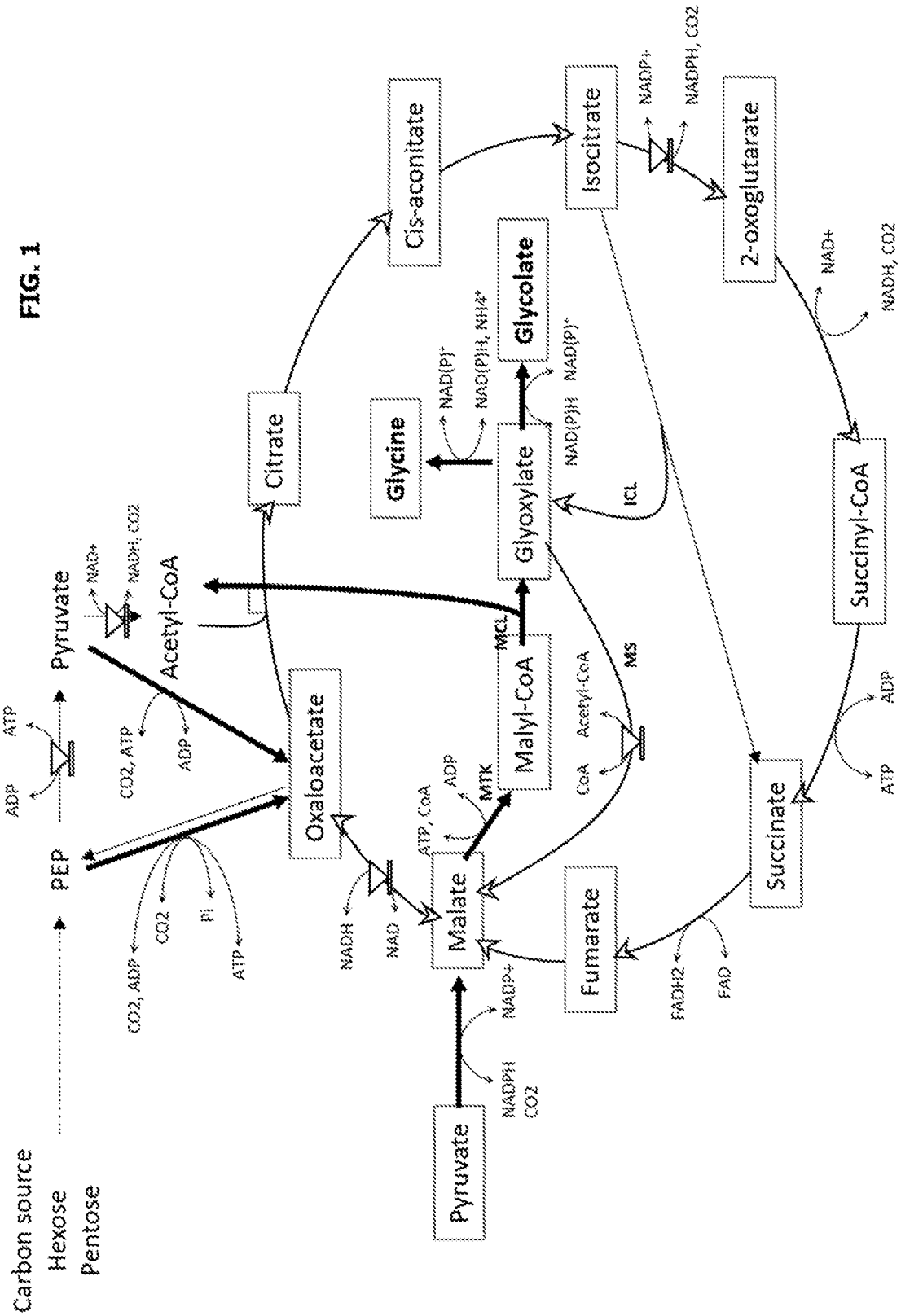
FIG. 1 illustrates a schematic of glycolic acid (GA) and glycine (Gly) production via the reverse glyoxylate shunt.
Figure 2:
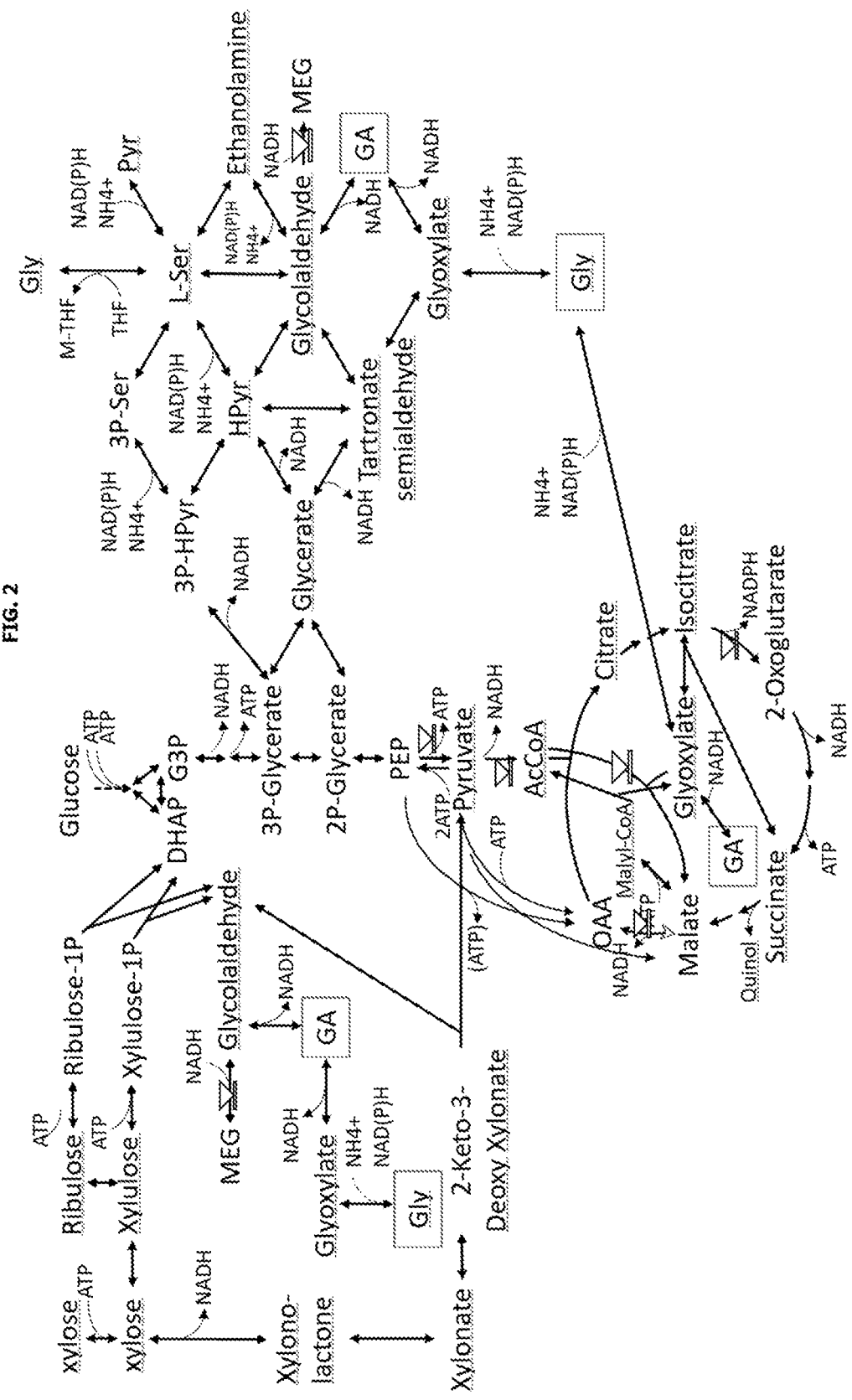

FIG. 2 illustrates a schematic of co-utilization of known glycolic acid (GA) and glycine (Gly) production pathways with the reverse glyoxylate shunt pathway of the present disclosure. Dashed lines show reaction summaries. The symbol ✗ means enzymes to be potentially down regulated or inactivated/abolished, ie. respective gene potentially attenuated or deleted.

Figure 3:
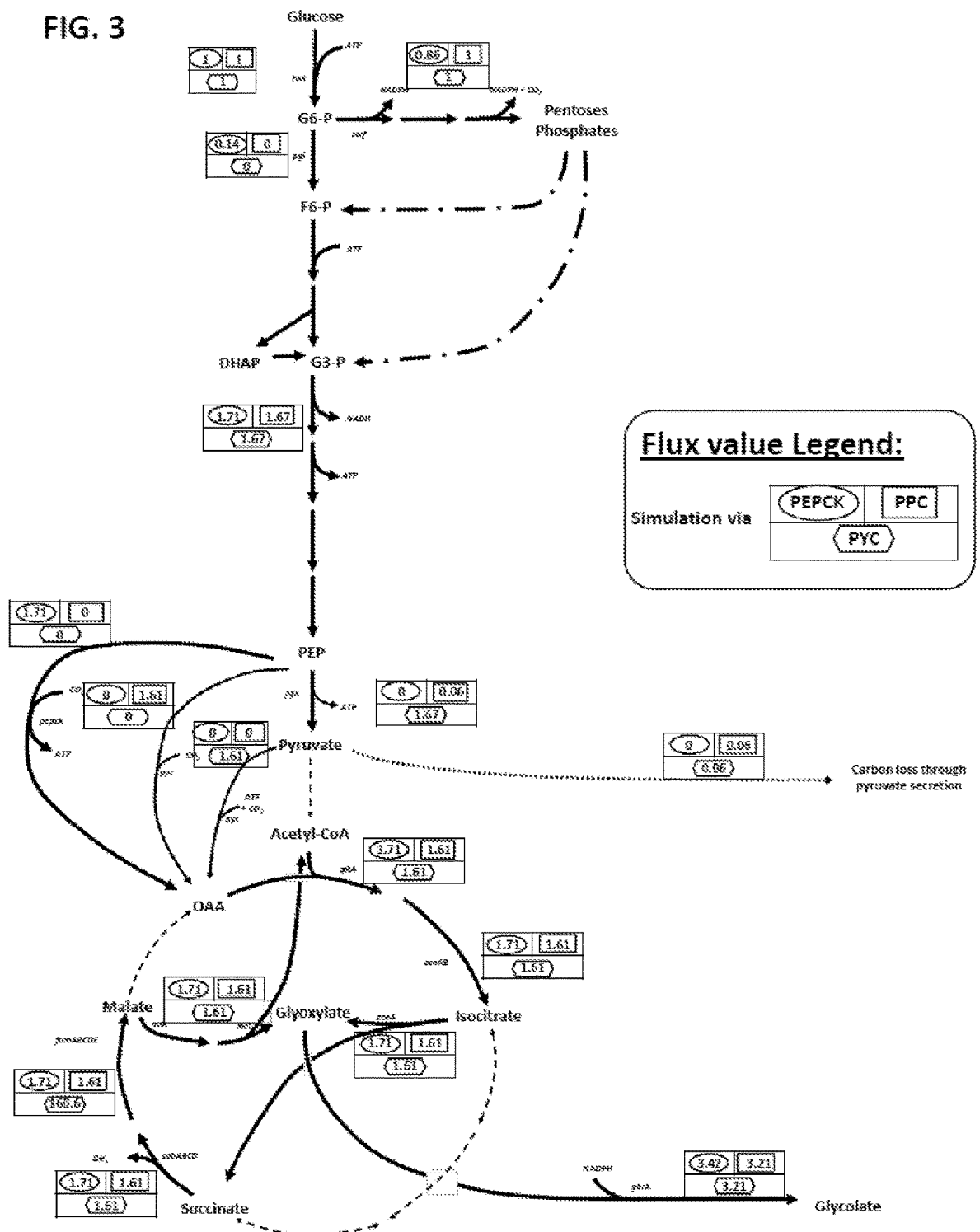

FIG. 3 is a schematic depicting a flux map towards maximal theoretical production yield of GA from glucose, using a hexokinase transport system, carboxylation via phosphoenolpyruvate carboxykinase (PEPCK), phosphoenolpyruvate carboxylase (PPC) or pyruvate carboxylase (PYC), and the combination of the glyoxylate shunt (GS) and reverse gyloxylate shunt (rGS). Flux analysis was based on the use of a NADPH-dependent glyoxylate reductase enzyme candidate. Flux values are normalized against the glucose input.

Figure 4:
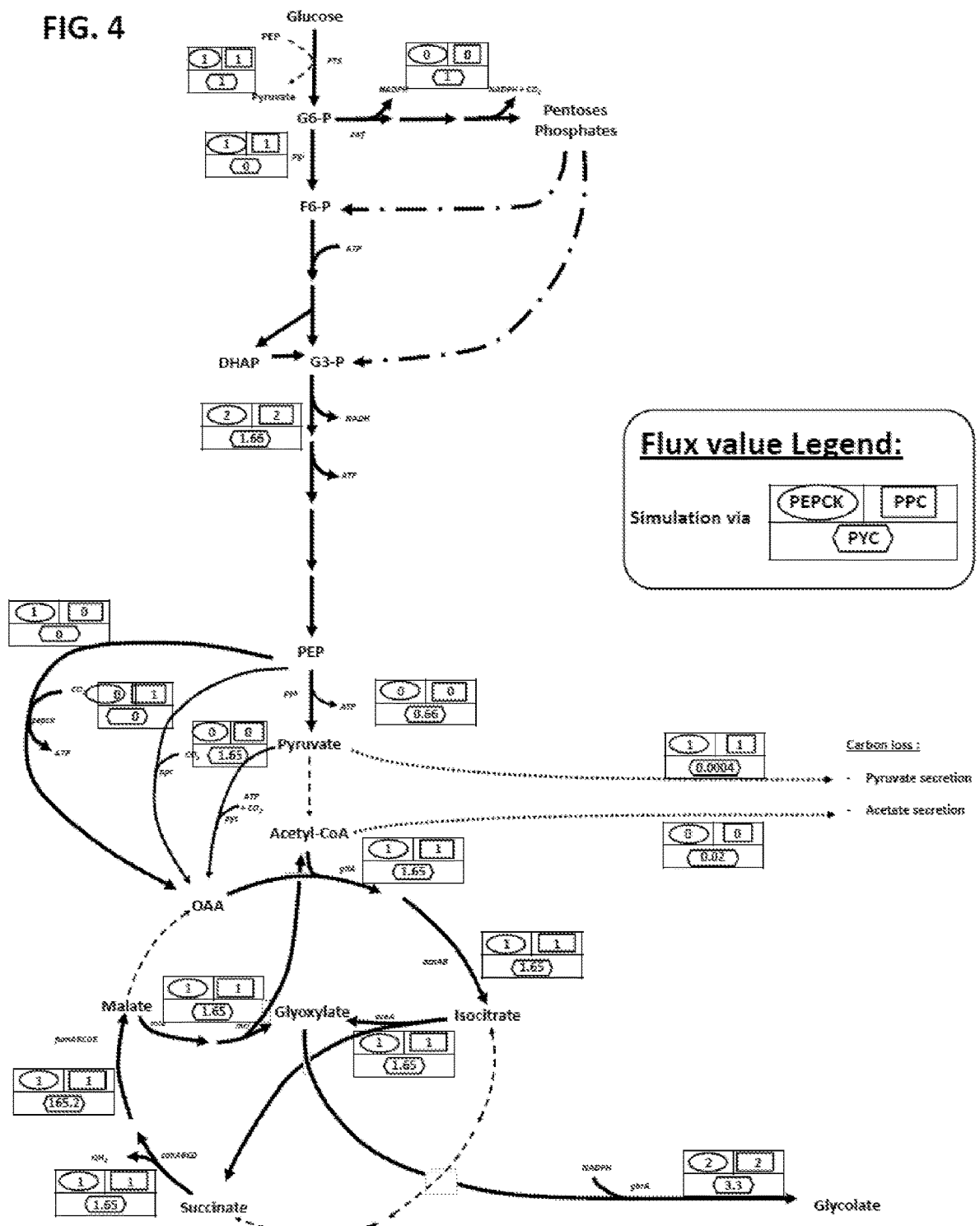

FIG. 4 is a schematic depicting a flux map towards maximal theoretical production yield of GA from glucose, using a phosphotransferase system (PTS) transport system, carboxylation via PEPCK, PPC or PYC, and the combination of the GS and rGS. Flux analysis was based on the use of a NADPH-dependent glyoxylate reductase enzyme candidate. Flux values are normalized against the glucose input.

DETAILED DESCRIPTION

Definitions

The following definitions and abbreviations are to be used for the interpretation of the disclosure.

As used herein and in the appended claims, the singular forms "a," "an," and "the" include plural referents unless the context clearly dictates otherwise. Thus, for example, reference to "an enzyme" includes a plurality of such enzymes and reference to "the microorganism" includes reference to one or more microorganisms, and so forth.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganism. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. It is understood that the terms "recombinant microorganism" and "recombinant host cell" refer not only to the particular recombinant microorganism but to the progeny or potential progeny of such a microorganism.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "decreasing" or "reducing" the level of expression of a gene or an enzyme activity refers to the partial or complete suppression of the expression of a gene or enzyme activity. This suppression of expression or activity can be either an inhibition of the expression of the gene, a deletion of all or part of the promoter region necessary for the gene expression, a deletion in the coding region of the gene, or the replacement of the wild-type promoter by a weaker natural or synthetic promoter. For example, a gene may be completely deleted and may be replaced by a selection marker gene that facilitates the identification, isolation and purification of the strains according to the invention. Alternatively, endogenous genes may be knocked out or deleted to favor the new metabolic pathway. In yet another embodiment, the expression of the gene may be decreased or reduced by using a weak promoter or by introducing certain mutations.

As used herein, the term "non-naturally occurring," when used in reference to a microorganism organism or enzyme activity of the disclosure, is intended to mean that the microorganism organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid is produced in an unnatural (e.g., greater than naturally found) amount in the cell. The heterologous expression of polynucleotides can be via the introduction of one or more vectors (e.g., plasmids, cosmids, viral vectors, etc.) comprising the gene of interest into the host microorganism or via the integration of a construct comprising the gene of interest into the genome of the host microorganism.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.). A similar biological function may include, but is not limited to: catalyzing the same or similar enzymatic reaction; having the same or similar selectivity for a substrate or co-factor; having the same or similar stability; having the same or similar tolerance to various fermentation conditions (temperature, pH, etc.); and/or having the same or similar tolerance to various metabolic substrates, products, by-products, intermediates, etc. The degree of similarity in biological function may vary, but in one embodiment, is at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%, according to one or more assays known to one skilled in the art to determine a given biological function.

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting embodiments, an enzyme may be a "variant" relative to a reference enzyme by virtue of alteration(s) in any part of the polypeptide sequence encoding the reference enzyme. A variant of a reference enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the reference enzyme. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the full-length, or unprocessed enzymes of the present disclosure. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the mature, or processed enzymes of the present disclosure.

The term "yield potential" as used herein refers to a yield of a product from a biosynthetic pathway. In one embodiment, the yield potential may be expressed as a percent by weight of end product per weight of starting compound.

The term "thermodynamic maximum yield" as used herein refers to the maximum yield of a product obtained from fermentation of a given feedstock, such as glucose, based on the energetic value of the product compared to the feedstock. In a normal fermentation, without use of additional energy sources such as light, hydrogen gas or methane or electricity, for instance, the product cannot contain more energy than the feedstock. The thermodynamic maximum yield signifies a product yield at which all energy and mass from the feedstock is converted to the product. This yield can be calculated and is independent of a specific pathway. If a specific pathway towards a product has a lower yield than the thermodynamic maximum yield, then it loses mass and can most likely be improved upon or substituted with a more efficient pathway towards the product.

The term "redox balance" refers to the overall amount of redox cofactors in a given set of reactions. When there is a shortage of redox cofactors, the redox balance is negative and the yield of such pathway would not be realistic since there is a need to burn feedstock to fulfill the cofactor demand. When there is a surplus of redox cofactors, the redox balance is said to be positive and the yield of such pathway is lower than the maximum yield (Dugar et al. "Relative potential of biosynthetic pathways for biofuels and bio-based products" Nature biotechnology 29.12 (2011): 1074). In addition, when the pathway produces the same amount of redox cofactors as it consumes, the redox balance is zero and one can refer to this pathway as "redox balanced". Designing metabolic pathways and engineering an organism such that the redox cofactors are balanced or close to being balanced usually results in a more efficient, higher yield production of the desired compounds when compared to an unbalanced pathway. Redox reactions always occur together as two half-reactions happening simultaneously, one being an oxidation reaction and the other a reduction reaction. In redox processes, the reductant transfers electrons to the oxidant. Thus, in the reaction, the reductant or reducing agent loses electrons and is oxidized, and the oxidant or oxidizing agent gains electrons and is reduced. In one embodiment, the redox reactions take place in a biological system. The term redox state is often used to describe the balance of NAD+/NADH and NADP+/NADPH of natural or non-natural metabolic pathways in a biological system such as a microbial cell. The redox state is reflected in the balance of several sets of metabolites (e.g., lactate and pyruvate, beta-hydroxybutyrate, and acetoacetate), whose interconversion is dependent on these ratios. In one embodiment, an external source of hydrogen or electrons, combined or not with the use of hydrogenase enzymes able to convert hydrogen to NAD(P)H, may be beneficial to increase product yield in metabolic pathways with negative redox balance, i.e., when there is a shortage in redox cofactors, such as NAD(P)H.

Introduction

The glyoxylate shunt (GS) (also called glyoxylate cycle) is a variation of the tricarboxylic acid cycle (TCA cycle) and is an anabolic pathway occurring in plants, bacteria, protists, and fungi. The TCA cycle and the glyoxylate shunt differ in that in the glyoxylate shunt, isocitrate is cleaved into glyoxylate and succinate by isocitrate lyase instead of being decarboxylated and dehydrogenated to α-ketoglutarate. This bypasses the two decarboxylation steps that take place in the TCA cycle allowing acetyl-CoA to be converted to TCA cycle intermediates without carbon loss. Glyoxylate is converted into malate by incorporating a molecule of acetyl-CoA.

Production of glycolic acid using a glyoxylate shunt (GS) pathway is described in U.S. Pat. No. 9,034,615, which is incorporated by reference herein in its entirety. This patent discloses GA production by attenuating the glyoxylate consuming pathways and by increasing the activity of NAD(P)H-dependent glyoxylate reductase. Use of the glyoxylate shunt pathway for production of glycolic acid is also disclosed in U.S. Pat. No. 8,945,888; U.S. Pre-Grant Publication No. 2014/0295510; and PCT Publication No. WO 2016/193540, which are incorporated by reference herein in their entireties. However, the glyoxylate shunt pathway has a reduced total yield potential of 0.84 g_GA/g_glucose, while the thermodynamic maximum yield for a glucose→GA conversion is 1.70 g/g. This pathway is also not redox balanced and has a high excess of 4 mol NADH and 2 mol quinol per mol of consumed glucose, all of which needs to be re-oxidized for the cell to be viable. The overall stoichiometry of this pathway and the yield potential can be summarized as follows: Glucose→2 GA+2 $CO_2$+4 NADH+2 quinol+2 ATP; y=0.84 g/g, 49% of Y(max)=1.70 g/g.

GA production via a pentose derivative to glycolaldehyde-based pathways are described in PCT Publication Nos. WO 2017/059236 and WO 2016/79440 and U.S. Pre-grant Publication Nos. US 2016/0076061 and US 2015/0147794, all of which are incorporated by reference herein in their entirety. However, these pathways also have a reduced total yield potential. For example, GA production using xylose as a source has a reduced yield potential of 1.01 g_GA/g_xylose, while the thermodynamic maximum yield for a xylose→GA conversion is 1.71 g/g. The overall stoichiometry of the xylose-based pathway and the yield potential can be summarized as follows: Xylose→2 GA+1 $CO_2$+3 NADH+1 quinol+0 ATP; y=1.01 g/g, 59% of Y(max)=1.71 g/g. As can be seen from the equation, the xylose-based pathway also produces excess of NADH and $CO_2$.

PCT Publication No. WO 2015/181074, incorporated by reference herein in its entirety, discloses a method for the production of D-erythrose and subsequent conversion of D-erythrose into glycoaldehyde. Glycoaldehyde can be further converted into glycolic acid and/or glycine. This pathway has a reduced yield potential of 1.27 g_GA/g_glucose, while the thermodynamic maximum yield is 1.70 g/g. The overall stoichiometry of the erythrose-based pathway and the yield potential can be summarized as follows: Glucose→3 GA+2 NADH+1 quinol−1 ATP, y=1.27 g/g, 75% of Y(max)=1.70 g/g. This pathway is not redox balanced and has a high excess of 2 mol NADH and 1 mol quinol per mol of consumed glucose, all of which needs to be re-oxidized for the cell to be viable.

A serine/hydroxypyruvate pathway for the GA production is described in U.S. Pat. No. 8,911,978, which is incorporated by reference herein in its entirety.

All of these pathways generate excess NADH and release excess $CO_2$, i.e., these pathways do not reach the thermodynamic possible maximum yield. They typically oxidize more sugar carbon than necessary to $CO_2$, thereby loosing product yield.

The present application relates to glyoxylate producing recombinant microorganisms having one or more biosynthetic pathways for the production of glycolic acid (GA) and/or glycine. In one embodiment, the glyoxylate producing recombinant microorganisms of the present invention comprise a reverse glyoxylate shunt based route that increases the yield of GA and glycine. In another embodiment, the glyoxylate producing recombinant microorganisms of the present invention comprise previously described metabolic pathways and modifications for the production of GA and/or glycine and a reverse glyoxylate shunt based route that further increases the yield of GA and glycine. The terms "glycolic acid" and "glycolate" are used interchangeably throughout this disclosure.

Certain patent documents disclose reverse glyoxylate shunt pathways. For example, U.S. Pat. No. 9,410,131 discloses a reverse glyoxylate shunt pathway to produce oxaloacetate and malonyl-CoA. U.S. Pre-grant Publication No. 2016/369292 discloses the use of reverse glyoxylate shunt to produce isocitrate and acetyl-CoA. EP Patent No. 2738247B1 discloses the use of reverse glyoxylate shunt for the acetyl-CoA production. However, none of these patent documents disclose a reverse glyoxylate shunt to increase the production of glyoxylate and subsequently the production of glycolic acid and/or glycine. Moreover, none of these patent documents disclose a reverse glyoxylate shunt wherein the acetyl-CoA generated from the activity of malyl-CoA lyase is reincorporated into the metabolic pathway, e.g. by combining with oxaloacetate to produce citrate in the glyoxylate shunt, for the increased production of glycolic acid and/or glycine.

The present disclosure provides, for the first time, a carbon-fixing route for GA or glycine production, making it a suitable co-pathway for most of the current GA and glycine pathways with $CO_2$ and NADH excess. By providing a suitable co-pathway, the present disclosure solves the problem of NADH excess of all glycolic acid (GA) and glycine pathways described so far and enables higher GA and glycine yield than previously described pathways alone, including recently published high yield pathways using xylose.

The present disclosure provides, for the first time, a reverse glyoxylate shunt pathway that utilizes a carboxylation reaction for the production of GA and glycine. None of the GA or glycine producing pathways described so far utilizes a carboxylation reaction for the synthesis of GA or glycine.

In certain embodiments, the carboxylation-based reverse glyoxylate shunt pathway of the present disclosure can be utilized synergistically with known GA or glycine producing pathways.

The present disclosure encompasses the use of homologs as well as natural or engineered variants of the genes and/or the enzymes encoded by these genes described herein.

Microorganisms, Pathways, and Methods of the Invention

In one embodiment, the present disclosure provides a glyoxylate producing recombinant microorganism that produces glycolic acid and/or glycine from glyoxylate using a reverse glyoxylate shunt pathway. The expression of the reverse glyoxylate shunt pathway increases the production of glyoxylate as an intermediate and increases the production of final products, glycolic acid and glycine. In some embodiments, the glyoxylate producing recombinant microorganisms of the present invention co-produce glycolic acid and glycine. In another embodiment, the glyoxylate producing recombinant microorganism of the present invention co-produce glycolic acid and another co-product such as, but not limited to, succinate or lactate. In a further embodiment, the glyoxylate producing recombinant microorganism of the present invention co-produce glycine and another co-product such as, but not limited to, succinate or lactate.

In some embodiments, the present disclosure provides a glyoxylate producing recombinant microorganism for the synthesis of glycolic acid and/or glycine, wherein the microorganism comprises: (a) a gene encoding pyruvate carboxylase that catalyzes the conversion of pyruvate to oxaloacetate (OAA), and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; (b) a gene encoding malate thiokinase that catalyzes the conversion of malate to malyl coenzyme A; and (c) a gene encoding malyl coenzyme A lyase that catalyzes the conversion of malyl coenzyme A to glyoxylate and acetyl-CoA, wherein the acetyl-CoA produced by the malyl coenzyme A lyase combines with the OAA to increase the biosynthesis of GA and/or glycine.

In some embodiments, the present disclosure provides a glyoxylate producing recombinant microorganism for the synthesis of glycolic acid and/or glycine, wherein the microorganism comprises: (a) a gene encoding pyruvate carboxylase that catalyzes the conversion of pyruvate to oxaloacetate (OAA), and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; (b) a gene encoding malate thiokinase that catalyzes the conversion of malate to malyl coenzyme A; (c) a gene encoding malyl coenzyme A lyase that catalyzes the conversion of malyl coenzyme A to glyoxylate and acetyl-CoA, wherein the acetyl-CoA produced by the malyl coenzyme A lyase combines with the OAA to increase the biosynthesis of GA and/or glycine. In these embodiments, this recombinant microorganism has a reduced phosphoglucose isomerase activity or, more preferably, does not catalyze the conversion of glucose-6-phosphate to fructose-6-phosphate by the enzyme phosphoglucose isomerase. Additionally, this recombinant microorganism may or may not comprise endogenous or exogenous enzymes citrate synthase, isocitrate lyase and/or glyoxylate reductase overexpressed. By reducing the activity of the phosphoglucose isomerase, or more preferably by deleting the gene which encodes the phosphoglucose isomerase (gene pgi in *E. coli*, for example) that catalyzes the conversion of glucose-6-phosphate into fructose-6-phosphate, the carbon source can be at least partially diverted towards the pentose-phosphate pathway (PPP) in order to provide additional NADPH potentially required for optimal conversion of glyoxylate into glycolate. In some embodiments, the $CO_2$ generated through the PPP route can potentially be re-incorporated by the use of the carboxylase and carboxykinase enzymes herein proposed.

In one embodiment, the reverse glyoxylate shunt based pathway of the present disclosure comprises carboxylating pyruvate to malate; converting malate to malyl-Coenzyme A (CoA) and converting malyl-CoA to glyoxylate and acetyl-CoA. Accordingly, in one embodiment, provided herein is a recombinant microorganism that comprises a gene encoding malate dehydrogenase to convert pyruvate to malate, a gene encoding malate thiokinase to convert malate to malyl coenzyme A, and a gene encoding malyl coenzyme A lyase to convert malyl coenzyme A to glyoxylate and acetyl coenzyme A. In one embodiment, the gene encoding malate dehydrogenase encodes for a modified malate dehydrogenase that catalyzes the conversion of pyruvate to malate but does not catalyze the reverse reaction of malate to pyruvate or shows reduced conversion of malate to pyruvate. In some embodiments, the gene encoding the malate dehydrogenase may comprise a deletion or loss of function mutation. The modified malate dehydrogenase can be a naturally occurring variant or an engineered variant.

In another embodiment, the reverse glyoxylate shunt based pathway of the present disclosure comprises carboxylating phosphoenol pyruvate (PEP) and/or pyruvate to oxaloacetate (OAA); converting OAA to malate; converting malate to malyl-Coenzyme A (CoA) and converting malyl-CoA to glyoxylate and acetyl-CoA. Accordingly, in one embodiment, provided herein is a recombinant microorganism that comprises a gene encoding pyruvate carboxylase to convert pyruvate to OAA, and/or a gene encoding phosphoenolpyruvate carboxylase to convert phosphoenolpyruvate to OAA, and/or a gene encoding phosphoenolpyruvate carboxykinase to convert phosphoenolpyruvate to OAA in combination with a gene encoding malate dehydrogenase that catalyzes the conversion of OAA to malate, a gene encoding malate thiokinase to convert malate to malyl coenzyme A, and a gene encoding malyl coenzyme A lyase to convert malyl coenzyme A to glyoxylate and acetyl coenzyme A.

In another embodiment, the reverse glyoxylate shunt based pathway of the present disclosure comprises carboxylating phosphoenol pyruvate (PEP) or pyruvate to oxaloacetate (OAA) and/or carboxylating pyruvate to malate; converting OAA to malate; converting malate to malyl-Coenzyme A (CoA) and converting malyl-CoA to glyoxylate and acetyl-CoA. Accordingly, in one embodiment, provided herein is a recombinant microorganism that comprises a gene encoding pyruvate carboxylase to convert pyruvate to OAA, and/or a gene encoding phosphoenolpyruvate carboxylase to convert phosphoenolpyruvate to OAA, and/or a gene encoding phosphoenolpyruvate carboxykinase to convert phosphoenolpyruvate to OAA; and/or a gene encoding malate dehydrogenase that catalyzes the conversion of pyruvate to malate; a gene encoding malate dehydrogenase that catalyzes the conversion of OAA to malate; a gene encoding malate thiokinase to convert malate to malyl coenzyme A; and a gene encoding malyl coenzyme A lyase to convert malyl coenzyme A to glyoxylate and acetyl coenzyme A. In one embodiment, the gene encoding malate dehydrogenase encodes for a modified malate dehydrogenase that catalyzes the conversion of pyruvate to malate or OAA to malate but does not catalyze the reverse reaction of malate to pyruvate or malate to OAA or shows reduced conversion of malate to pyruvate or malate to OAA. The modified malate dehydrogenase can be a naturally occurring variant or an engineered variant.

In another embodiment, the reverse glyoxylate shunt based pathway of the present disclosure comprises carboxylating phosphoenol pyruvate (PEP) and/or pyruvate to oxaloacetate (OAA); converting malate to malyl-Coenzyme A (CoA) and converting malyl-CoA to glyoxylate and acetyl-CoA; wherein the reverse glyoxylate shunt pathway does not comprise converting OAA to malate. Accordingly, in one embodiment, provided herein is a recombinant microorganism that comprises a gene encoding pyruvate carboxylase to convert pyruvate to OAA, and/or a gene encoding phosphoenolpyruvate carboxylase to convert phosphoenolpyruvate to OAA, and/or a gene encoding phosphoenolpyruvate carboxykinase to convert phosphoenolpyruvate to OAA; a gene encoding malate thiokinase to convert malate to malyl coenzyme A, and a gene encoding malyl coenzyme A lyase to convert malyl coenzyme A to glyoxylate and acetyl coenzyme A, wherein the microorganism does not comprise a gene encoding malate dehydrogenase that catalyzes the conversion of OAA to malate or comprises a loss-of-function mutation in the gene encoding malate dehydrogenase that catalyzes the conversion of OAA to malate.

In another embodiment, the reverse glyoxylate shunt based pathway of the present disclosure comprises carboxylating phosphoenol pyruvate (PEP) and/or pyruvate to oxaloacetate (OAA); carboxylating pyruvate to malate; converting malate to malyl-Coenzyme A (CoA) and converting malyl-CoA to glyoxylate and acetyl-CoA; wherein the reverse glyoxylate shunt pathway does not comprise converting OAA to malate. Accordingly, in one embodiment, provided herein is a recombinant microorganism that comprises a gene encoding pyruvate carboxylase to convert pyruvate to OAA, and/or a gene encoding phosphoenolpyruvate carboxylase to convert phosphoenolpyruvate to OAA, and/or a gene encoding phosphoenolpyruvate carboxykinase to convert phosphoenolpyruvate to OAA; a gene encoding malate dehydrogenase that catalyzes the conversion of pyruvate to malate; a gene encoding malate thiokinase to convert malate to malyl coenzyme A, and a gene encoding malyl coenzyme A lyase to convert malyl coenzyme A to glyoxylate and acetyl coenzyme A, wherein the microorganism does not comprise a gene encoding malate dehydrogenase that catalyzes the conversion of OAA to malate or comprises a deletion or loss-of-function mutation in the gene encoding malate dehydrogenase that catalyzes the conversion of OAA to malate.

Glyoxylate produced by the reverse glyoxylate shunt and other pathways can be converted to glycolic acid and/or glycine. To increase the production of GA, the recombinant microorganism of any one of the embodiments disclosed herein may comprise a gene encoding NAD(P)H-dependent glyoxylate reductase that catalyzes the conversion of glyoxylate to glycolate. In one embodiment, the recombinant microorganism may over-express NAD(P)H-dependent glyoxylate reductase to increase the yield of GA. In another embodiment, the recombinant microorganism of any one of the embodiments disclosed herein may comprise a gain of function mutation in the gene encoding NAD(P)H-dependent glyoxylate reductase so that the activity of NAD(P)H-dependent glyoxylate reductase is increased compared to a microorganism lacking such mutation.

The term "NAD(P)H dependent" as used herein encompasses both NADH-dependent as well as NADPH-dependent enzymatic activity.

To increase the production of glycine, the recombinant microorganism of any one of the embodiments disclosed herein may comprise one or more genes encoding enzymes that catalyze the glyoxylate to glycine conversion. For example, the recombinant microorganism of any one of the embodiments disclosed herein may comprise a gene encoding alanine-glyoxylate aminotransferase, a gene encoding glycine dehydrogenase, a gene encoding glycine transaminase, a gene encoding serine-glyoxylate transaminase, and/or a gene encoding glycine oxidase. In one embodiment, the recombinant microorganism of any one of the embodiments disclosed herein may over-express one or more of these genes to increase the yield of glycine. In another embodiment, the recombinant microorganism of any one of the embodiments disclosed herein may comprise a gain of function mutation in one or more of the above-described genes encoding glycine-producing enzymes so that the activity of these genes is increased compared to a microorganism lacking such mutation.

In one embodiment, the recombinant microorganisms of the present disclosure does not produce malonyl-CoA via the rGS pathway.

The recombinant microorganisms of the present invention comprise a gene encoding malate dehydrogenase that catalyzes the carboxylation of pyruvate to malate and/or the reduction of OAA to malate. In one embodiment, the malate dehydrogenase that catalyzes the conversion of OAA to malate is from, but not limited to, the Enzyme Class (E.C.) 1.1.1.37. In another embodiment, the malate dehydrogenase that catalyzes the conversion of malate to OAA is from the EC 1.1.5.4. The malate dehydrogenase that catalyzes the conversion of malate to OAA is also known as malate: quinone oxidoreductase. In certain embodiments, the malate dehydrogenase that catalyzes the carboxylation of pyruvate to malate is from, but not limited to, the Enzyme Class (E.C.) 1.1.1.38, E.C. 1.1.1.39, or E.C. 1.1.1.40.

In one embodiment, the recombinant microorganisms of the present disclosure comprise a gene encoding malate dehydrogenase, wherein the malate dehydrogenase can catalyze the conversion of pyruvate to malate and/or OAA to malate but does not catalyze or catalyzes with reduced efficiency the reverse reaction from malate to pyruvate or malate to OAA. In one embodiment, the recombinant microorganisms of the present disclosure comprise a gene encoding malate dehydrogenase, wherein the malate dehydrogenase can catalyze the conversion of oxaloacetate to malate but not the conversion of pyruvate to malate or malate to pyruvate. In one embodiment, the gene encoding malate dehydrogenase may comprise a mutation that results in a partial or complete inhibition of the malate dehydrogenase activity that catalyzes the conversion of oxaloacetate to malate or malate to oxaloacetate or pyruvate to malate or malate to pyruvate.

In exemplary embodiments, the gene encoding malate dehydrogenase that catalyzes the carboxylation of pyruvate to malate is from, but not limited to, bacteria, such as *Escherichia* (e.g., gene maeA or maeB from *E. coli*), *Pseudomonas*, *Bacillus* (e.g., gene maeA from *Bacillus subtilis*), *Rhizobium* (e.g., gene dme from *R. melilote*), *Mycobacterium* (e.g., gene mez from *Mycobacterium tuberculosis*), *Salmonella* (e.g., gene maeB from; or from yeast such as (e.g., gene mae1 from *S. cerevisiae*); or from plant (e.g., gene nad-me1 or nad-me2 or nad-me3 or nadp-me1 or nadp-me2 from *Arabidopsis thaliana*).

In exemplary embodiments, the gene encoding the malate dehydrogenase that catalyzes the conversion of oxaloacetate to malate is from, but not limited to, bacteria, such as *Escherichia* (e.g., gene mdh from *E. coli*), *Corynebacterium*, *Streptomyces* (e.g., gene mdh from *S. coelicolor*); or from yeast, such as *Saccharomyces* (e.g., gene mdh1/2/3 from *S. cerevisiae*); or from plant, such as *Arabidopsis*. In another embodiment, the gene encoding the malate dehydrogenase that catalyzes the conversion of malate to oxaloacetate (also known as malate:quinone oxidoreductase) is from, but not limited to, *Escherichia* (e.g., gene mqo from *E. coli*), *Pseudomonas* (e.g., gene mqo from *P. putida*) or *Bacillus* sp.

Malate is converted to malyl CoA by malate thiokinase activity (also known as malate-CoA ligase or malyl-CoA synthetase) or by succinyl-CoA ligase activity (also known as succinyl-CoA synthetase). In one embodiment, the malate thiokinase is from, but not limited to, EC 6.2.1.4, EC 6.2.1.5, EC 6.2.1.9 or EC 6.2.1.-. In an exemplary embodiment, the gene encoding malate thiokinase or succinyl-CoA ligase is from bacteria such as *Escherichia* (e.g., gene sucCD-2 from *E. coli*), *Thermus thermophiles*, *Clostridium kluyveri*, *Bacillus subtilis*, *Methanocaldococcus* (e.g., gene mtkAB or sucCD from *M. jannaschii*), *Staphylococcus aureus*, *Methanothermobacter thermautotrophicus*, *Pseudomonas*, *Methylococcus* sp., *Methylobacterium* (e.g., gene mtkAB or sucCD from *M. extorquens*), *Nitrosomonas europaea*, *Granulibacter bethesdensis*, *Mesorhizobium japonicum*, *Hyphomicrobium methylovorum*, *Hyphomicrobium denitrificans*, *Methylococcus capsulatus*, *Rhodobacteraceae bacterium* or *Rhizobium*. In one embodiment, the malate thiokinase or the succinyl-CoA ligase has high activity and/or specificity to malate and low activity and/or specificity to other compounds, such as succinate. This can be achieved via enzyme engineering.

Malyl CoA is converted into glyoxylate and acetyl-CoA by malyl CoA lyase. In one embodiment, malyl coA lyase is from, but not limited to, EC 4.1.3.24 or EC 4.1.3.25. In an exemplary embodiment, the gene encoding malyl-CoA lyase is from *Methylobacterium* (e.g., gene mclA from *M. extorquens*), *Methylobacterium extorquens*, *Thalassiobus activus*, *Rhodobacter* (e.g., gene mcl1 from *R. sphaeroides*), *Roseobacter litoralis*, *Streptomyces*, *Streptococcus*, *Mycobacterium* (e.g., gene mcl1 from *M. smegmatis*), *Hyphomicrobium methylovorum*, *Roseobacter* (e.g., gene mcl1 *R. litoralis*), *Nitrosomonas europaea*, *Cupriavidus necator*, *Chloroflexus* (e.g., gene mcl from *C. aurantiacus*), *Nereida* (e.g., gene mcl1 from *N. ignava*), *Hyphomicrobium denitrificans*, *Rhodococcus fascians*.

The carboxylation of PEP to oxaloacetate is catalyzed by phosphoenolpyruvate carboxylase or phosphoenolpyruvate carboxykinase. In one embodiment, the PEP carboxylase is from, but not limited to, EC 4.1.1.31. In an exemplary embodiment, the gene encoding PEP carboxylase is from, but not limited to, bacteria, such as *Escherichia* (e.g., gene ppc from *E. coli*), *Rhodothermus* (e.g., gene ppc or pepC from *R. marinus*), *Corynebacterium*, *Salmonella*, *Hyphomicrobium*, *Streptococcus*, *Streptomyces*, *Pantoea*, *Bacillus*, *Clostridium*, *Pseudomonas*, *Rhodopseudomonas*, *Methanothermobacter* (e.g., gene ppcA from *M. thermautotrophicus*); plant, such as *Saccharum* hybrid, *Glycine* (e.g., gene ppc from *G. max*), *Nicotiana tabacum*, *Amaranthus hypochondriacus*, *Triticum aestivum*, *Medicago sativa*, *Zea mays*

(e.g., gene pep1) or *Arabidopsis* (e.g., genes ppc1 or ppc2 or ppc3 from *A. thaliana*); archaea or yeast. In one embodiment, phosphoenolpyruvate carboxykinase is from, but not limited to, EC 4.1.1.32 or EC 4.1.1.49. In an exemplary embodiment, the encoding PEP carboxykinase is from, but not limited to, bacteria such as *Escherichia* (e.g., gene pck or pckA from *E. coli*), *Selenomonas* (e.g., gene pckA from *S. ruminantium*), *Salmonella* (e.g., gene pckA from *S. typhimurium*), *Mycobacterium, Pseudomonas, Rhodopseudomonas, Clostridium, Thermococcus, Streptococcus* (e.g., gene pck or pckA from *S. bovis*), *Ruminococcus* (e.g., pck or pckA from *R. albus* or *R. flavefaciens*) *Actinobacillus* (e.g., gene pckA from *A. succinogenes*), *Bacillus, Ruminiclostridium thermocellum, Klebsiella, Thermus*; yeast, such as *Saccharomyces* (e.g., gene pck1 or pepc or ppc1 from *S. cerevisiae*); or *Trypanosoma* (e.g., gene from *T. brucei*).

The carboxylation of pyruvate to oxaloacetate is catalyzed by pyruvate carboxylase. In one embodiment, pyruvate carboxylase is from, but not limited to, EC 6.4.1.1. In an exemplary embodiment, the gene encoding pyruvate carboxylase is from bacteria such as *Bacillus* (e.g., gene pyc from *B. subtilis*), *Candida* (e.g., gene pyc1 from *C. glabrata*), *Cupriavidus* (e.g., gene pyc1 from *C. necator*), *Mycobacterium* (e.g., gene pyc from *M. smegmatis*), *Corynebacterium* (e.g., gene pyc from *C. glyciniphilum*), *Nocardia* (e.g., gene pyc1 from *N. nova*); or yeast such as *Saccharomyces* (e.g., gene pyc1 and pyc2 from *S. cerevisiae*), *Pichia* (e.g., pyc from *P. pastoris*); or *Caenorhabditis* (e.g., pyc from *C. elegans*); or from *Homo sapiens*.

Glyoxylate can be reduced by NADH-glyoxylate reductase or by NADPH-glyoxylate reductase to produce glycolate. In one embodiment, NADH-glyoxylate reductase is from EC 1.1.1.26. In one embodiment, NADPH-glyoxylate reductase is from EC 1.1.1.79. In an exemplary embodiment, the gene encoding NADH or NADPH-dependent glyoxylate reductase activity is the gene "ycdW/ghrA" and/or "yiaE" in *E. coli*, gene "GLYR1" from *A. thaliana*, gene "GOR1" from *S. cerevisiae*, and "gyaR" from *Thermococcus litoralis*. In some embodiments, the cofactor preference (NADH or NADPH) of the enzyme can be altered through enzyme engineering. In some embodiments, the enzyme NADPH-dependent glyoxylate reductase, codified by the genes "ycdW/ghrA" or "yiaE" from *E. coli* or "GLYR1" from *A. thaliana*, is engineered to become a NADH-dependent glyoxylate reductase enzyme, accepting NADH as well as the naturally enzyme accepted the cofactor NADPH, and still showing the same performance for the glyoxylate to glycolate conversion (i.e., cofactor switch without compromising its kinetic parameters for the desired reaction).

In one embodiment, the production of glyoxylate and ultimately the production of glycolic acid and/or glycine can be increased by co-utilization of the rGS pathway with the glyoxylate shunt (GS) pathway. For example, the acetyl-CoA generated in the rGS pathway, i.e. from the activity of the malyl-CoA lyase on malyl-CoA, can be reincorporated into the metabolic pathway in order to further increase the production of glyoxylate: i.e., by entering the GS pathway by combining with OAA to produce citrate, citrate is converted to isocitrate, isocitrate is converted to succinate and glyoxylate. The succinate produced by the GS pathway can be converted to malate via fumarate and the malate produced via this route can enter the rGS pathway where it is converted to malyl coenzyme A, which is further converted to glyoxylate and acetyl coenzyme A.

In recombinant microorganisms of the present invention, the rGS pathway may run first followed by the GS pathway or the GS pathway may run first followed by the rGS pathway.

In one embodiment of the co-utilization of the rGS and GS pathways, PEP can be converted to OAA (PEP carboxylase or PEP carboxykinase) and/or pyruvate can be converted to OAA (pyruvate carboxylase) or to malate (malate dehydrogenase); OAA can be converted to malate (malate dehydrogenase); malate can be converted to malyl-CoA (malate thiokinase); malyl-CoA can be converted to glyoxylate and acetyl-CoA (malyl-CoA lyase); acetyl-CoA can combine with OAA to form citrate (citrate synthase); citrate can be converted to cis-aconitate (citrate hydro-lyase); cis-aconitate can be converted to isocitrate (D-threo-isocitrate hydro-lyase or aconitase); isocitrate can be converted to succinate and glyoxylate (isocitrate lyase); succinate can be converted to fumarate (succinate dehydrogenase); and fumarate can be converted to malate (fumarase). Malate can re-enter the rGS pathway and can be converted to malyl-CoA.

In another embodiment of the co-utilization of the rGS and GS pathways, PEP can be converted to OAA (PEP carboxylase or PEP carboxykinase) and/or pyruvate can be converted to OAA (pyruvate carboxylase) or to malate (malate dehydrogenase); OAA can be converted to citrate by combining with acetyl-CoA (citrate synthase); citrate can be converted to cis-aconitate (citrate hydro-lyase); cis-aconitate can be converted to isocitrate (D-threo-isocitrate hydro-lyase or aconitase); isocitrate can be converted to succinate and glyoxylate (isocitrate lyase); succinate can be converted to fumarate (succinate dehydrogenase); fumarate can be converted to malate (fumarase); and malate can be converted to malyl-CoA (malate thiokinase) and malyl-CoA can be converted to glyoxylate and acetyl-CoA. In this embodiment, OAA may be exclusively combined with acetyl-CoA to form citrate (i.e. by blocking the conversion of OAA to malate, e.g. by inactivating the enzyme malate dehydrogenase that catalyzes the conversion of OAA to malate) or part of it may be converted to malate.

The recombinant microorganism of any one of the embodiments disclosed herein may comprise genes encoding enzymes involved in the GS pathway. In one embodiment, the recombinant microorganism comprises (a) a gene encoding citrate synthase to convert acetyl-coA and OAA to citrate; (b) a gene encoding citrate hydro-lyase to convert citrate to cis-aconitate; (c) a gene encoding D-threo-isocitrate hydro-lyase or aconitase to convert cis-aconitate to isocitrate; (d) a gene encoding isocitrate lyase to convert isocitrate to succinate and glyoxylate; (e) a gene encoding succinate dehydrogenase to convert succinate to fumarate; and (f) a gene encoding fumarase to convert fumarate to malate.

The glyoxylate produced by the GS and rGS pathway could be converted to malate by malate synthase. However, this reaction would decrease the yield of glyoxylate and thereby decrease the production of GA and glycine. Accordingly, in one embodiment, the recombinant microorganisms described herein may comprise a loss-of-function mutation in the gene encoding malate synthase. The loss-of-function mutations as referred to herein may result in a complete or partial loss of function. The loss of function mutation may also include a complete deletion of the gene of interest. In an exemplary embodiment, the genes encoding malate synthase that may be inactivated according to the present disclosure include aceB and/or glcB in *E. coli* or DAL7 and MLS1 in *S. cerevisiae*.

In one embodiment, depending on the amount of excess NADH in a given pathway, the flux ratio of co-utilized rGS and GS is adapted to obtain lowest possible net NADH production for optimal yield.

One or more genes disclosed herein encoding the enzymes of interest may be present endogenously, may be inserted into the genome of the microorganism and/or expressed via one or more vectors (e.g., plasmids, cosmids, viral vectors, etc.) introduced into the microorganism. A high level of enzyme activity can be obtained by using or inserting one or several copies of the genes on the genome that can be introduced by methods of recombination known to a person of ordinary skill in the field. For expression via vectors, different types of vectors such as plasmids that differ with respect to their origin of replication and thus their copy number in the cell can be used. Exemplary plasmids for expressing the genes of interests include, but are not limited to, pSK bluescript II, pSC101, RK2, pACYC, pRSF1010, etc). The genes encoding the enzymatic polypeptides may be expressed using promoters with different strength that may or may not to be induced by inducer molecules. Examples of the promoters include Ptrc, Ptac, Plac, the lambda promoter cI or other promoters known to a person of ordinary skill in the field. Expression of the genes may also be boosted by elements stabilizing the corresponding messenger RNA (Carrier and Keasling (1998) Biotechnol. Prog. 15, 58-64) or the protein (e.g. GST tags, Amersham Biosciences).

In one embodiment, the endogenous glyoxylate shunt (GS) pathway and/or other central metabolic pathways in the recombinant microorganism may be modified, for example, by avoiding competing routes or by-products formation and bypassing carbon loss reactions to maximize the carbon flow to the biosynthesis of glycolic acid and/or glycine through the reverse glyoxylate shunt. For example, in one embodiment, the recombinant microorganism comprising the rGS pathway may be modified to delete or attenuate the expression of at least one gene encoding an enzyme selected from the group consisting of:
(a) malate synthase (e.g. genes aceB and/or glcB in *E. coli* or genes DAL7 and MLS1 in *S. cerevisiae*);
(b) isocitrate dehydrogenase (e.g. gene icd in *E. coli* or genes IDP2 and IDH1/2 in *S. cerevisiae*);
(c) pyruvate dehydrogenase (e.g. genes pdhc and/or lpd in *E. coli*), pyruvate oxidase (e.g. gene poxB in *E. coli*) and/or pyruvate formate-lyase (e.g. gene pfl in *E. coli*); and
(d) pyruvate kinase (e.g. genes pykA and/or pykF in *E. coli*).

In some embodiments, endogenous glyoxylate consuming routes in the recombinant microorganism comprising the rGS pathway may be deleted or attenuated to further increase the yield of glycolic acid and/or glycine. For example, in one embodiment, the recombinant microorganism comprising the rGS pathway is modified to delete or attenuate the expression of or inhibit the activity of at least one gene selected from the group consisting of:
(a) a gene encoding glyoxylate carboligase (e.g. gene gcl in *E. coli*);
(b) a gene encoding 2-oxo-4-hydroxyglutarate aldolase (e.g. edA in *E. coli*);
(c) a gene encoding glycoaldehyde reductase (e.g. gene fucO and/or gldA in *E. coli*);
(d) a gene encoding glycolate oxidase (e.g., genes glcD, glcE, glcF and glcG in *E. coli*);
(e) a gene encoding a repressor of isocitrate lyase (e.g., gene iclR in *E. coli*); and
(f) a gene encoding glucose-6-phosphate isomerase (e.g., gene pgi in *E. coli*).

Attenuation of gene expression or inhibition of the activity of the enzyme encoded by the gene can be done by introducing mutations into the gene that reduce the activity of the corresponding enzyme or by replacing the natural promoter by a low strength promoter or by using an agent that destabilizes the corresponding messenger RNA or the protein. Attenuation of gene expression or inhibition of the activity of the enzyme encoded by the gene can be done by deleting the corresponding gene from the microorganism using techniques known in the art.

In one embodiment, the recombinant microorganism of the present disclosure expresses a set of genes encoding:
(a) malate dehydrogenase that catalyzes the conversion of pyruvate to malate;
(b) malate thiokinase that catalyzes the conversion of malate to malyl-CoA; and
(c) malyl CoA lyase that catalyzes the conversion of malyl-CoA to glyoxylate and acetyl-CoA;
(d) optionally phosphoenolpyruvate carboxylase that catalyzes the conversion of PEP to oxaloacetate, and/or phosphoenolpyruvate carboxykinase that catalyzes the conversion of PEP to oxaloacetate, and/or pyruvate carboxylase that catalyzes the conversion of pyruvate to oxaloacetate;
and comprises at least one modification selected from the group consisting of:
(a) deletion or attenuation of a gene encoding malate synthase;
(b) deletion or attenuation of a gene encoding isocitrate dehydrogenase;
(c) deletion or attenuation of a gene encoding pyruvate dehydrogenase, pyruvate oxidase and/or pyruvate formate-lyase;
(d) deletion or attenuation of a gene encoding malate dehydrogenase that catalyzes the conversion of oxaloacetate to malate or malate to oxaloacetate (malate:quinone oxidoreductase); and
(e) deletion or attenuation of a gene encoding pyruvate kinase.

In one embodiment, the recombinant microorganism of the present disclosure expresses a set of genes encoding:
(a) phosphoenolpyruvate carboxylase that catalyzes the conversion of PEP to oxaloacetate and/or phosphoenolpyruvate carboxykinase that catalyzes the conversion of PEP to oxaloacetate and/or pyruvate carboxylase that catalyzes the conversion of pyruvate to oxaloacetate and/or malate dehydrogenase that catalyzes the conversion of pyruvate to malate;
(b) malate thiokinase;
(c) malyl CoA lyase; and
(d) optionally malate dehydrogenase that catalyzes the conversion of oxaloacetate to malate;
and comprises at least one modification selected from the group consisting of:
(a) deletion or attenuation of a gene encoding malate synthase;
(b) deletion or attenuation of a gene encoding isocitrate dehydrogenase;
(c) deletion or attenuation of a gene encoding pyruvate dehydrogenase, pyruvate oxidase and/or pyruvate formate-lyase;
(d) deletion or attenuation of a gene encoding malate dehydrogenase that catalyzes the conversion of malate to pyruvate; and
(e) deletion or attenuation of a gene encoding pyruvate kinase.

In another embodiment, the recombinant microorganism comprising the rGS pathway expresses a set of genes encoding:
(a) malate dehydrogenase that catalyzes the conversion of pyruvate to malate;
(b) malate thiokinase that catalyzes the conversion of malate to malyl-CoA; and
(c) malyl-CoA lyase that catalyzes the conversion of malyl-CoA to glyoxylate and acetyl-CoA;
(d) optionally phosphoenolpyruvate carboxylase that catalyzes the conversion of PEP to oxaloacetate, and/or phosphoenolpyruvate carboxykinase that catalyzes the conversion of PEP to oxaloacetate, and/or pyruvate carboxylase that catalyzes the conversion of pyruvate to oxaloacetate;
and comprises at least one modification selected from the group consisting of:
(a) deletion or attenuation of a gene encoding malate synthase;
(b) deletion or attenuation of a gene encoding isocitrate dehydrogenase;
(c) deletion or attenuation of a gene encoding pyruvate dehydrogenase, pyruvate oxidase and/or pyruvate formate-lyase;
(d) deletion or attenuation of the gene encoding malate dehydrogenase that catalyzes the conversion of oxaloacetate to malate or malate to oxaloacetate;
(e) deletion or attenuation of a gene encoding pyruvate kinase;
(f) deletion or attenuation of a gene encoding glyoxylate carboligase;
(g) deletion or attenuation of a gene encoding 2-oxo-4-hydroxyglutarate aldolase;
(h) deletion or attenuation of a gene encoding glycoaldehyde reductase;
(i) deletion or attenuation of a gene encoding glycolate oxidase; and
(j) deletion or attenuation of a gene encoding a repressor of isocitrate lyase.

In one embodiment, the overall stoichiometry of the glycolic acid production using the rGS pathway and/or modifications in one or more of the genes describe above is: Glucose+2 $CO_2$→2 GA+2 acetyl-CoA−2 NAD(P)H−2 ATP. In another embodiment, the overall stoichiometry of the glycolic acid production using the rGS pathway and/or modifications in one or more of the genes describe above is: Glucose+2 $CO_2$+2 NAD(P)H+2 ATP→4 GA+2 Quinol.

Redox balance is important in fine-tuning of metabolic pathways to achieve maximum product yield potential. Imbalance in the redox state, e.g., imbalanced intracellular pool of NADPH and NADH co-factors, imbalanced net ATP, and/or shortage of reducing agents, can result in a lower product yield and generation of undesired by-products. The present disclosure encompasses recombinant microorganisms in which the redox balance is fine-tuned and methods of use thereof. For example, the recombinant microorganisms of any one of the embodiments disclosed herein may comprise genes encoding transhydrogenases and/or NAD kinases to increase the intracellular concentrations of NADH and/or NADPH thereby reaching increased product yield. In an exemplary embodiment, the recombinant microorganisms of any one of the embodiments disclosed herein may comprise genes encoding transhydrogenases such as "pntAB" and/or "udhA" from E. coli and/or a gene encoding NAD kinase such as "yfjB" from E. coli. The expression of these genes can, for example, increase the intracellular concentration of NADPH thereby increasing the activity of NADPH-dependent glyoxylate reductase to facilitate the conversion of glyoxylate to glycolate.

The use of transhydrogenases (e.g. gene pntAB and udhA in E. coli) and/or NAD kinases (e.g. gene yfjB in E. coli) to increase intracellular concentrations of NADH or NADPH has been described in US20140335578, Cui et al., Microbial Cell Factories 2014, 13:21, and Shi et al., Metabolic Engineering 16 (2013)1-10; all of which are incorporated by reference herein.

In one embodiment, reducing agents such as sulfur-containing compounds (e.g., sulfites, sulfur dioxide and cystein) and/or hydrogen can be added to the culture medium as an additional reducing power source in order to adjust the redox balance of the metabolic pathway to increase the product yield. In another embodiment, an exogenous source of hydrogen or other additional source of electrons/NAD(P)H may be added to the culture medium for metabolic pathways with negative balance of NADH or NADPH.

In certain embodiments, a gene encoding malate: quinone oxidoreductase (also called malate dehydrogenase) is inactivated by deletion or attenuation in the recombinant microorganisms comprising the reverse GS pathway.

The rGS pathway of the present disclosure can be combined with known GA and glycine producing pathways. Currently known GA and/or glycine producing pathways include a serine/hydroxypyruvate pathway described in U.S. Pat. No. 8,911,978; a glyoxylate shunt (GS) pathways described in U.S. Pat. Nos. 9,034,615 and 8,945,888, PCT Publication No. WO 2016/193540 and U.S. Pre-Grant Publication No. 2014/0295510; a D-erythrose based pathway described in PCT Publication No. WO 2015/181074; and a pentose derivative to glycolaldehyde based pathways described in PCT Publication Nos. WO 2017/059236 and WO 2016/79440 and U.S. Pre-grant Publication Nos. US 2016/0076061 and US 2015/0147794. All these pathways generate excess NADH and release excess $CO_2$, i.e., these pathways do not reach the thermodynamic possible maximum yield. By combining these known GA and glycine producing pathways with the rGS pathway of the present disclosure, the yield of GA and/or glycine can be increased substantially.

Yield of GA using some of the previously published pathways:

Serine/Hydroxypyruvate Pathways:
1 Glucose→→2 GA+2 $CO_2$+6 NADH+0 ATP; y=0.84 g/g, 49% of Y(max)=1.70 g/g GS Pathway:
Glucose→2 GA+2 $CO_2$+4 NADH+2 quinol+2 ATP; y=0.84 g/g, 49% of Y(max)=1.70 g/g Pentose Derivative Pathways, with GS:
Xylose→2 GA+1 $CO_2$+3 NADH+1 quinol+0 ATP; y=1.01 g/g, 59% of Y(max)=1.71 g/g Erythrose Pathway:
Glucose→3 GA+2 NADH+1 quinol−1 ATP, y=1.27 g/g, 75% of Y(max)=1.70 g/g.

By combining or co-utilizing the above pathways with the rGS pathway of the present invention, the yield of GA can be substantially increased. For example, in certain embodiments, a co-utilization of the known GA producing pathways with the rGS pathway of the invention could provide increased GA yield as follows:

GS and rGS Pathway:
Glucose+2/3 $CO_2$+2/3 ATP→10/3 GA+2 quinol; y=1.41 g/g, 83% of Y(max)=1.69 g/g GS and rGS Pathway (No Flux on Malate Dehydrogenase):
Glucose+2 $CO_2$+2 NAD(P)H→4 GA+2 quinol; y=1.69 g/g, 100% of Y(max)=1.69 g/g Pentose Derivative Pathways, with GS and rGS:
Xylose+$CO_2$+1 ATP→3 GA+1 quinol; y=1.52 g/g, 90% of Y(max)=1.69 g/g Serine, GS and rGS Pathways:
Glucose+$CO_2$+1.5 ATP→3.5 GA+1.5 quinol; y=1.48 g/g, 88% of Y(max)=1.69 g/g.

In one embodiment, the reverse glyoxylate shunt pathway of the present invention utilizes NADH and $CO_2$ generated by other glycolic acid glycine producing pathways and/or glycoaldehyde generating pathway, and/or $CO_2$ and/or $HCO_3^-$ and/or other carbon source exogenously provided, thereby increasing the yield potential. For example, in one embodiment, the reverse glyoxylate shunt pathway of the present disclosure utilizes the NADH and $CO_2$ generated by a serine/hydroxypyruvate-based pathway described in U.S. Pat. No. 8,911,978. In another embodiment, the reverse glyoxylate shunt pathway utilizes the NADH and $CO_2$ generated by a glyoxylate shunt pathway described in U.S. Pat. Nos. 9,034,615 and 8,945,888, PCT Publication No. WO 2016/193540 and U.S. Pre-Grant Publication No. 2014/0295510. In yet another embodiment, the reverse glyoxylate shunt pathway utilizes the NADH and $CO_2$ generated by a D-erythrose and pentose derivative to glycoaldehyde based pathways described in a PCT Publication Nos. WO 2015/181074, WO 2017/059236, and WO 2016/79440 and U.S. Pre-grant Publication Nos. US 2016/0076061 and US 2015/0147794.

The recombinant microorganisms of the present disclosure include a bacterium, yeast or a fungus. In certain embodiments, the microorganism is selected from, but not limited to, Enterobacteriaceae, Clostridiaceae, Bacillaceae, Streptomycetaceae, Corynebacteriaceae and Saccharomycetaceae. In one embodiment, the microorganism is a species of *Escherichia, Clostridium, Bacillus, Klebsiella, Pantoea, Salmonella, Lactobacillaceae, Corynebacterium* or *Saccharomyces*. In one embodiment, the microorganism is *Escherichia coli* or *Corynebacterium glutamicum* or *Clostridium acetobutylicum* or *Bacillus subtilis* or *Saccharomyces cerevisiae*.

Glycine Production

Glyoxylate produced using any one of the pathways described above can be converted to glycine using various enzymes. For example, glycine can be produced from glyoxylate through transamination with alanine, for e.g., by alanine-glyoxylate aminotransferase (EC 2.6.1.44). Usually, natural pathways utilize glutamate as an amino group donor in another transamination reaction to replenish alanine from pyruvate catalyzed by alanine transaminase (EC 2.6.1.2). Glutamate itself can be replenished from the resulting 2-oxoglutarate by fixing the common nitrogen source $NH_3$ into it, requiring a NAD(P)H glutamate synthase (EC 1.4.1.13, EC 1.4.1.14). The overall stoichiometry is glyoxylate+NH3+1 NAD(P)H→glycine. Other enzymes that can facilitate the conversion of glyoxylate to glycine include glycine dehydrogenase (E.C. 1.4.1.10), glycine transaminase (E.C. 2.6.1.4), serine-glyoxylate transaminase (E.C. 2.6.1.45) and glycine oxidase (E.C. 1.4.3.19). Accordingly, the recombinant microorganism of any one of the embodiments disclosed herein may comprise one or more gene selected from the group consisting of: a gene encoding alanine-glyoxylate aminotransferase (EC 2.6.1.44), a gene encoding glycine dehydrogenase (E.C. 1.4.1.10), a gene encoding glycine transaminase (E.C. 2.6.1.4), a gene encoding serine-glyoxylate transaminase (E.C. 2.6.1.45) and/or a gene encoding glycine oxidase (E.C. 1.4.3.19).

In an exemplary embodiment, a gene encoding glycine dehydrogenase (EC 1.4.1.10) can be from *Mycobacterium* sp. (e.g. *Mycobacterium tuberculosis, Mycobacterium smegmatis*), *Pseudomonas* sp., *Xanthobacter* sp., or *Bacillus* sp.

In an exemplary embodiment, a gene encoding glycine transaminase (EC 2.6.1.4): can be from *Rhodopseudomonas palustris, Lactobacillus* sp., *Hydrogenobacter* sp., *Rattus* sp., or *Rhodopseudomonas* sp.

Yield of glycine using previously published or natural pathways:

Glyoxylic Acid Using Glyoxylate Shunt:
glucose→2 glyoxylic acid+6 NADH+2 quinol+2 ATP; y=0.82 g/g, 33% of Y(max)=2.51 g/g Glycine Via Glyoxylate Transamination:
glucose+2 $NH_3$→2 glycine+4 NADH+2 quinol+2 ATP; y=0.701 g/g(glucose+2$NH_3$), 58% of Y(max)=1.20 g/g Glycine Via Serine Decarboxylation:
glucose+2 THF+2 $NH_3$→2 glycine+2 M-THF+2 NADH+0 ATP; y=0.701 g/g(glucose+2$NH_3$).

Yield of glycine by co-utilizing the known pathways with the rGS pathway of the invention:

Pentose Derivative Pathways, GS and rGS, Using Glyoxylate Transamination:
xylose+3 $NH_3$+$CO_2$+1 ATP→3 glycine+1 quinol; y=1.12 g/g(xylose+3$NH_3$), 90% of Y(max)=1.25 g/g GS and rGS, Using Glyoxylate Transamination:
glucose+10/3 $NH_3$+2/3 $CO_2$+2/3 ATP→10/3 glycine+2 quinol; y=1.06 g/g(glucose+10/3 $NH_3$), 85% of Y(max)=1.24 g/g GS and rGS, Using Glyoxylate Transamination (No Flux on Malate Dehydrogenase):
Glucose+4 $NH_{3+2}$ $CO_2$+2 NAD(P)H→4 glycine+2 quinol; y=1.24 g/g, 100% of Y(max)=1.24 g/g Serine, GS and rGS Pathways:
glucose+3.5 $NH_3$+$CO_2$+1.5 ATP→3.5 glycine+1.5 quinol; y=1.10 g/g(glucose+3.5$NH_3$), 89% of Y(max)=1.24 g.

In one embodiment, the level of expression of at least one gene selected from the group consisting of:
(a) a gene encoding alanine-glyoxylate aminotransferase;
(b) a gene encoding glycine dehydrogenase;
(c) a gene encoding glycine transaminase;
(d) a gene encoding serine-glyoxylate transaminase;
(e) a gene encoding glycine oxidase;
(f) a gene encoding alanine transaminase; and
(g) a gene encoding NAD(P)H-dependent glutamate synthase;
is increased in the recombinant microorganism comprising the rGS pathway to increase the production of glycine. In another embodiment, one or more of these genes may comprise a gain of function mutation that increases the activity of the enzymes encoded by these genes.

The glyoxylate producing recombinant microorganisms of the present invention may also co-produce glycolic acid and glycine.

In some embodiments, microorganisms of the present invention do not produce isopropyl alcohol. In one embodiment, microorganisms of the present invention do not produce serine and/or glutamic acid via the reverse glyoxylate shunt pathway. In some embodiments, microorganisms of the present invention may not comprise one or more enzymes that convert glycine to serine. For example, in one embodiment, the microorganisms of the present invention may comprise a loss of function mutation in the gene encoding serine hydroxymethyltransferase. In another embodiment, the microorganisms may not comprise glycine consuming pathways.

The microorganisms comprising the reverse glyoxylate pathway show increased production of glycolic acid and glycine. In one embodiment, the microorganisms of the present disclosure lack pathways that convert glycolic acid and/or glycine into other products or intermediates.

Co-Utilization of the rGS Pathway with Other Glycolic Acid Producing Pathways

In certain embodiments, the recombinant microorganisms comprising the reverse glyoxylate shunt pathway utilizes NADH and $CO_2$ generated by other glycolate and/or glycine generating pathways and/or other carbon source ($CO_2$ and/or $HCO_3^-$ and/or other carbonates) exogenously provided. For example, in one embodiment, the rGS pathway of the present invention can be co-utilized with pentose derivative to glycoaldehyde based pathways described in WO 2017/059236, US 2016/0076061, US 2015/0147794, and WO 2016/079440.

Accordingly, in one embodiment, the recombinant microorganism comprising the rGS pathway may further comprise pathways and/or modifications described in these documents. For example, the recombinant microorganism comprising the rGS pathway may have reduced or eliminated activity of, or reduced or eliminated expression of xylulokinase, recombinantly express an enzyme that interconverts xylulose to ribulose, recombinantly expresses D-ribulose-phosphate aldolase (e.g., fucA gene from *E. coli*), recombinantly expresses a D-ribulokinase (e.g., gene fucK from *E. coli*), and/or recombinantly expresses a glycolaldehyde dehydrogenase, such as aldehyde dehydrogenase A (e.g., gene aldA from *E. coli*).

The recombinant microorganism comprising the rGS pathway may have reduced or eliminated activity of, or reduced or eliminated expression of xylulokinase, recombinantly express an enzyme to convert D-xylulose to D-xylulose-1P (e.g., khk-C from *Homo sapiens*), recombinantly expresses D-xylulose-1-phosphate aldolase (e.g., gene aldoB from *Homo sapiens*) and recombinantly expresses a glycoaldeyde dehydrogenase, such as aldehyde dehydrogenase A (e.g., gene aldA from *E. coli*). The recombinant microorganism comprising the rGS pathway may have reduced or eliminated activity of, or reduced or eliminated expression of an enzyme that interconverts xylose to D-xylulose (e.g., gene xylA from *E. coli*), recombinantly expresses an enzyme to convert xylose to D-xylonate, recombinantly expresses an enzyme to convert D-xylonate to 2-dehydro-3-deoxy-D-pentonate (DPP) (e.g., gene yagF from *E. coli*), recombinantly expresses a 2-keto-3-deoxy-D-pentonate aldolase (e.g., gene yagE from *E. coli*) and recombinantly expresses a glycoaldeyde dehydrogenase, such as aldehyde dehydrogenase A (e.g., gene aldA from *E. coli*).

In some embodiments, the recombinant microorganism comprising the rGS pathway may include a deletion of the gene encoding xylulokinase (e.g., gene xylB from *E. coli*). In some embodiments, the enzyme that interconverts xylulose and ribulose is D-tagatose 3-epimerase (e.g. gene dte from *Pseudomonas cichorii*). In certain embodiments, D-tagatose 3-epimerase is encoded by the dte gene from *P. cichorii* that is codon-optimized for *E. coli* or *S. cerevisiae*. In some embodiments, the recombinant microorganism comprising the rGS pathway may have reduced or eliminated activity of, or reduced or eliminated expression of glycolaldehyde reductase. For example, the recombinant microorganism may include a deletion of the gene encoding glycolaldehyde reductase (e.g. gene fucO).

In another embodiment, the rGS pathway of the present invention can be co-utilized with a serine/hydroxypyruvate pathway described in U.S. Pat. No. 8,911,978. Accordingly, in one embodiment, the recombinant microorganism comprising the rGS pathway may show an increased level of expression of pyruvate decarboxylase (e.g., pyruvate decarboxylase encoded by genes Pdc1, Pdc 5, Pdc6 from yeast), aldehyde dehydrogenase (e.g., aldehyde dehydrogenase encoded by genes aldA, aldB, aldH, and gabD), serine transaminase, and/or serine oxidase.

In another embodiment, the recombinant microorganism comprising the rGS pathway may further comprise genetic modifications described in U.S. Pat. Nos. 9,034,615, and 8,945,888; PCT Publication Nos. WO 2016/193540 and WO 2015/181074; and U.S. Pre-Grant Publication No. 2014/0295510.

Methods

The present invention provides methods for the production of glycolic acid and glycine using any one of the recombinant microorganisms described herein.

In one embodiment, the method comprises culturing in a suitable culture medium a recombinant microorganism that expresses a gene encoding malate dehydrogenase that catalyzes the conversion of pyruvate to malate, a gene encoding malate thiokinase that catalyzes the conversion of malate to malyl coenzyme A, and a gene encoding malyl coenzyme A lyase that catalyzes the conversion of malyl coenzyme A to glyoxylate and acetyl coenzyme A. The gene encoding malate dehydrogenase may encode for malate dehydrogenase that catalyzes the conversion of pyruvate to malate and/or OAA to malate but preferably does not catalyze (or catalyzes less efficiently) the reverse reaction from malate to pyruvate or malate to OAA.

In one embodiment, the method comprises culturing in a suitable culture medium a recombinant microorganism that expresses a gene encoding pyruvate carboxylase that catalyzes the conversion of pyruvate to OAA, and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA in combination with a gene encoding malate thiokinase that catalyzes the conversion of malate to malyl coenzyme A, and a gene encoding malyl coenzyme A lyase that catalyzes the conversion of malyl coenzyme A to glyoxylate and acetyl coenzyme A.

In one embodiment, the method comprises culturing in a suitable culture medium a recombinant microorganism that expresses a gene encoding pyruvate carboxylase that catalyzes the conversion of pyruvate to OAA, and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA in combination with a gene encoding malate thiokinase that catalyzes the conversion of malate to malyl coenzyme A, and a gene encoding malyl coenzyme A lyase that catalyzes the conversion of malyl coenzyme A to glyoxylate and acetyl coenzyme A, wherein the acetyl-CoA produced by the malyl coenzyme A lyase combines with the OAA to increase the biosynthesis of GA and/or glycine. In the same embodiment, the recombinant microorganism that may have, or may not have, a glucose-6-phosphate isomerase, pyruvate kinase, pyruvate dehydrogenase and/or malate dehydrogenase enzymes down-regulated or deleted.

In one embodiment, the method comprises culturing in a suitable culture medium a recombinant microorganism that expresses a gene encoding pyruvate carboxylase that catalyzes the conversion of pyruvate to OAA, and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA in combination with a gene encoding malate dehydrogenase that catalyzes the conversion of OAA to malate, a gene encoding malate thiokinase that catalyzes the conversion of malate to malyl coenzyme A, and a gene encoding malyl coenzyme A lyase that catalyzes the conversion of malyl coenzyme A to glyoxylate and acetyl coenzyme A. The gene encoding malate dehydrogenase may encode for malate dehydrogenase that catalyzes the conversion of pyruvate to malate and/or OAA to malate but preferably does not catalyze (or catalyzes less efficiently) the reverse reaction from malate to pyruvate or malate to OAA.

In another embodiment, the method comprises culturing in a suitable culture medium a recombinant microorganism that expresses a gene encoding pyruvate carboxylase that catalyzes the conversion of pyruvate to OAA, and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; a gene encoding malate dehydrogenase that catalyzes the conversion of pyruvate to malate; a gene encoding malate dehydrogenase that catalyzes the conversion of OAA to malate; a gene encoding malate thiokinase that catalyzes the conversion of malate to malyl coenzyme A; and a gene encoding malyl coenzyme A lyase that catalyzes the conversion of malyl coenzyme A to glyoxylate and acetyl coenzyme A. In one embodiment, the gene encoding malate dehydrogenase encodes for a modified malate dehydrogenase that catalyzes the conversion of pyruvate to malate or OAA to malate but does not catalyze the reverse reaction of malate to pyruvate or malate to OAA or shows reduced conversion of malate to pyruvate or malate to OAA.

In another embodiment, the method comprises culturing in a suitable culture medium a recombinant microorganism that expresses a gene encoding pyruvate carboxylase that catalyzes the conversion of pyruvate to OAA, and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; a gene encoding malate thiokinase that catalyzes the conversion of malate to malyl coenzyme A, and a gene encoding malyl coenzyme A lyase that catalyzes the conversion of malyl coenzyme A to glyoxylate and acetyl coenzyme A, wherein the microorganism does not comprise a gene encoding malate dehydrogenase that catalyzes the conversion of OAA to malate or comprises a deletion or loss-of-function mutation in the gene encoding malate dehydrogenase that catalyzes the conversion of OAA to malate.

In another embodiment, the method comprises culturing in a suitable culture medium a recombinant microorganism that expresses a gene encoding pyruvate carboxylase that catalyzes the conversion of pyruvate to OAA, and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; a gene encoding malate dehydrogenase that catalyzes the conversion of pyruvate to malate; a gene encoding malate thiokinase that catalyzes the conversion of malate to malyl coenzyme A, and a gene encoding malyl coenzyme A lyase that catalyzes the conversion of malyl coenzyme A to glyoxylate and acetyl coenzyme A, wherein the microorganism does not comprise a gene encoding malate dehydrogenase that catalyzes the conversion of OAA to malate or comprises a loss-of-function mutation in the gene encoding malate dehydrogenase that catalyzes the conversion of OAA to malate.

In one embodiment, glyoxylate is reduced to glycolate by the NAD(P)H-dependent glyoxylate reductase expressed by the recombinant microorganisms.

In one embodiment, glyoxylate is converted to glycine using alanine-glyoxylate aminotransferase; glycine dehydrogenase; glycine transaminase; serine-glyoxylate transaminase; and/or glycine oxidase expressed by the recombinant microorganisms.

A suitable culture medium used in the methods of the present disclosure comprises a fermentable carbon source. In one embodiment, the carbon source is selected from sugars, glycerol, alcohols, organic acids, alkanes, fatty acids, lignocellulose, proteins, carbon dioxide, and carbon monoxide. In an exemplary embodiment, the carbon source is sugar. In a further exemplary embodiment, the carbon source is a hexose and/or a pentose sugar. In another embodiment, the carbon source is glucose or oligomers of glucose, or comprises a biomass hydrolysate comprising hemicellulose. In another embodiment, the carbon source is a monosaccharide (such as glucose, xylose, arabinose, fructose, and mannose), a disaccharide (such as sucrose, lactose, and maltose), an oligosaccharide (such as galactose) or a polysaccharide (such as cellulose).

In another embodiment, the method for producing GA and/or glycine comprises culturing in a suitable culture medium a recombinant microorganism that expresses a set of genes encoding:
(a) malate dehydrogenase that catalyzes the carboxylation of pyruvate to malate;
(b) malate thiokinase that catalyzes the conversion of malate to malyl-CoA; and
(c) malyl CoA lyase that catalyzes the split of malyl-CoA into glyoxylate and acetyl-CoA;
(d) optionally phosphoenolpyruvate carboxylase, and/or phosphoenolpyruvate carboxykinase, and/or pyruvate carboxylase;
and comprises at least one modification selected from the group consisting of:
(a) deletion or attenuation of a gene encoding malate synthase;
(b) deletion or attenuation of a gene encoding isocitrate dehydrogenase;
(c) deletion or attenuation of a gene encoding pyruvate dehydrogenase, pyruvate oxidase and/or pyruvate formate-lyase;
(d) deletion or attenuation of a gene encoding malate dehydrogenase that converts oxaloacetate to malate or malate to oxaloacetate; and
(e) deletion or attenuation of a gene encoding pyruvate kinase.

In another embodiment, the method for producing GA and/or glycine comprises culturing in a suitable culture medium a recombinant microorganism that expresses a set of genes encoding:
(a) malate dehydrogenase that catalyzes the carboxylation of pyruvate to malate;
(b) malate thiokinase that catalyzes the conversion of malate to malyl-CoA; and (c) malyl CoA lyase that catalyzes the split of malyl-CoA into glyoxylate and acetyl-CoA;
and comprises:
(a) an attenuation of the gene encoding malate dehydrogenase that catalyzes the conversion of oxaloacetate to malate or the gene encoding malate dehydrogenase that catalyzes malate to oxaloacetate or an attenuation/mutation of the gene encoding malate dehydrogenase that catalyzes the carboxylation of pyruvate to malate so it shows reduced conversion of malate to pyruvate; and
(b) deletion or attenuation of a gene encoding malate synthase (e.g. genes aceB and/or glcB in *E. coli* or genes DAL7 and MLS1 in *S. cerevisiae*).

In another embodiment, the method for producing GA and/or glycine comprises culturing in a suitable culture medium a recombinant microorganism that expresses a set of genes encoding:
(a) phosphoenolpyruvate carboxylase that catalyzes the carboxylation of PEP to oxaloacetate and/or phosphoenolpyruvate carboxykinase that catalyzes the carboxylation of PEP to oxaloacetate and/or pyruvate carboxylase that catalyzes the carboxylation of pyruvate to oxaloacetate and/or malate dehydrogenase that catalyzes the carboxylation or pyruvate to malate;
(b) malate thiokinase that catalyzes the conversion of malate to malyl-CoA; and
(c) malyl-CoA lyase that catalyzes the conversion of malyl-CoA to glyoxylate and acetyl-CoA;
(d) and optionally malate dehydrogenase that catalyzes the conversion of oxaloacetate to malate, and;
wherein the microorganism comprises at least one modification selected from the group consisting of:
(a) deletion or attenuation of a gene encoding malate synthase;
(b) deletion or attenuation of a gene encoding isocitrate dehydrogenase;
(c) deletion or attenuation of a gene encoding pyruvate dehydrogenase, pyruvate oxidase and/or pyruvate formate-lyase;
(d) deletion or attenuation of the gene encoding malate dehydrogenase that catalyzes the conversion of malate to pyruvate or the gene encoding malate dehydrogenase that catalyzes the conversion of malate to oxaloacetate;
(e) deletion or attenuation of a gene encoding pyruvate kinase
(f) deletion or attenuation of a gene encoding glyoxylate carboligase;
(g) deletion or attenuation of a gene encoding 2-oxo-4-hydroxyglutarate aldolase;
(h) deletion or attenuation of a gene encoding glycoaldehyde reductase;
(i) deletion or attenuation of a gene encoding glycolate oxidase; and
(j) deletion or attenuation of a gene encoding a repressor of isocitrate lyase.

In yet another embodiment, the method for producing GA and/or glycine comprises culturing in a suitable culture medium a recombinant microorganism that shows an increased level of expression or increased activity (i.e., enhanced kinetic parameters for the desired reaction) or higher specificity (i.e., engineered enzyme that is >5×, >$10^1$×, >$10^2$×, >$10^3$×, $10^4$× or preferably >$10^5$ more specific to the target substrate compared to its wild-type enzyme; or novel homologous enzyme) of one or more enzymes selected from the group consisting of: pyruvate carboxylase, phosphoenolpyruvate carboxylase, phosphoenolpyruvate carboxykinase, malate dehydrogenase, malate thiokinase, malyl coenzyme A lyase, NADH-dependent glyoxylate reductase, and NADPH-dependent glyoxylate reductase.

In yet another embodiment, the method for producing GA and/or glycine comprises culturing in a suitable culture medium a recombinant microorganism that shows a decreased level of expression of at least one enzyme selected from the group consisting of: malate synthase, isocitrate dehydrogenase, pyruvate dehydrogenase, pyruvate oxidase and/or pyruvate formate-lyase, pyruvate kinase, glyoxylate carboligase, 2-oxo-4-hydroxyglutarate aldolase, glucose-6-phosphate isomerase, glycoaldehyde reductase, and glycolate oxidase.

In another embodiment, the method for producing GA and/or glycine may comprise a deletion or modification that decreases the activity of the pyruvate dehydrogenase, preventing or at least diminishing a major carbon loss from pyruvate conversion to acetyl-CoA, and favoring the carbon rerouting from pyruvate or phosphoenolpyruvate into oxaloacetate via carboxylation activity of enzyme candidates proposed herein.

In another embodiment, the method for producing GA and/or glycine may comprise a deletion or modification that decreases the activity of the pyruvate kinase, favoring the carbon fixation of phosphoenolpyruvate into oxaloacetate via carboxylation activity of enzyme candidates proposed herein.

The methods of the present disclosure may provide a yield of glycolic acid in the range of about 1.1 g of glycolic acid per g of carbon source to about 2.0 g/g, including values and ranges therebetween. For example, the yield of glycolic acid can be about 1.1., 1.2, 1.3, 1.4, 1.5, 1.6, 1.7, 1.8, 1.9 or about 2.0 g/g. The yield of glycolic acid may range from about 1.1 to about 1.8 g/g, about 1.2 to about 1.8 g/g, about 1.3 to about 1.8 g/g, about 1.4 to 1.8 g/g, about 1.4 to 1.7 g/g, or about 1.4 to 1.6 g/g.

The methods of the present disclosure may provide a yield of glycine in the range of about 1.0 g of glycine per g of carbon source to about 1.5 g/g, including values and ranges therebetween. For example, the yield of glycine can be about 1.0, 1.1., 1.2, 1.3, 1.4, or 1.5 g/g. The yield of glycine may range from about 1.0 to about 1.4 g/g, about 1.0 to about 1.3 g/g, about 1.0 to about 1.2 g/g, about 1.1 to 1.5 g/g, about 1.1 to 1.4 g/g, or about 1.1 to 1.3 g/g, or about 1.2 to 1.4 g/g.

Production of Poly-Glycolic Acid (PGA)

The present disclosure also encompasses methods of producing polyglycolic acid (PGA). The glycolic acid produced by the recombinant microorganisms of the present disclosure can be used for the production of PGA. PGA can be produced from GA via in vivo polymerization reactions or via chemical polymerization reactions.

In one embodiment, PGA is produced using an in vivo polymerization route described in U.S. Pre-Grant Publication No. 2011/0118434A1, incorporated by reference in its entirety. In this route, once GA is produced, two classes of enzymes—Coenzyme A transferase/synthase and PHA synthase, may be used to produce PGA inside the cell. Accordingly, in one embodiment, the recombinant microorganism of any one of the embodiments disclosed herein may comprise a gene encoding polyhydroxyalkanoate (PHA) synthase.

Four major classes of PHA synthases are known (Rhem, B., 2003). Class I and Class II PHA synthases comprise enzymes consisting of only one type of subunit (PhaC). According to their in vivo and in vitro specificity, class I PHA synthases (e.g. in *Ralstonia eutropha*) preferentially utilize CoA-thioester of various hydroxy fatty acids comprising 3 to 5 carbons atoms, whereas class II PHA synthases (e.g. in *Pseudomonas aeruginosa*) preferentially utilize CoA-thioester of various hydroxy fatty acids comprising 6 to 14 carbon atoms. Class III synthases (e.g. in *Allochromatium vinosum*) comprises enzymes consisting of two different types of subunits: the PhaC and the PhaE subunits. These PHA synthases prefer CoA-thioesters of hydroxy fatty acids comprising 3 to 5 carbons atoms. Class IV PHA synthases (e.g. in *Bacillus megaterium*) resemble the class III PHA synthases, but PhaE is replaced by PhaR.

In one embodiment, the gene encoding the PHA synthase is phaC, phaEC and/or phaCR.

In one embodiment, glycolic acid is converted into glycolyl-coA by one or more enzymes selected from the group consisting of: acyl-CoA synthetases, acyl-CoA transferases, and phosphotransbutyrylase associated to butyrate kinase.

In an exemplary embodiment, the enzyme transforming the glycolic acid into glycolyl-CoA is from an Enterobacteriaceae species. In an exemplary embodiment, the recombinant microorganism of any one of the embodiments described herein may comprise the gene prpE encoding propionyl coenzyme A synthetase from *Escherichia coli* or *Salmonella thyphimurium*, the gene acs from *E. coli* encoding acetyl-CoA transferase, the gene ptb encoding phosphotransbutyrylase and/or the gene buk encoding butyrate kinase.

If not through in vivo polymerization, there are chemical polymerization methods known in the Art: Ring opening polymerization from Kureha to have a high-molecular weight PGA (paper is attached) as well as direct polycondensation that reaches to a low-molecular weight PGA (Singh & Tiwari, 2010.).

Alternatively, the PGA can be prepared via chemical polymerization routes such as the ring-opening polymerization of cyclic diesters or the polycondensation of 2-hydroxycarboxylic acids. In an exemplary embodiment, the PGA can be produced using the ring opening polymerization method described by Yamane et al. (Polymer Journal, August 2014, pp. 1-7) to obtain a high-molecular weight PGA. In another exemplary embodiment, the PGA can be produced via direct polycondensation to obtain a low-molecular weight PGA (Singh & Tiwari, International Journal of Polymer Science, Volume 2010, Article ID 652719, 23 pages, doi:10.1155/2010/652719).

The present disclosure also provides methods for producing recombinant microorganisms capable of producing glycolic acid and/or glycine from glyoxylate using a reverse glyoxylate shunt. In one embodiment, the method for producing a recombinant microorganism comprises introducing into the microorganism one or more genes or introducing a gain-of-function mutation into one or more genes selected from the group consisting of:
(a) a gene encoding pyruvate carboxylase to convert pyruvate to OAA;
(b) a gene encoding phosphoenolpyruvate carboxylase to convert phosphoenolpyruvate to OAA;
(c) a gene encoding phosphoenolpyruvate carboxykinase to convert phosphoenolpyruvate to OAA;
(d) a gene encoding malate dehydrogenase to convert OAA to malate and/or pyruvate to malate;
(e) a gene encoding malate thiokinase to convert malate to malyl coenzyme A;
(f) a gene encoding malyl coenzyme A lyase to convert malyl coenzyme A to glyoxylate and acetyl-CoA;
(g) a gene encoding NADH-dependent glyoxylate reductase to convert glyoxylate to glycolate; and
(h) a gene encoding NADPH-dependent glyoxylate reductase to convert glyoxylate to glycolate.

The nucleotide sequences for the genes encoding the above polypeptides are known in the art and are publicly available (www.ncbi.nlm.nih.gov/genbank/). Methods for incorporating a desired nucleic acid sequence into the genome of the microorganism or into an expression vector are also known. For example, U.S. Pat. No. 9,034,615, which is incorporated by reference herein, discloses a method for incorporating the gene ycdW (encoding NADPH-dependent glyoxylate reductase) into an expression vector.

In certain embodiments, the recombinant microorganism comprises a deletion or modification that attenuates the expression of an endogenous gene. Exemplary methods for producing these microorganisms include deleting the gene or attenuating the expression of the gene by replacing the natural promoter by a low strength promoter or by introducing mutations into the gene that lead to decreased enzymatic activity.

In some embodiments, the method for producing a recombinant microorganism comprises introducing into the microorganism a deletion or modification that attenuates the expression of or inhibits the activity of the enzyme encoded by at least one endogenous gene selected from the group consisting of:
(a) a gene encoding malate synthase;
(b) a gene encoding isocitrate dehydrogenase;
(c) a gene encoding pyruvate dehydrogenase, pyruvate oxidase and/or pyruvate formate-lyase;
(d) a gene encoding pyruvate kinase;
(e) a gene encoding malate dehydrogenase;
(f) a gene encoding glyoxylate carboligase;
(g) a gene encoding 2-oxo-4-hydroxyglutarate aldolase;
(h) a gene encoding glycoaldehyde reductase;
(i) a gene encoding glycolate oxidase;
(j) a gene encoding a repressor of isocitrate lyase; and
(l) a gene encoding a glucose-6-phosphate isomerase.

The methods for producing a recombinant microorganism may further comprise (a) introducing into the microorganism a deletion or modification that attenuates the expression of a gene encoding malate: quinone oxidoreductase and/or (b) introducing a gain-of-function mutation into a gene encoding malate dehydrogenase, a gene encoding pyruvate carboxylase, a gene encoding phosphoenolpyruvate carboxylase, a gene encoding phosphoenolpyruvate carboxykinase, a gene encoding malate thiokinase, a gene encoding malyl-CoA lyase a gene encoding alanine-glyoxylate aminotransferase; a gene glycine dehydrogenase; a gene encoding glycine transaminase; a gene encoding serine-glyoxylate transaminase; a gene encoding glycine oxidase; a gene encoding alanine transaminase and/or a gene encoding NADPH-dependent glutamate synthase.

The foregoing detailed description has been given for clearness of understanding only and no unnecessary limitations should be understood therefrom as modifications will be obvious to those skilled in the art.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

EXAMPLES

Example 1

In Silico Analysis for the Biosynthesis and Improvement of Glycolic Acid Production Via Reverse Glyoxylate Shunt Activity in *E. coli*

Flux balance analyses (FBAs) were performed to simulate the impact of the genetic modifications as described herein, on the production yield of glycolate under various scenarios (FIG. 3 and FIG. 4). To do so, genome-scale metabolic model iJO1366, containing all known metabolic reactions of *Escherichia coli* (Orth J D. et al. (2011) A comprehensive genome-scale reconstruction of *Escherichia coli* metabolism—2011. Mol Syst Biol. 7:535), was modified to simulate glycolic acid (GA) production using a combination of glyoxylate (GS) and reverse glyoxylate (rGS) shunts. The model was modified to include additional reactions and the corresponding metabolites, including a malate thiokinase reaction (EC 6.2.1.9), a malyl-coA ligase reaction (EC 4.1.3.24), and a pyruvate carboxylase reaction (EC 6.4.1.1).

Simulations were carried out using the OptFlux software (Rocha L. (2010) OptFlux: an open-source software platform for in silico metabolic engineering. BMC Syst Biol. 4:45). In exemplary embodiments, parsimonious flux balance analyses were performed to evaluate the maximal theoretical production yields of GA through GS/rGS engineering. Depending on the exemplary embodiment, the transport system used was either hexokinase HXK (E.C. 2.7.1.1) or phosphotransferase system (PTS), while the carboxylation enzyme used to enter the TCA cycle was either phosphoenolpyruvate carboxykinase (PEPCK) (E.C. 4.1.1.32), phosphoenolpyruvate carboxylase (PPC) (E.C. 4.1.1.31), or pyruvate carboxylase PPC (EC 6.4.1.1).

Simulations were performed by applying a set of constraints readily reproduced under in vivo culture conditions of an *E. coli* strain, in which glucose is a carbon substrate and under aerobic conditions. The glucose substrate flux was arbitrarily set at 10 Cpmoles.gCDW-1.h-1. No constraints were set regarding a minimal biomass yield, or cell maintenance cost. Simulation results depicting the maximal theoretical production of GA are presented in Table 1.

strate, phosphoenolpyruvate. The performance of said strains can however be enhanced in a PTS deficient strain, where glucose is mostly transported via hexokinase HXK. As depicted on the flux maps (FIG. 3 and FIG. 4), maximal yields can only be achieved by diverting 86 to 100% of the carbon flux coming from glucose towards the pentose phosphate pathway, to provide the redox cofactors for the final glyoxylate reductase reaction (E.C. 1.1.1.26). This carbon flow towards the pentose phosphate pathway was considered as an alternative to provide the NADPH cofactor requirement for a NADPH-dependent glyoxylate reductase.

Example 2

In Vive Biosynthesis and Improvement of Glycolic Acid Production Via Reverse Glyoxylate Shunt Activity in *E. coli*, Combined with Carboxylation Through Pyruvate Carboxylase Activity As previously described (Alkim C. (2016) The synthetic xylulose-1 phosphate pathway increases production of glycolic acid from xylose-rich sugar mixtures. Biotechnol Biofuels, 9:201), production of glycolic acid (GA) in *E. coli* can be enhanced by inactivating all annotated reactions that consume glyoxylic acid, i.e., malate synthase, encoded by aceB (GenBank Gene ID: 948512) and glcB (GenBank Gene ID: 948857), glyoxylate carboligase, encoded by gcl (GenBank Gene ID: 945394), and 2-oxo-4-hydroxyglutarate aldolase, encoded by eda (GenBank Gene ID: 946367). Reoxidation of GA can further be prevented by deleting the glycolate oxidase-encoding glcDEFG operon (GenBank Gene ID: 947353, 2847718, 2847717, 947473).

The experiments described below were thus carried out in an *Escherichia coli* K12 strain MG1655 ΔaceB ΔglcDEFGB Δgcl Δedd-eda. The strain, referred to as SGK_rGS_00, was a gift from Alkim et al. (Alkim C. (2016) The synthetic xylulose-1 phosphate pathway increases production of glycolic acid from xylose-rich sugar mixtures. Biotechnol Biofuels, 9:201).

Deletion of the Pgi Locus, Encoding for Phosphoglucose Isomerase

To construct a strain with an enhanced pentose phosphate activity and NADPH pool, deletion of pgi (GenBank Gene

TABLE 1

Simulation results depicting the maximal theoretical production of GA.

| Glucose Transport | Carboxylation Reaction | qSubstrates (μmole · gCDW−1 · h−1) | | | qProducts (μmole · gCDW−1 · h−1) | | | Theoretical production yield (gGA/ gGlucose) |
|---|---|---|---|---|---|---|---|---|
| | | Glucose | O2 | CO2 | Glycolate | Pyruvate | Acetate | |
| HXK | PEPCK | 10 | 8.57 | 8.57 | 34.29 | 0 | 0 | 1.43 |
| | PPC | 10 | 10.3 | 6.06 | 32.12 | 0.61 | 0 | 1.34 |
| | PYC | 10 | 10.3 | 6.06 | 32.12 | 0.61 | 0 | 1.34 |
| PTS | PEPCK | 10 | 5 | 10 | 20 | 10 | 0 | 0.83 |
| | PPC | 10 | 5 | 10 | 20 | 10 | 0 | 0.83 |
| | PYC | 10 | 10.09 | 6.44 | 33.04 | 0.004 | 0.17 | 1.38 |

Simulated flux maps are depicted in FIG. 3 and FIG. 4. Simulations show that a theoretical production yield of GA from glucose, via GS/rGS, can reach between 0.83 and 1.43 $g_{GA}/g_{Glucose}$, depending on the glucose transport system and the carboxylation enzyme used. Strains relying on PEPCK or PPC as a carboxylation enzyme are less performant in a PTS+ strain. This is likely due to the competition between the PTS system and PEPCK/PPC for their common sub- ID: 948535), encoding for glucose-6-phosphate isomerase, was performed by CRISPR-Cas9 according to standard procedure (Jiang Y. et al. (2015) Multigene editing in the *Escherichia coli* genome via the CRISPR-Cas9 system. Appl Environ Microbiol, 81:2506-2514). Plasmids pTargetF (pMB1 aadA sgRNA-cadA) harboring a guide RNA, and pCas (repA101-Ts kan Pcas-cas9 ParaB-Red lacIq Ptrc-sgRNA-pMB1) harboring a cas9 gene and a l-Red recombinase, were obtained from AddGene (respectively, Addgene plasmid #62226 and #62225; Addgene, Cambridge, USA).

A pTargetF pMB1 aadA sgRNA-pgi, expressing a guide RNA with a N20 sequence targeting the pgi locus, was obtained by overlap PCR, using primers Pgi_N20_FW, and Pgi_N20_RV described in Table 2. The donor DNA/disruption cassette was supplied as a PCR fragment, obtained by amplifying and combining 500 bp upstream and downstream the pgi locus by overlap PCR, using primers Pgi_H1_FW, Pgi_H1_RV, Pgi_H2_FW and Pgi_H2_RV (see Table 2).

TABLE 2

Oligonucleotides used for pgi disruption using CRISPR-Cas9. Binding regions are underlined. N20 sequence specific for pgi is indicated in italics.

| Primer Name | Sequence |
|---|---|
| Pgi_N20_FW | GTCCTAGGTATAATACTAGT*CCGATTATCTGGGGTGAACC*GTTTTAGAGCTAGAAATAGC (SEQ ID NO: 1) |
| Pgi_N20_RV | ACTAGTATTATACCTAGGACTGAG (SEQ ID NO: 2) |
| Pgi_H1_FW | ATGAAAAACATCAATCCAACGC (SEQ ID NO: 3) |
| Pgi_H1_RV | GGTGGATCAGTCGGTCACCATGTATGGGC (SEQ ID NO: 4) |
| Pgi_H2_FW | TGGTGACCGACTGATCCACCAGGGAACCA (SEQ ID NO: 5) |
| Pgi_H2_RV | CATATCGACGATGATTAACCGC (SEQ ID NO: 6) |

Genome editing was performed by adapting the protocol from (Jiang Y. et al. (2015) Multigene editing in the *Escherichia coli* genome via the CRISPR-Cas9 system. Appl Environ Microbiol, 81:2506-2514). Strain SGK_rGS_00 was first transformed by electroporation with the pCAS plasmid using standard procedure (Woodall C A. (2003) Plasmid Vectors. Methods in Molecular Biology. 235). Competent cells of the strain SGK_rGS_00 harboring pCAS were prepared while inducing λ-Red recombinase with arabinose (10 mM final concentration), as described previously (Jiang Y. et al. (2015) Multigene editing in the *Escherichia coli* genome via the CRISPR-Cas9 system. Appl Environ Microbiol, 81:2506-2514). 50 µl of competent cells was thereafter mixed with 100 ng of pTargetF plasmid, and 400 ng of donor DNA. Electroporation was performed in a 2-mm electroporation cuvette (VWR) at 2.5 kV, and the product was suspended immediately in 1 ml of LB medium (pre-warmed at 30° C.). Cells were allowed to recover at 30° C. overnight, before being plated onto LB agar containing kanamycin (50 µg/ml) and spectinomycin (50 µg/ml), and were incubated overnight at 30° C. Transformants were identified by colony PCR and sequencing. The resulting strain was called SGK_rGS_01: MG1655 ΔaceB ΔglcDEFGB Δgcl Δedd-eda Δpgi.

Deletion of the aceE Locus, Encoding for Subunit E1 of the Pyruvate Dehydrogenase To construct a strain that accumulates pyruvate to enhance the use of a carboxylation enzyme such as pyruvate carboxylase to enter the Krebs cycle, deletion of pyruvate dehydrogenase subunit E1 aceE was performed in strain SGK_rGS_01 according to standard procedure (Thomasson L C. (2007) *E. coli* Genome Manipulation by P1 Transduction. Curr Protoc Mol Biol. 79:1.17), using a MG1655 Δpgi::KanR strain JW0110, obtained from the Keio single-gene deletion collection (Baba T. et al. (2006) Construction of *Escherichia coli* K-12 in-frame, single-gene knockout mutants: the Keio collection. Mol Syst Biol. 2:2006.0008). Transformants were selected on LB agar supplemented with 100 µg/ml kanamycin and identified by colony PCR and sequencing. Removal of the antibiotic marker was further performed by specific recombination of FTR regions, using Flp recombination, as previously described in the literature (Datsenko K A. et al. (2000) One-step inactivation of chromosomal genes in *Escherichia coli* K-12 using PCR products. Proc Natl Acad Sci USA. 97(12):6640-5). The resulting strain was called SGK_rGS_02: MG1655 ΔaceB ΔglcDEFGB Δgcl Δedd-eda Δpgi ΔaceE.

Expression of Pyruvate Carboxylase, Citrate Synthase, Isocitrate Lyase and Glyoxylate Reductase to Enhance Carbon Fixation, Glyoxylate Shunt Activity and Glycolic Acid Synthesis Pyruvate carboxylase from *Rhizobium etli* strain CFN42 (SEQ ID NO: 20) (Uniprot accession number: Q2K340) was synthesized by Genewiz® (Leipzig, Germany). Native isocitrate lyase aceA (SEQ ID NO: 21) (GeneBank Gene ID: 948517) and glyoxylate reductase ghrA (SEQ ID NO: 23) (GeneBank Gene ID: 946431) genes were amplified by PCR from the genome of *E. coli* MG1655 using primers in Table 3. A NADH-insensitive citrate synthase mutant gltA$_{R163L}$ (SEQ ID NO: 22) was recovered by PCR from plasmid pACT3w-ppc$_{K620S}$-gltA$_{R163L}$, as described in Trichez et al. (Trichez D. (2018) Engineering of *Escherichia coli* for Krebs cycle-dependent production of malic acid. Microb Cell Fact. 17:113).

To express these genes as a synthetic operon, a pZS13-Luc plasmid (Expressys) was first modified by replacing the P$_{AllacO-1}$ promoter by a J23119 constitutive promoter (SEQ ID NO: 19) (http://parts.igem.org/Promoters/Catalog/Anderson) and introducing a multiple cloning site. The J23119 promoter was obtained as a synthetic gene fragment, synthesized by GeneWiz® (Leipzig, Germany). It was subsequently cloned into a pZS13-Luc plasmid by restriction cloning, between restriction sites AatII and KpnI. A multiple cloning site was recovered by digestion with KpnI and AvrII from a pZA21-MCS plasmid (Expressys), and incorporated into the plasmid by restriction cloning between said restriction sites KpnI and AvrII. The resulting plasmid is referred to as pZS1-J23119-MCS.

All genes were amplified by PCR using the primers described in Table 3. PCR fragments were purified on gel using EZ-10 Spin Column DNA Gel Extraction Kit (BioBasic) according to the manufacturer's protocol. Purified fragments were subsequently cloned into pZS1-J23119-MCS plasmid linearized by restriction with KpnI and HindIII, by using the NEBuilder® HiFi DNA Assembly Cloning Kit (New England Biolabs) according to the manufacturer's protocol. Construction was confirmed by PCR and sequencing. The resulting synthetic operon is referred to as J23119-pyc-aceA-gltA$_{R163L}$-ghrA (SEQ ID NO: 24), and the plasmid as pZS1-pyc. (see Table 4).

by restriction cloning between restriction sites AatII and KpnI. The resulting plasmid is referred to as pZA3-P$_{Tac}$-MCS.

All genes were amplified by PCR using the primers described in Table 4. PCR fragments were purified on gel using EZ-10 Spin Column DNA Gel Extraction Kit (BioBasic) according to the manufacturer's protocol. Purified fragments were subsequently cloned as a synthetic operon into

TABLE 3

Oligonucleotides used for the construction of the synthetic operon J23119-pyc-aceA-gltAR164L-ghrA. Binding regions are underlined. Overhangs are used for assembly cloning using NEBuilder ® HiFi DNA Assembly Cloning Kit (New England Biolabs).

| Primer Name | Sequence |
|---|---|
| pyc_FW | TTGTTTAACTTTAAGGAGGTTTGGAGGTACCATGCCCATATCCAAG (SEQ ID NO: 7) |
| pyc_RV | TTTTCATACGGTTCCTCCTTCTAGATCATCCGCCGTAAACCG (SEQ ID NO: 8) |
| aceA_FW | CGGATGATCTAGAAGGAGGAACCGTATGAAAACCCGTACACAACAAAT (SEQ ID NO: 9) |
| aceA_RV | TTGTATCAGCCATCGTGTGCCTCCTTTAGAACTGCGATTCTTCAGTG (SEQ ID NO: 10) |
| gltA_FW | ATCGCAGTTCTAAAGGAGGCACACGATGGCTGATACAAAAGCAAAACTC (SEQ ID NO: 11) |
| gltA_RV | AGATGATATCCATCGTGTGCCTCCTTTAACGCTTGATATCGCTTTTAAAGTC (SEQ ID NO: 12) |
| ghrA_FW | TATCAAGCGTTAAAGGAGGCACACGATGGATATCATCTTTTATCACCCAAC (SEQ ID NO: 13) |
| ghrA_RV | GGCTGCAGGAATTCGATATCATAGATTAGTAGCCGCGTGCGCG (SEQ ID NO: 14) |

TABLE 4

Oligonucleotides used for the construction of the synthetic operon PTac-sucCD-mcl. Binding regions are underlined. Overhangs are used for assembly cloning using NEBuilder ® HiFi DNA Assembly Cloning Kit (New England Biolabs).

| Primer Name | Sequence |
|---|---|
| sucCD_FW | ACAATTTCACACAGGAAACAGAATTCCTATAATTTTGTTTAACTTTAAG (SEQ ID NO: 15) |
| sucCD_RV | TATAGTCTAGATCAGAATCTGATTCCGTG (SEQ ID NO: 16) |
| mcl_FW | GAATCAGATTCTGATCTAGACTATAATTTTGTTTAACTTTAAGGAGGTT (SEQ ID NO: 17) |
| mcl_RV | TAGCACGCGTTTACTTTCCGCCCATCGCG (SEQ ID NO: 18) |

Expression of Malate Thiokinase and Malyl-coA Ligase to Introduce Reverse Glyoxylate Shunt Activity The sucC2-sucD2 operon from *Methylococcus capsulatus* str. Bath (SEQ ID NO: 26) (Uniprot Q607L9 and Q607L8), encoding a malate thiokinase, and mcl gene from *Methylobacterium extorquens* AM1 (SEQ ID NO: 27) (Uniprot C5B113), encoding a malyl-coA lyase, were ordered as synthetic genes from GeneWiz® (Leipzig, Germany). To express these genes as a synthetic operon, a pZA31-MCS plasmid (Expressys) was first modified by replacing the P$_{LtetO-1}$ promoter by a P$_{Tac}$ inducible promoter (SEQ ID NO: 25), recovered from a standard pACT3 plasmid, and cloned pZA3-P$_{Tac}$-MCS plasmid linearized by restriction with EcoRI and MluI, by using the NEBuilder® HiFi DNA Assembly Cloning Kit (New England Biolabs) according to the manufacturer's protocol. Construction was confirmed by PCR and sequencing. The resulting synthetic operon is referred to as P$_{Tac}$-sucCD-mcl (SEQ ID NO: 28), and the plasmid as pZA3-rGS (see Table 5).

Assay for Glycolic Acid Production

Three *E. coli* strains were tested for the GA production assay. Wild-type strain MG1655, and engineered strains SGK_rGS_01 and SGK_rGS_02 were tested (i) without plasmids, as negative controls (ii) with plasmid pZS1-pyc only, (ii) with plasmid pZA3-rGS, (iv) with both plasmids.

All strains were transformed by electroporation with the corresponding plasmids using standard procedure (Woodall C A. (2003) Plasmid Vectors. Methods in Molecular Biology. 235). Genotypes of plasmids and strains are presented in Table 5.

is a first indication that the combination of GS/rGS pathway has a positive impact on the production of GA, even in the wild-type strain.

Regarding engineered strain SGK_rGS_01, no significant GA production could be detected in the empty control strain,

TABLE 5

Genotypes of plasmids and strains for the glycolic acid production assay.

| Category | Name | Genotype |
| --- | --- | --- |
| Plasmids | pZS1-pyc | pZS1-J23119-pyc-aceA-gltA$_{R163L}$-ghrA (SEQ ID NO: 24) |
|  | pZA3-rGS | pZA3-P$_{Tac}$-sucCD-mcl |
| Strains | MG1655 | K12, F⁻, lambda⁻, rph-1 |
|  | MG1655_pyc | K12, F⁻, lambda⁻, rph-1 + pZS1-pyc |
|  | MG1655_rGS | K12, F⁻, lambda⁻, rph-1 + pZA3-rGS |
|  | MG1655_pyc_rGS | K12, F⁻, lambda⁻, rph-1 + pZS1-pyc + pZA3-rGS |
|  | SGK_rGS_01 | MG1655 ΔaceB ΔglcDEFGB Δgcl Δedd-eda Δpgi |
|  | SGK_rGS_01_pyc | MG1655 ΔaceB ΔglcDEFGB Δgcl Δedd-eda Δpgi + pZS1-pyc |
|  | SGK_rGS_01_rGS | MG1655 ΔaceB ΔglcDEFGB Δgcl Δedd-eda Δpgi + pZA3-rGS |
|  | SGK_rGS_01_pyc_rGS | MG1655 ΔaceB ΔglcDEFGB Δgcl Δedd-eda Δpgi + pZS1-pyc + pZA3-rGS |
|  | SGK_rGS_02 | MG1655 ΔaceB ΔglcDEFGB Δgcl Δedd-eda Δpgi ΔaceE |
|  | SGK_rGS_02_pyc | MG1655 ΔaceB ΔglcDEFGB Δgcl Δedd-eda Δpgi ΔaceE + pZS1-pyc |
|  | SGK_rGS_02_rGS | MG1655 ΔaceB ΔglcDEFGB Δgcl Δedd-eda Δpgi ΔaceE + pZA3-rGS |
|  | SGK_rGS_02_pyc_rGS | MG1655 ΔaceB ΔglcDEFGB Δgcl Δedd-eda Δpgi ΔaceE + pZS1-pyc + pZA3-rGS |

Strains were grown in M9 glucose medium (20 g/L glucose) supplemented with 15 mM acetate and 1 g/L Casamino acid for about 50 hours. Ampicillin and chloramphenicol were added with a final concentration of 100 µg/mL and 25 µg/mL, respectively (i.e. ampicillin for strain harboring pZS1-pyc, and chloramphenicol for strains harboring pZA3-rGS). Cultures were induced with IPTG (0.5 mM final) when their OD600 reaches around 0.6-0.8. Growth was monitored by $OD_{600}$. Samples were taken during growth until stationary phase. Glucose consumption and metabolite production was then analyzed by HPLC-UV/RI (Dionex Ultimate 3000, Thermo Fisher Scientific), with a Rezex ROA-Organic Acid column (Phenomenex), at 80° C. with $H_2SO_4$ 0.5 mM as mobile phase (0.5 mL/min). GA titer and GA yield after 24H are presented in Table 6.

As shown in Table 6, no significant production of glycolic acid was detected in the MG1655 wild-type control strain, without plasmid or with plasmid pZS1-pyc or pZA3-RGS only. This was expected, as all major competitive pathway (i.e. glyoxylate and glycolate degradation pathways) are still active in the wild-type strain. Interestingly, a limited amount of GA could however be detected when expressing both the pZS1-pyc plasmid, and the pZA3-rGS in the MG1655 wild-type strain. Titer reached up to 0.11 g/L of GA, which or in the strain with pZA3-rGS only. GA production could however be detected up to a titer of ca. 0.18 g/L when enhancing the glyoxylate shunt activity and glyoxylate reductase activity, using plasmid pZS1-pyc. The addition of the pZA3-rGS plasmid in the strain improved the GA titer by 910%, reaching up to 1.91 g/L. The production yield reached up to 0.24 $g_{GA}/g_{glucose}$ after 22.5 hours, showing a 2400% improvement when compared to the production yield without the rGS engineering Regarding engineered strain SGK_rGS_02, no significant GA production could be detected in the control strain with single plasmid. GA production was only detected when combining both plasmids, up to a titer of ca. 0.28 g/L.

TABLE 6

GA titer and yield evaluated during glycolic acid production assay after 24 h of growth

|  | MG1655 | | | | SGK_rGS_01 | | | | SGK_rGS_02 | | | |
| --- | --- | --- | --- | --- | --- | --- | --- | --- | --- | --- | --- | --- |
|  | Empty (control) | With pZS1-pyc | With pZA3-rGS | With pZS1-pyc + pZA3-rGS | Empty (control) | With pZS1-pyc | With pZA3-rGS | With pZS1-pyc + pZA3-rGS | Empty (control) | With pZS1-pyc | With pZA3-rGS | With pZS1-pyc + pZA3-rGS |
| GA titer (g/L) | 0 | 0 | 0 | 0.11 | 0 | 0.18 | 0 | 1.91 | 0 | 0 | 0 | 0.28 |
| GA yield (gGA/gGlucose) | 0 | 0 | 0 | 0.01 | 0 | 0.01 | 0 | 0.24 | 0 | 0 | 0 | 0.025 |

Example 3

Biosynthesis and Improvement of Glycolic Acid Production Via Reverse Glyoxylate Shunt Activity in *E. coli* Combined with Carboxylation Through Pep Carboxylase Activity The experiments described below were carried out in an *Escherichia coli* K12 strain MG1655 ΔaceB ΔglcDEFGB ΔgcI/Δedd-eda. The strain, referred to as SGK_rGS_00, was a gift from Alkim et al. (Alkim C. et al. (2016) The Synthetic Xylulose-1 phosphate pathway increases production of glycolic acid from xylose-rich sugar mixtures. Biotechnol Biofuels, 9:201).

Deletion of the Pgi Locus, Encoding for Phosphoglucose Isomerase

To construct a strain with an enhanced pentose phosphate activity and NADPH pool, deletion of pgi (GenBank Gene ID: 948535), encoding for glucose-6-phosphate isomerase, was performed by CRISPR-Cas9 according to standard procedure (Jiang Y. et al. (2015) Multigene editing in the Escherichia coli genome via the CRISPR-Cas9 system. Appl Environ Microbiol, 81:2506-2514). Disruption of the strain was performed as previously described in Example 2, and is referred to as SGK_rGS_01 (Table 5).

Deletion of the pykF Locus, Encoding for Pyruvate Kinase I

To construct a strain that accumulates phosphoenol pyruvate to enhance the use of a carboxylation enzyme such as pep carboxylase to enter the Krebs cycle, deletion of pyruvate kinase I pykF (GenBank Gene ID: 946179) was performed in strain SGK_rGS_01 by transduction according to standard procedure (Thomasson L C. (2007) E. coli Genome Manipulation by P1 Transduction. Curr Protoc Mol Biol. 79:1.17), using a MG1655 Δpgi::KanR strain JW1666, obtained from the Keio single-gene deletion collection (Baba T. et al. (2006) Construction of Escherichia coli K-12 in-frame, single-gene knockout mutants: the Keio collection. Mol Syst Biol. 2:2006.0008). Transformants were selected on LB agar supplemented with 100 μg/ml kanamycin and identified by colony PCR and sequencing. Removal of the antibiotic marker was further performed by specific recombination of FTR regions, using Flp recombination, as previously described in the literature (Datsenko K A. et al. (2000) One-step inactivation of chromosomal genes in Escherichia coli K-12 using PCR products. Proc Natl Acad Sci USA. 97(12):6640-5). The resulting strain was called SGK_rGS_03 MG1655 ΔaceB ΔglcDEFGB ΔgcI Δedd-eda Δpgi ΔpykF.

Expression of pep carboxylase, citrate synthase, isocitrate lyase and glyoxylate reductase to enhance carbon fixation, glyoxylate shunt activity and glycolic acid synthesis Plasmid pACT3w-ppc$_{K620S}$-gltA$_{R163L}$ was obtained from Trichez et al. (Trichez D. (2018) Engineering of Escherichia coli for Krebs cycle-dependent production of malic acid. Microb Cell Fact. 17:113). It contains a malate-insensitive pep carboxylase mutant ppc$_{K620S}$ and a NADH-insensitive citrate synthase mutant gltA$_{R163L}$, under the control of an inducible P$_{Tac}$ promoter. It was further modified as described below and used as a backbone to construct a synthetic operon. Genes encoding for the native isocitrate lyase aceA (GeneBank Gene ID: 948517) and the glyoxylate reductase ghrA (GeneBank Gene ID: 946431) were amplified by PCR from the genome of E. coli MG1655, respectively using the primers aceA_FW/aceA_RV and ghrA_FW/ghrA_RV described in Table 7. Geneppc$_{K620S}$ (SEQ ID NO: 29) was amplified by PCR along with plasmid backbone pACT3, using plasmid pACT3w-ppc$_{K620S}$-gtA$_{R163L}$ as a template, and primers pACT3_FW/ppc_RV, described in Table 7. Finally, gene gltA$_{R163L}$ was amplified by PCR, using plasmid pACT3w-ppc$_{K620S}$-gltA$_{R1163L}$ as template, and primers gltA_FW/gltA_RV described in Table 7.

TABLE 7

Oligonucleotides used for the construction of the synthetic operon J23119-pyc-aceA-gltAR164L-ghrA. Binding regions are underlined. Overhangs are used for assembly cloning using NEBuilder ® HiFi DNA Assembly Cloning Kit (New England Biolabs).

| Primer name | Sequence |
| --- | --- |
| pACT3_FW | TCTAGAAAGCTTCTGTTTTGGC (SEQ ID NO: 31) |
| ppc_RV | GTTCCTCCTTCTAGATTAGCCG (SEQ ID NO: 32) |
| aceA_FW | CGGCTAATCTAGAAGGAGGAACCGTATGAAAACCCGTACACAACAAAT (SEQ ID NO: 33) |
| aceA_RV | TTGTATCAGCCATCGTGTGCCTCCTTTAGAACTGCGATTCTTCAGTG (SEQ ID NO: 34) |
| gltA_FW | ATCGCAGTTCTAAAGGAGGCACACGATGGCTGATACAAAAGCAAAACTC (SEQ ID NO: 35) |
| gltA_RV | AGATGATATCCATCGTGTGCCTCCTTTAACGCTTGATATCGCTTTTAAAGTC (SEQ ID NO: 36) |

TABLE 7-continued

Oligonucleotides used for the construction of the synthetic operon
J23119-pyc-aceA-gltAR164L-ghrA. Binding regions are underlined.
Overhangs are used for assembly cloning using NEBuilder ® HiFi
DNA Assembly Cloning Kit (New England Biolabs).

| Primer name | Sequence |
|---|---|
| ghrA_FW | TATCAAGCGTTAAAGGAGGCACACG<u>ATGGATATCATCTTTTATCACCCAAC</u> (SEQ ID NO: 37) |
| ghrA_RV | TCCGCCAAAACAGAAGCTTTCTAGA<u>TTAGTAGCCGCGTGCGCG</u> (SEQ ID NO: 38) |

PCR fragments were purified on gel using EZ-10 Spin Column DNA Gel Extraction Kit (BioBasic) according to the manufacturer's protocol. Purified fragments were subsequently assembled, by using the NEBuilder® HiFi DNA Assembly Cloning Kit (New England Biolabs) according to the manufacturer's protocol. Construction was confirmed by PCR and sequencing. The resulting synthetic operon is referred to as $P_{tac}$-ppc$_{K620S}$-aceA-gtA$_{R163L}$-ghrA (SEQ ID NO: 30), and the plasmid as pACT3-ppc.

Expression of Malate Thiokinase and Malyl-coA Ligase to Introduce Reverse Glyoxylate Shunt Activity As described in Example 2, the sucC2-sucD2 operon from *Methylococcus capsulatus* str. Bath (SEQ ID NO: 26) (Uniprot Q607L9 and Q607L8), encoding a malate thiokinase, and mcl gene from *Methylobacterium extorquens* AM1 (Uniprot C5B113), encoding a malyl-coA lyase, were ordered as synthetic genes from GeneWiz® (Leipzig, Germany). Plasmid pZA3-rGS, containing the synthetic operon $P_{Tac}$-sucCD-mcl (SEQ ID NO: 28), was obtained as described in Example 2. In order to express the $P_{Tac}$-sucCD-mcl in a background compatible with plasmid pACT3-ppc, it was further transferred into a pZE23-MCS plasmid (Expressys), by restriction cloning between restriction sites AvrII and BglII. The resulting plasmid is referred to as pZE2-rGS.

Assay for Glycolic Acid Production

Two strains were tested for the GA production assay. Wild-type MG1655 and engineered strain SGK_rGS_03 were tested (i) with plasmid pACT3-ppc only, (ii) with plasmid pZE2-rGS only, and (iii) with both plasmids. All strains were transformed by electroporation with the corresponding plasmids using standard procedure (Woodall C A. (2003) Plasmid Vectors. Methods in Molecular Biology, 235). Genotypes of plasmids and strains are presented in Table 8.

TABLE 8

Genotypes of plasmids and strains used for glycolic acid production assay.

| Category | Name | Genotype |
|---|---|---|
| Plasmids | pACT3-ppc | pZS1-J23119-pyc-aceA-gltA$_{R163L}$-ghrA |
|  | pZE3-rGS | pZE2-P$_{Tac}$-sucCD-mcl |
| Strains | MG1655_ppc | K12, F−, lambda−, rph-1 + pACT3-ppc |
|  | MG1655_rGS | K12, F−, lambda−, rph-1+ pZE2-rGS |
|  | MG1655_ppc_rGS | K12, F−, lambda−, rph-1+ pZE2-rGS |
| Strains | SGK_rGS_03_ppc | MG1655 ΔaceB ΔglcDEFGB Δgcl Δedd-eda Δpgi ΔpykF + pACT3-PPC |
|  | SGK_rGS_03_rGS | MG1655 ΔaceB ΔglcDEFGB Δgcl Δedd-eda Δpgi ΔpykF + pZE2-rGS |
|  | SGK_rGS_03_ppc_rGS | MG1655 ΔaceB ΔglcDEFGB Δgcl Δedd-eda Δpgi ΔpykF + pZE2-rGS |

Strains were grown in M9 glucose medium (20 g/L glucose) supplemented with 15 mM acetate and 1 g/L Casamino acid for about 50 hours. Chloramphenicol and kanamycin were added with a final concentration of 25 μg/mL and 50 μg/mL, respectively (i.e. chloramphenicol for strain harboring pACT3-ppc, and kanamycin for strains harboring pZE2-rGS). Cultures were induced with IPTG (0.5 mM final) when their OD600 reaches around 0.6-0.8. Growth was monitored by OD$_{600}$. Samples were taken during growth until stationary phase. Glucose consumption and metabolite production was then analyzed by HPLC-UV/RI (Dionex Ultimate 3000, Thermo Fisher Scientific), with a Rezex ROA-Organic Acid column (Phenomenex), at 80° C. with $H_2SO_4$ 0.5 mM as mobile phase (0.5 mL/min). Glucose titer, GA titer and GA yield are presented in Table 9.

As shown in Table 9, a production of GA could be detected in the wild-type control, when expressing the pACT3-ppc with and without pZE2-rGS, but only with a maximal yield of 0.02 $g_{GA}/g_{glucose}$; whereas no production of glycolic acid was measured in the SGK_rGS_03 strain with plasmid pZE2-rGS only. GA production could, however, be detected in this strain up to a titer of about 0.8 g/L when enhancing the carbon fixation, glyoxylate shunt activity and glyoxylate reductase activity, using plasmid pACT3-ppc. The addition of the pZE2-rGS plasmid in SGK_rGS_03 does not improve the GA titer. The production yield reached up to 0.21 $g_{GA}/g_{glucose}$ after 46 hours, showing a 525% improvement with the strain expressing pACT3-ppc, and a 1050% improvement with the wild-type strain expressing both plasmids.

TABLE 9

GA titer and yield evaluated during glycolic acid production assay after 46 h.

| | MG1655 | | | | SGK_rGS_03 | | | |
|---|---|---|---|---|---|---|---|---|
| | Empty (control) | With pACT3-ppc | With pZE2-rGS | With pACT3-ppc + pZE2-rGS | Empty (control) | With pACT3-ppc | With pZE2-rGS | With pACT3-ppc + pZE2-rGS |
| GA titer (g/L) | 0 | 0.35 | 0 | 0.2 | ND | 0.8 | 0 | 0.71 |
| GA yield (gGA/gGlucose) | 0 | 0.02 | 0 | 0.02 | ND | 0.04 | 0 | 0.21 |

Enumerated Embodiments

1. A glyoxylate producing recombinant microorganism for the synthesis of glycolic acid (GA) and/or glycine, comprising:
(a) a gene encoding malate dehydrogenase that catalyzes the conversion of pyruvate to malate;
(b) a gene encoding malate thiokinase that catalyzes the conversion of malate to malyl coenzyme A; and
(c) a gene encoding malyl coenzyme A lyase that catalyzes the conversion of malyl coenzyme A to glyoxylate and acetyl-CoA.
2. A glyoxylate producing recombinant microorganism for the synthesis of glycolic acid (GA) and/or glycine, comprising:
(a) a gene encoding pyruvate carboxylase that catalyzes the conversion of pyruvate to oxaloacetate (OAA), and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA;
(b) a gene encoding malate dehydrogenase that catalyzes the conversion of OAA to malate;
(c) a gene encoding malate thiokinase that catalyzes the conversion of malate to malyl coenzyme A; and
(d) a gene encoding malyl coenzyme A lyase that catalyzes the conversion of malyl coenzyme A to glyoxylate and acetyl-CoA, wherein the acetyl-CoA produced by the malyl coenzyme A lyase combines with the OAA to increase the biosynthesis of GA and/or glycine.
3. A glyoxylate producing recombinant microorganism for the synthesis of glycolic acid (GA) and/or glycine, comprising:
(a) a gene encoding pyruvate carboxylase that catalyzes the conversion of pyruvate to oxaloacetate (OAA), and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA;
(b) a gene encoding malate thiokinase that catalyzes the conversion of malate to malyl coenzyme A; and
(c) a gene encoding malyl coenzyme A lyase that catalyzes the conversion of malyl coenzyme A to glyoxylate and acetyl-CoA, wherein the recombinant microorganism does not catalyze the conversion of oxaloacetate to malate.
4. The recombinant microorganism of any preceding embodiment, wherein the recombinant microorganism does not produce isopropyl alcohol, ethanol, acetone, citric acid, itaconic acid, acetic acid, butyric acid, (poly-)3-hydroxybutyric acid, 3-hydroxyisobutyric acid, 3-aminoisobutyric acid, 2-hydroxyisobutyric acid, methacrylic acid, (poly)glutamic acid, glutamic acid, arginine, ornithine, citrulline, leucine, isoleucine, or proline via the acetyl-CoA produced by the malyl coenzyme A lyase.
5. The recombinant microorganism of any preceding embodiment, wherein the acetyl-CoA produced by the malyl coenzyme A lyase combines with the OAA to increase the biosynthesis of GA and/or glycine.
6. The recombinant microorganism of any preceding embodiment, wherein the microorganism comprises a mutation in the gene encoding malate dehydrogenase, wherein the mutation results in a partial or complete inhibition of the malate dehydrogenase activity that catalyzes the conversion of oxaloacetate to malate, malate to pyruvate and/or malate to oxaloacetate.
7. The recombinant microorganism of any preceding embodiment, wherein the microorganism comprises a gene encoding NADH-dependent glyoxylate reductase that catalyzes the conversion of glyoxylate to glycolate or a gene encoding NADPH-dependent glyoxylate reductase that catalyzes the conversion of glyoxylate to glycolate.
8. The recombinant microorganism of any preceding embodiment, wherein the microorganism comprises a gene encoding alanine-glyoxylate aminotransferase, a gene encoding glycine dehydrogenase, a gene encoding glycine transaminase, a gene encoding serine-glyoxylate transaminase, and/or a gene encoding glycine oxidase to catalyze the conversion of glyoxylate to glycine.
9. The recombinant microorganism of any preceding embodiment, wherein the malate dehydrogenase that catalyzes the carboxylation of pyruvate to malate is from the Enzyme Classification (E.C.) 1.1.1.38, E.C. 1.1.1.39, or E.C. 1.1.1.40.
10. The recombinant microorganism of any preceding embodiment, wherein the malate dehydrogenase that catalyzes the conversion of oxaloacetate to malate is from the Enzyme Classification (E.C.) 1.1.1.37.
11. The recombinant microorganism of any preceding embodiment, wherein the gene encoding the malate dehydrogenase that catalyzes the carboxylation of pyruvate to malate is selected from the group consisting of: maeA, maeB, dme, mez, mae1, nad-me1, and nad-me2 or homologs thereof.
12. The recombinant microorganism of any preceding embodiment, wherein the gene maeA is from *E. coli, Pseudomonas,* or *Bacillus*; the gene maeB is from *E. coli* or *Salmonella*; the gene dme is from *Rhizobium*; the gene mez is from *Mycobacterium*; the gene mae1 is from *S. cerevisiae*; and the gene nad-me1 or nad-me2 is from *Arabidopsis thaliana*.
13. The recombinant microorganism of any preceding embodiment, wherein the gene maeA is from *B. subtilis*; the gene dme is from *R. melilote*; or the gene mez is from *Mycobacterium tuberculosis*.

14. The recombinant microorganism of any preceding embodiment, wherein the gene encoding the malate dehydrogenase that catalyzes the conversion of oxaloacetate to malate is selected from the group consisting of: gene mdh from *E. coli, Corynebacterium, Streptomyces, Saccharomyces* and *Arabidopsis* or homologs thereof.

15. The recombinant microorganism of any preceding embodiment, wherein the gene mdh is from *S. coelicolor* or gene mdh1/2/3 from *S. cerevisiae*.

16. The recombinant microorganism of any preceding embodiment, wherein the gene encoding malate thiokinase is sucCD and/or SucCD-2 and/or mtkAB from *Methylobacterium* sp., *Methylobacterium extorquens, Escherichia coli, Thermus thermophiles, Hyphomicrobium* sp., *Methanocaldococcus jannaschii, Methanothermobacter thermautotrophicus, Rhizobium, Methylococcus capsulatus* or *Pseudomonas*; or homologs thereof.

17. The recombinant microorganism of any preceding embodiment, wherein the gene encoding malyl coenzyme A lyase is mcl and/or Mcl1 and/or mclA from *Methylobacterium extorquens, Rhodobacter sphaeroides, Streptomyces, Chloroflexus aurantiacus, Nitrosomonas europaea, Methylococcus capsulans, Nereida ignava, Hyphomicrobium methylovorum, Thalassobius activus, Roseobacter litoralis, Hyphomicrobium denitrificans, R. sphaeroides, Mycobacterium smegmatis* or *Rhodococcus fascians*; or homologs thereof.

18. The recombinant microorganism of any preceding embodiment, wherein the gene encoding pyruvate carboxylase is pyc from *Rhizobium etli*, PYC1 or PYC2 from yeast or pyc from *B. subtilis*; or homologs thereof.

19. The recombinant microorganism of any preceding embodiment, wherein the gene encoding phosphoenolpyruvate carboxylase is ppc from *E. coli*, ppc or pepC from *R. marinus*, ppcA from *M. thermautotrophicus*, pep1 from *Z. mays*, ppc1/2/3 from *A. thaliana*, ppc from *G. max* or is from *Rhodothermus, Corynebacterium, Salmonella, Hyphomicrobium, Streptococcus, Streptomyces, Pantoea, Bacillus, Clostridium, Pseudomonas, Rhodopseudomonas, Nicotiana tabacum, Amaranthus hypochondriacus, Triticum aestivum* or *Medicago sativa*; or homologs thereof.

20. The recombinant microorganism of any preceding embodiment, wherein the gene encoding phosphoenolpyruvate carboxykinase is pck or pckA from *Escherichia coli*, pckA from *Selenomonas ruminantium*, pckA from *Salmonella typhimurium*, pckA from *Klebsiella* sp., pckA from *Thermus* sp, pck or pckA from *Ruminococcus albus* or *Ruminococcus flavefaciens*, pckA from *Actinobacillus succinogenes*, pck or pckA from *Streptococcus bovis*, or is from *Bacillus, Ruminiclostridium thermocellum, Klebsiella, Mycobacterium*; or homologs thereof.

21. The recombinant microorganism of any preceding embodiment, wherein the microorganism comprises:
(a) a gene encoding citrate synthase to convert OAA and acetyl-coA produced by the malyl-coA lyase to citrate;
(b) a gene encoding citrate hydro-lyase to convert citrate to cis-aconitate;
(c) a gene encoding D-threo-isocitrate hydro-lyase or aconitase to convert cis-aconitate to isocitrate;
(d) a gene encoding isocitrate lyase to convert isocitrate to succinate and glyoxylate;
(e) a gene encoding succinate dehydrogenase to convert succinate to fumarate; and
(f) a gene encoding fumarase to convert fumarate to malate.

22. The recombinant microorganism of any preceding embodiment, wherein the microorganism comprises a loss of function mutation or deletion of the gene encoding malate synthase.

23. The recombinant microorganism of any preceding embodiment, wherein the gene encoding glyoxylate reductase activity is selected from the group consisting of: ycdW and/or yiaE from *E. coli*, GOR1 from *S. cerevisiae*, gyaR from *Thermococcus litoralis* and/or GLYR1 from *A. thaliana*.

24. The recombinant microorganism of any preceding embodiment, wherein the pyruvate carboxylase that converts pyruvate to OAA is from the Enzyme Classification System No. E.C. 6.4.1.1; the phosphoenolpyruvate carboxylase that converts phosphoenolpyruvate to OAA is from the E.C. 4.1.1.31; the phosphoenolpyruvate carboxykinase that converts phosphoenolpyruvate to OAA is from the E.C. 4.1.1.32 and E.C. 4.1.1.49.

25. The recombinant microorganism of any preceding embodiment, wherein the malate thiokinase that converts malate to malyl coenzyme A is from the Enzyme Classification System No. E.C. 6.2.1.4, E.C. 6.2.1.5, E.C. 6.2.1.9, or E.C. 6.2.1.-; and/or the malyl coenzyme A lyase that converts malyl coenzyme A to glyoxylate and acetyl-CoA is from the E.C. 4.3.1.24 or E.C. 4.3.1.25.

26. The recombinant microorganism of any preceding embodiment, wherein one or more genes are expressed heterologously.

27. The recombinant microorganism of any preceding embodiment, wherein the microorganism comprises a deletion or modification that decreases the activity of one or more endogenous genes selected from the group consisting of:
(a) a gene encoding isocitrate dehydrogenase;
(b) a gene encoding pyruvate dehydrogenase, pyruvate oxidase and/or pyruvate formate-lyase;
(c) a gene encoding pyruvate kinase, and
(d) a gene encoding glycolate oxidase.

28. The recombinant microorganism of any preceding embodiment, wherein the gene encoding malate synthase is aceB and/or glcB from *E. coli* or DAL7 and/or MLS1 from yeast.

29. The recombinant microorganism of any preceding embodiment, wherein the gene encoding isocitrate dehydrogenase is icd from *E. coli* or IDP2 and/or IDH1/2 from yeast.

30. The recombinant microorganism of any preceding embodiment, wherein the gene encoding pyruvate dehydrogenase is aceE and/or aceF from *E. coli*.

31. The recombinant microorganism of any preceding embodiment, wherein the gene encoding pyruvate kinase is pykA and/or pykF from *E. coli*.

32. The recombinant microorganism of any preceding embodiment, wherein the gene encoding glycolate oxidase is glcD, glcE, glcF, and/or glcG from *E. coli*.

33. The recombinant microorganism of any preceding embodiment, wherein the yeast is *S. cerevisiae*.

34. The recombinant microorganism of any preceding embodiment, wherein the microorganism comprises a deletion or modification that decreases the activity of one or more endogenous genes selected from the group consisting of:
(a) a gene encoding glyoxylate carboligase;
(b) a gene encoding 2-oxo-4-hydroxyglutarate aldolase;
(c) a gene encoding glycoaldehyde reductase; and
(d) a gene encoding a repressor of isocitrate lyase.

35. The recombinant microorganism of any preceding embodiment, wherein the gene encoding glyoxylate carboligase is gcl; the gene encoding 2-oxo-4-hydroxyglutarate aldolase is edA; the gene encoding glycoaldehyde reductase is fucO and/or gldA; and the gene encoding the repressor of isocitrate lyase is iclR.

36. The recombinant microorganism of any preceding embodiment, wherein the level of expression of a gene encoding alanine-glyoxylate aminotransferase, a gene encoding glycine dehydrogenase, a gene encoding glycine transaminase, a gene encoding serine-glyoxylate aminotransferase, and/or a gene encoding glycine oxidase is increased.

37. The recombinant microorganism of any preceding embodiment, wherein the level of expression of a gene encoding alanine transaminase and/or a gene encoding NADPH-dependent glutamate synthase is increased.

38. The recombinant microorganism of any preceding embodiment, wherein the microorganism utilizes NADH and $CO_2$ generated by other glycolic acid and/or glycine producing pathways in the reactions catalyzed by malate dehydrogenase, pyruvate carboxylase, phosphoenolpyruvate carboxylase, phosphoenolpyruvate carboxykinase, malate thiokinase, and malyl coenzyme A lyase.

39. The recombinant microorganism of any preceding embodiment, wherein the microorganism utilizes exogenously added $CO_2$, a carbonate, and/or a reducing agent in the reactions catalyzed by malate dehydrogenase, pyruvate carboxylase, phosphoenolpyruvate carboxylase, phosphoenolpyruvate carboxykinase, malate thiokinase, and malyl coenzyme A lyase.

40. The recombinant microorganism of any preceding embodiment, wherein the reducing agent is hydrogen, electrons, and/or NAD(P)H.

41. The recombinant microorganism of any preceding embodiment, wherein the reducing agent comes from an external source.

42. The recombinant microorganism of any preceding embodiment, wherein the microorganism utilizes NADH and $CO_2$ generated by a serine/hydroxypyruvate-based pathways in the reactions catalyzed by malate dehydrogenase, pyruvate carboxylase, phosphoenolpyruvate carboxylase, phosphoenolpyruvate carboxykinase, malate thiokinase, and malyl coenzyme A lyase.

43. The recombinant microorganism of any preceding embodiment, wherein the microorganism utilizes NADH and $CO_2$ generated by a glyoxylate shunt pathway in the reactions catalyzed by malate dehydrogenase, pyruvate carboxylase, phosphoenolpyruvate carboxylase, phosphoenolpyruvate carboxykinase, malate thiokinase, and malyl coenzyme A lyase.

44. The recombinant microorganism of any preceding embodiment, wherein the microorganism utilizes NADH and $CO_2$ generated by a D-erythrose to glycoaldehyde based pathways in the reactions catalyzed by malate dehydrogenase, pyruvate carboxylase, phosphoenolpyruvate carboxylase, phosphoenolpyruvate carboxykinase, malate thiokinase, and malyl coenzyme A lyase.

45. The recombinant microorganism of any preceding embodiment, wherein the microorganism utilizes NADH and $CO_2$ generated by a pentose derivative to glycoaldehyde based pathways in the reactions catalyzed by malate dehydrogenase, pyruvate carboxylase, phosphoenolpyruvate carboxylase, phosphoenolpyruvate carboxykinase, malate thiokinase, and malyl coenzyme A lyase.

46. The recombinant microorganism of any preceding embodiment, wherein the microorganism is selected from the group consisting of bacterium, yeast, and fungus.

47. The recombinant microorganism of any preceding embodiment, wherein the microorganism is a bacterium selected from the group consisting of Enterobacteriaceae, Clostridiaceae, Bacillaceae, Streptomycetaceae, and Corynebacteriaceae.

48. The recombinant microorganism of any preceding embodiment, wherein the microorganism is a species of *Escherichia*, *Clostridium*, *Bacillus*, *Klebsiella*, *Pantoea*, *Salmonella*, *Lactobacillus*, or *Corynebacterium*.

49. The recombinant microorganism of any preceding embodiment, wherein the microorganism is *Escherichia coli* or *Corynebacterium glutamicum* or *Clostridium acetobutylicum* or *Bacillus subtilis*.

50. The recombinant microorganism of any preceding embodiment, wherein the microorganism is a yeast selected from the family Saccharomycetaceae.

51. The recombinant microorganism of any preceding embodiment, wherein the microorganism is a species of *Saccharomyces*.

52. The recombinant microorganism of any preceding embodiment, wherein the microorganism is *Saccharomyces cerevisiae*.

53. The recombinant microorganism of any preceding embodiment, wherein the synthesis of glycolic acid and/or glycine is increased by increasing the level of expression or the activity or the specificity of at least one enzyme selected from the group consisting of: pyruvate carboxylase, phosphoenolpyruvate carboxylase, phosphoenolpyruvate carboxykinase, malate dehydrogenase, malate thiokinase, malyl coenzyme A lyase, alanine-glyoxylate aminotransferase, glycine dehydrogenase, glycine transaminase, serine-glyoxylate transaminase, glycine oxidase, NADH-dependent glyoxylate reductase, and NADPH-dependent glyoxylate reductase.

54. The recombinant microorganism of any preceding embodiment, wherein the synthesis of glycolic acid and/or glycine is increased by decreasing the level of expression or the activity or the specificity of at least one enzyme selected from the group consisting of: malate synthase, isocitrate dehydrogenase, pyruvate dehydrogenase, pyruvate oxidase and/or pyruvate formate-lyase, pyruvate kinase, glucose-6-phosphate isomerase, glyoxylate carboligase, 2-oxo-4-hydroxyglutarate aldolase, glycoaldehyde reductase, and glycolate oxidase.

55. The recombinant microorganism of any preceding embodiment, wherein the synthesis of glycolic acid and/or glycine is increased by decreasing the level of expression of a gene encoding a repressor of isocitrate lyase.

56. A method of producing glycolic acid and/or glycine using a recombinant microorganism of any preceding embodiment, wherein the method comprises cultivating the recombinant microorganism in a culture medium containing a feedstock providing a carbon source until the glycolic acid and/or glycine are produced.

57. The method of any preceding embodiment, wherein the carbon source is selected from the group consisting of: sugars, glycerol, alcohols, organic acids, alkanes, fatty acids, hemicellulose, lignocellulose, proteins, carbon dioxide, and carbon monoxide.

58. The method of any preceding embodiment, wherein the carbon source is a hexose and/or pentose sugar.

59. The method of any preceding embodiment, wherein the carbon source is glucose.

60. The method of any preceding embodiment, wherein the carbon source is sucrose.

61. The method of any preceding embodiment, wherein the carbon source comprises a biomass hydrolysate comprising hemicellulose.

62. The method of any preceding embodiment, wherein the carbon source is $CO_2$ or carbonate.
63. The method of any preceding embodiment, wherein the carbonate is $HCO_3^-$.
64. A method of producing a recombinant microorganism that produces glycolic acid and/or glycine from glyoxylate, comprising introducing into the microorganism:
(a) a gene encoding malate dehydrogenase that catalyzes the conversion of pyruvate to malate;
(b) a gene encoding malate thiokinase that catalyzes the conversion of malate to malyl coenzyme A; and
(c) a gene encoding malyl coenzyme A lyase that catalyzes the conversion of malyl coenzyme A to glyoxylate and acetyl-CoA.
65. A method of producing a recombinant microorganism that produces glycolic acid and/or glycine from glyoxylate, comprising introducing into the microorganism:
(a) a gene encoding pyruvate carboxylase that catalyzes the conversion of pyruvate to OAA, and/or a gene encoding phosphoenolpyruvate carboxylase that catalyzes the conversion of phosphoenolpyruvate to OAA, and/or
a gene encoding phosphoenolpyruvate carboxykinase that catalyzes the conversion of phosphoenolpyruvate to OAA;
(b) a gene encoding malate dehydrogenase that catalyzes the conversion of OAA to malate;
(c) a gene encoding malate thiokinase that catalyzes the conversion of malate to malyl coenzyme A; and
(d) a gene encoding malyl coenzyme A lyase that catalyzes the conversion of malyl coenzyme A to glyoxylate and acetyl-CoA, wherein the acetyl-CoA produced by the malyl coenzyme A lyase combines with the OAA to increase the biosynthesis of GA and/or glycine.
66. A method of producing a recombinant microorganism that produces glycolic acid and/or glycine from glyoxylate, comprising introducing into the microorganism:
(a) a gene encoding pyruvate carboxylase that catalyzes the conversion of pyruvate to oxaloacetate (OAA), and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA;
(b) a gene encoding malate thiokinase that catalyzes the conversion of malate to malyl coenzyme A; and
(c) a gene encoding malyl coenzyme A lyase that catalyzes the conversion of malyl coenzyme A to glyoxylate and acetyl-CoA, wherein the recombinant microorganism does not catalyze the conversion of oxaloacetate to malate.
67. The method of any preceding embodiment, wherein the gene encoding malate dehydrogenase comprises a mutation that results in a partial or complete inhibition of the malate dehydrogenase activity that catalyzes the conversion of oxaloacetate to malate, malate to pyruvate or malate to oxaloacetate.
68. The method of any preceding embodiment, comprising introducing into the microorganism;
(a) a gene encoding NADH-dependent glyoxylate reductase that catalyzes the conversion of glyoxylate to glycolate;
(b) a gene encoding NADPH-dependent glyoxylate reductase that catalyzes the conversion of glyoxylate to glycolate; or
(i) a gene encoding alanine-glyoxylate aminotransferase, a gene encoding glycine dehydrogenase, a gene encoding glycine transaminase, a gene encoding serine-glyoxylate transaminase, and/or a gene encoding glycine oxidase that catalyzes the conversion of glyoxylate to glycine.
69. The method of any preceding embodiment, comprising introducing into the microorganism a loss of function mutation or deletion of the gene encoding malate synthase.
70. The method of any preceding embodiment, comprising introducing into the microorganism a deletion or modification that reduces the activity of one or more enzymes encoded by the genes selected from the group consisting of:
(a) a gene encoding isocitrate dehydrogenase;
(b) a gene encoding pyruvate dehydrogenase, pyruvate oxidase and/or pyruvate formate-lyase;
(c) a gene encoding pyruvate kinase;
(d) a gene encoding glycolate oxidase; and
(e) a gene encoding glucose-6-phosphate isomerase.
71. The method of any preceding embodiment, comprising introducing into the microorganism a deletion or modification that reduces the activity of one or more enzymes encoded by the genes selected from the group consisting of:
(a) a gene encoding glyoxylate carboligase;
(b) a gene encoding 2-oxo-4-hydroxyglutarate aldolase;
(c) a gene encoding glycoaldehyde reductase; and
(d) a gene encoding a repressor of isocitrate lyase.
72. The method of any preceding embodiment, comprising introducing a gain of function mutation into the gene encoding alanine-glyoxylate aminotransferase, the gene encoding alanine-glyoxylate aminotransferase glyoxylate to glycine, the gene encoding glycine dehydrogenase, the gene encoding glycine transaminase, the gene encoding serine-glyoxylate transaminase, and/or the gene encoding glycine oxidase that catalyze the conversion of glyoxylate to glycine.
73. The method of any preceding embodiment, comprising introducing a gain of function mutation into a gene encoding alanine transaminase and/or a gene encoding NADPH-dependent glutamate synthase.
74. The method of any preceding embodiment, wherein the recombinant microorganism is selected from the group consisting of bacterium, yeast, and fungus.
75. The method of any preceding embodiment, wherein the recombinant microorganism is a bacterium selected from the group consisting of Enterobacteriaceae, Clostridiaceae, Bacillaceae, Streptomycetaceae, and Corynebacteriaceae.
76. The method of any preceding embodiment, wherein the recombinant microorganism is a species of *Escherichia, Clostridium, Bacillus. Klebsiella, Pantoea, Salmonella, Lactobacillus*, or *Corynebacterium*.
77. The method of any preceding embodiment, wherein the recombinant microorganism is *Escherichia coli* or *Corynebacterium glutamicum* or *Clostridium acetobutylicum* or *Bacillus subtilis*.
78. The method of any preceding embodiment, wherein the recombinant microorganism is a yeast selected from the family Saccharomycetaceae.
79. The method of any preceding embodiment, wherein the recombinant microorganism is a species of *Saccharomyces*.
80. The method of any preceding embodiment, wherein the recombinant microorganism is *Saccharomyces cerevisiae*.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

The invention claimed is:

1. A glyoxylate producing recombinant microorganism for the synthesis of glycolic acid (GA) and/or glycine, comprising:
   (a) a gene encoding malate thiokinase that catalyzes the conversion of malate to malyl coenzyme A; and
   (b) a gene encoding malyl coenzyme A lyase that catalyzes the conversion of malyl coenzyme A to glyoxylate and acetyl-CoA, wherein the acetyl-CoA produced by the malyl coenzyme A lyase combines with oxaloacetate (OAA) to increase the biosynthesis of GA and/or glycine;
   further comprising:
   (c) a gene encoding malate dehydrogenase that catalyzes the conversion of pyruvate to malate; or
   (d) a gene encoding pyruvate carboxylase that catalyzes the conversion of pyruvate to OAA, and/or a gene encoding phosphoenolpyruvate carboxylase that catalyzes the conversion of phosphoenolpyruvate to OAA, and/or a gene encoding phosphoenolpyruvate carboxykinase that catalyzes the conversion of phosphoenolpyruvate to OAA; and further comprising:
   (e) a gene encoding NADH-dependent glyoxylate reductase that catalyzes the conversion of glyoxylate to glycolate or a gene encoding NADPH-dependent glyoxylate reductase that catalyzes the conversion of glyoxylate to glycolate or
   (f) a gene encoding alanine-glyoxylate aminotransferase, a gene encoding glycine dehydrogenase, a gene encoding glycine transaminase, a gene encoding serine-glyoxylate transaminase, and/or a gene encoding glycine oxidase to catalyze the conversion of glyoxylate to glycine.

2. The recombinant microorganism of claim 1, wherein the microorganism further comprises a mutation in the gene encoding malate dehydrogenase, wherein the mutation results in a partial or complete inhibition of the malate dehydrogenase activity that catalyzes the conversion of oxaloacetate to malate, malate to pyruvate and/or malate to oxaloacetate.

3. The recombinant microorganism of claim 1, wherein the gene encoding the malate dehydrogenase that catalyzes the carboxylation of pyruvate to malate is selected from the group consisting of: maeA, maeB, dme, mez, mae1, nad-me1, and nad-me2 or homologs thereof.

4. The recombinant microorganism of claim 3, wherein the gene maeA is from *B. subtillis*; the gene dme is from *R. melilote*; or the gene mez is from *Mycobacterium tuberculosis*.

5. The recombinant microorganism of claim 1, wherein the gene encoding the malate dehydrogenase that catalyzes the conversion of oxaloacetate to malate is selected from the group consisting of: gene mdh from *E. coli*, *Corynebacterium*, *Streptomyces*, *Saccharomyces* and *Arabidopsis* or homologs thereof.

6. The recombinant microorganism of claim 1, wherein the gene encoding malate thiokinase is sucCD and/or SucCD-2 and/or mtkAB from *Methylobacterium sp.*, *Methylobacterium extorquens*, *Escherichia coli*, *Thermus thermophiles*, *Hyphomicrobium sp.*, *Methanocaldococcus jannaschii*, *Methanothermobacter thermautotrophicus*, *Rhizobium*, *Methylococcus capsulatus* or *Pseudomonas*; or homologs thereof.

7. The recombinant microorganism of claim 1, wherein the gene encoding malyl coenzyme A lyase is mcl and/or Mcl1 and/or mclA from *Methylobacterium extorquens*, *Rhodobacter sphaeroides*, *Streptomyces*, *Chloroflexus aurantiacus*, *Nitrosomonas europaea*, *Methylococcus capsulans*, *Nereida ignava*, *Hyphomicrobium methylovorum*, *Thalassobius activus*, *Roseobacter litoralis*, *Hyphomicrobium denitrificans*, *R. sphaeroides*, *Mycobacterium smegmatis* or *Rhodococcus fascians*; or homologs thereof.

8. The recombinant microorganism of claim 1, wherein the gene encoding pyruvate carboxylase is pyc from *Rhizobium etli*, PYC1 or PYC2 from yeast or pyc from *B. subtilis*; or homologs thereof.

9. The recombinant microorganism of claim 1, wherein the gene encoding phosphoenolpyruvate carboxylase is ppc from *E. coli*, ppc or pepC from *R. marinus*, ppcA from *M. thermautotrophicus*, pep1 from *Z. mays*, ppc1/2/3 from *A. thaliana*, ppc from *G. max* or is from *Rhodothermus, Corynebacterium, Salmonella, Hyphomicrobium, Streptococcus, Streptomyces, Pantoea, Bacillus, Clostridium, Pseudomonas, Rhodopseudomonas, Nicotiana tabacum, Amaranthus hypochondriacus, Triticum aestivum* or *Medicago sativa*; or homologs thereof.

10. The recombinant microorganism of claim 1, wherein the gene encoding phosphoenolpyruvate carboxykinase is pck or pckA from *Escherichia coli*, pckA from *Selenomonas ruminantium*, pckA from *Salmonella typhimurium*, pckA from *Klebsiella* sp., pckA from *Thermus* sp, pck or pckA from *Ruminococcus albus* or *Ruminococcus flavefaciens*, pckA from *Actinobacillus succinogenes*, pck or pckA from *Streptococcus bovis*, or is from *Bacillus, Ruminiclostridium thermocellum, Klebsiella, Mycobacterium*; or homologs thereof.

11. The recombinant microorganism of claim 1, wherein the microorganism further comprises:
    (a) a gene encoding citrate synthase to convert OAA and acetyl-coA produced by the malyl-coA lyase to citrate;
    (b) a gene encoding citrate hydro-lyase to convert citrate to cis-aconitate;
    (c) a gene encoding D-threo-isocitrate hydro-lyase or aconitase to convert cis-aconitate to isocitrate;
    (d) a gene encoding isocitrate lyase to convert isocitrate to succinate and glyoxylate;
    (e) a gene encoding succinate dehydrogenase to convert succinate to fumarate; and
    (f) a gene encoding fumarase to convert fumarate to malate.

12. The recombinant microorganism of claim 1, wherein the microorganism further comprises a loss of function mutation or deletion of a gene encoding malate synthase, wherein the gene encoding malate synthase is aceB and/or glcB from *E. coli* or DAL7 and/or MLS1 from yeast.

13. The recombinant microorganism of claim 1, wherein the gene encoding NADH- or NADPH-dependent glyoxylate reductase is selected from the group consisting of: ycdW and/or yiaE from *E. coli*, GOR1 from *S. cerevisiae*, gyaR from *Thermococcus litoralis* and/or GLYR1 from *A. thaliana*.

14. The recombinant microorganism of claim 1, wherein the microorganism further comprises a deletion or modification that decreases the activity of one or more endogenous genes selected from the group consisting of:
    (a) a gene encoding isocitrate dehydrogenase, wherein the gene encoding isocitrate dehydrogenase is icd from *E. coli* or IDP2 and/or IDH1/2 from yeast:
    (b) a gene encoding pyruvate dehydrogenase, pyruvate oxidase and/or pyruvate formate-lyase;
    (c) a gene encoding pyruvate kinase; and
    (d) a gene encoding glycolate oxidase.

15. The recombinant microorganism of claim 1, wherein the microorganism further comprises a deletion or modification that decreases the activity of one or more endogenous genes selected from the group consisting of:
    (a) a gene encoding glyoxylate carboligase;
    (b) a gene encoding 2-oxo-4-hydroxyglutarate aldolase;
    (c) a gene encoding glycoaldehyde reductase; and
    (d) a gene encoding a repressor of isocitrate lyase.

16. The recombinant microorganism of claim 1, wherein further the level of expression of a gene encoding alanine transaminase and/or a gene encoding NADPH-dependent glutamate synthase is increased.

17. A method of producing glycolic acid and/or glycine using the recombinant microorganism of claim 1, wherein the method comprises cultivating the recombinant microorganism in a culture medium containing a feedstock providing a carbon source until the glycolic acid and/or glycine are produced.

18. The recombinant microorganism of claim 1, wherein the microorganism further comprises a deletion of an endogenous gene that encodes a glucose-6-phosphate isomerase (pgi).

* * * * *